(12) United States Patent
Fung et al.

(10) Patent No.: US 11,931,254 B2
(45) Date of Patent: Mar. 19, 2024

(54) LOW PROFILE PROSTHETIC MITRAL VALVE

(71) Applicant: Neovasc Tiara Inc., Richmond (CA)

(72) Inventors: Eric Soun-Sang Fung, Vancouver (CA); Karen Tsoek-Ji Wong, Richmond (CA); Ephraim Ben-Abraham, Rochester, MN (US)

(73) Assignee: Neovasc Tiara Inc., Richmond (CA)

( * ) Notice: Subject to any disclaimer, the term of this patent is extended or adjusted under 35 U.S.C. 154(b) by 0 days.

(21) Appl. No.: 17/694,389

(22) Filed: Mar. 14, 2022

(65) Prior Publication Data

US 2022/0192826 A1     Jun. 23, 2022

Related U.S. Application Data

(62) Division of application No. 16/906,782, filed on Jun. 19, 2020, now Pat. No. 11,311,376.

(60) Provisional application No. 62/864,008, filed on Jun. 20, 2019.

(51) Int. Cl.
*A61F 2/24* (2006.01)

(52) U.S. Cl.
CPC .......... *A61F 2/2418* (2013.01); *A61F 2/2409* (2013.01); *A61F 2/243* (2013.01); *A61F 2220/0008* (2013.01); *A61F 2230/0054* (2013.01); *A61F 2230/0067* (2013.01); *A61F 2250/0039* (2013.01)

(58) Field of Classification Search
CPC ....... A61F 2/2418; A61F 2/2409; A61F 2/243
See application file for complete search history.

(56) References Cited

U.S. PATENT DOCUMENTS

| 2,967,856 | A | 1/1961 | Coover, Jr. et al. |
| 11,311,376 | B2 | 4/2022 | Fung et al. |
| 2001/0021872 | A1 | 9/2001 | Bailey et al. |
| 2007/0142906 | A1 | 6/2007 | Figulla et al. |
| 2009/0276040 | A1 | 11/2009 | Rowe et al. |

(Continued)

FOREIGN PATENT DOCUMENTS

| AU | 2020295566 | 11/2023 |
| CA | 2874219 C | 7/2020 |

(Continued)

OTHER PUBLICATIONS

"U.S. Appl. No. 16/906,782, Corrected Notice of Allowability dated Mar. 24, 2022", 2 pgs.

(Continued)

*Primary Examiner* — Suba Ganesan
(74) *Attorney, Agent, or Firm* — Schwegman Lundberg & Woessner, P.A.

(57) ABSTRACT

A low-profile prosthetic valve for treating a native valve includes a radially expandable frame having an expanded configuration and a collapsed configuration. The atrial end of the prosthetic valve forms a flared shape that engages an atrial surface of the native valve. The flare shape flares downward toward a ventricle of the native valve when initially expanded followed by inversion of the flared shape to form a tapered shape tapering toward the ventricle and flaring toward the atrium of the native valve when fully expanded. The prosthetic valve also has a plurality of prosthetic valve leaflets that open and close to control fluid flow through the prosthetic valve.

20 Claims, 29 Drawing Sheets

(56) References Cited

U.S. PATENT DOCUMENTS

| | | | |
|---|---|---|---|
| 2013/0172992 A1 | 7/2013 | Gross et al. | |
| 2013/0325114 A1 | 12/2013 | Mclean et al. | |
| 2014/0052237 A1 | 2/2014 | Lane et al. | |
| 2014/0194983 A1* | 7/2014 | Kovalsky | A61F 2/2445 623/2.38 |
| 2017/0281343 A1* | 10/2017 | Christianson | A61F 2/2439 |
| 2018/0078370 A1 | 3/2018 | Kovalsky et al. | |
| 2020/0397570 A1 | 12/2020 | Fung et al. | |

FOREIGN PATENT DOCUMENTS

| | | |
|---|---|---|
| CN | 114144144 A | 3/2022 |
| DE | 10103955 B4 | 11/2001 |
| DE | 10033858 B4 | 1/2002 |
| DE | 102006052564 B3 | 12/2007 |
| DE | 102006013113 B4 | 12/2008 |
| DE | 102008015781 B4 | 9/2011 |
| DE | 102010051632 B4 | 9/2013 |
| DE | 102005032974 B4 | 11/2013 |
| DE | 102005052628 B4 | 6/2014 |
| DE | 10301026 B4 | 10/2014 |
| DE | 212013000104 U1 | 11/2014 |
| DE | 102008012438 B4 | 12/2014 |
| DE | 102011107551 B4 | 5/2015 |
| DE | 102011054176 B4 | 2/2016 |
| DE | 102014114762 B3 | 3/2016 |
| DE | 102013208038 B4 | 9/2016 |
| DE | 102010012677 B4 | 8/2017 |
| DE | 202011110951 U1 | 10/2017 |
| DE | 202011110985 U1 | 12/2017 |
| DE | 202016105963 U1 | 1/2018 |
| DE | 10394350 B4 | 5/2018 |
| DE | 102009024648 B4 | 5/2018 |
| DE | 102015206098 B4 | 9/2018 |
| DE | 10065824 B4 | 10/2018 |
| DE | 202017104793 U1 | 11/2018 |
| DE | 102011106928 B4 | 2/2019 |
| DE | 202016008737 U1 | 4/2019 |
| DE | 102013205519 B4 | 5/2019 |
| DE | 102008014730 B4 | 7/2019 |
| DE | 102018102940 B4 | 10/2019 |
| DE | 102009009158 B4 | 11/2020 |
| EP | 1077072 B1 | 11/2003 |
| EP | 1140244 B1 | 11/2003 |
| EP | 1214106 B1 | 11/2003 |
| EP | 1143864 B1 | 2/2004 |
| EP | 1220651 B1 | 3/2004 |
| EP | 1265534 B1 | 6/2004 |
| EP | 1347785 B1 | 7/2004 |
| EP | 1245202 B1 | 8/2004 |
| EP | 1161204 B1 | 9/2004 |
| EP | 1266641 B1 | 10/2004 |
| EP | 1102567 B1 | 11/2004 |
| EP | 1117446 B1 | 11/2004 |
| EP | 1107710 B1 | 12/2004 |
| EP | 1121070 B1 | 12/2004 |
| EP | 1217966 B1 | 12/2004 |
| EP | 1233731 B1 | 12/2004 |
| EP | 1294318 B1 | 12/2004 |
| EP | 1237510 B1 | 1/2005 |
| EP | 1034753 B1 | 2/2005 |
| EP | 1259194 B1 | 2/2005 |
| EP | 1121069 B1 | 3/2005 |
| EP | 1143879 B1 | 3/2005 |
| EP | 1023879 B1 | 4/2005 |
| EP | 1339356 B1 | 4/2005 |
| EP | 1214022 B1 | 5/2005 |
| EP | 1318774 B1 | 5/2005 |
| EP | 1088529 B1 | 6/2005 |
| EP | 1171060 B1 | 6/2005 |
| EP | 1251803 B1 | 6/2005 |
| EP | 1259776 B1 | 6/2005 |
| EP | 1272123 B1 | 6/2005 |
| EP | 1049422 B1 | 7/2005 |
| EP | 1230901 B1 | 8/2005 |
| EP | 1335683 B1 | 8/2005 |
| EP | 1307246 B1 | 9/2005 |
| EP | 1267753 B1 | 10/2005 |
| EP | 1284688 B1 | 10/2005 |
| EP | 1343536 B1 | 10/2005 |
| EP | 1027020 B1 | 11/2005 |
| EP | 1152780 B1 | 11/2005 |
| EP | 1171059 B1 | 11/2005 |
| EP | 1237508 B1 | 11/2005 |
| EP | 1303234 B1 | 11/2005 |
| EP | 1328215 B1 | 11/2005 |
| EP | 1341487 B1 | 11/2005 |
| EP | 1392197 B1 | 11/2005 |
| EP | 1469797 B1 | 11/2005 |
| EP | 1255505 B1 | 12/2005 |
| EP | 1360942 B1 | 12/2005 |
| EP | 1322260 B1 | 1/2006 |
| EP | 1359870 B1 | 1/2006 |
| EP | 1237586 B1 | 2/2006 |
| EP | 1112043 B1 | 4/2006 |
| EP | 1309360 B1 | 4/2006 |
| EP | 1322259 B1 | 5/2006 |
| EP | 1124592 B1 | 6/2006 |
| EP | 1237516 B1 | 6/2006 |
| EP | 1098673 B1 | 7/2006 |
| EP | 1124591 B1 | 7/2006 |
| EP | 1083845 B1 | 8/2006 |
| EP | 1155666 B1 | 8/2006 |
| EP | 1463462 B1 | 8/2006 |
| EP | 1684671 A1 | 8/2006 |
| EP | 1519695 B1 | 9/2006 |
| EP | 1444993 B1 | 10/2006 |
| EP | 1117350 B1 | 11/2006 |
| EP | 1212011 B1 | 11/2006 |
| EP | 1261294 B1 | 11/2006 |
| EP | 1318775 B1 | 11/2006 |
| EP | 1429690 B1 | 11/2006 |
| EP | 1173111 B1 | 12/2006 |
| EP | 1239795 B1 | 12/2006 |
| EP | 1299049 B1 | 12/2006 |
| EP | 1487382 B1 | 12/2006 |
| EP | 1112044 B1 | 1/2007 |
| EP | 1482997 B1 | 1/2007 |
| EP | 1117352 B1 | 2/2007 |
| EP | 1128849 B1 | 2/2007 |
| EP | 1392666 B1 | 2/2007 |
| EP | 1474077 B1 | 2/2007 |
| EP | 1251805 B1 | 3/2007 |
| EP | 1117334 B1 | 4/2007 |
| EP | 1263484 B1 | 5/2007 |
| EP | 1313410 B1 | 5/2007 |
| EP | 1370200 B1 | 5/2007 |
| EP | 1560526 B1 | 6/2007 |
| EP | 1173117 B1 | 7/2007 |
| EP | 1434615 B1 | 7/2007 |
| EP | 1465546 B1 | 7/2007 |
| EP | 1499366 B1 | 7/2007 |
| EP | 1225948 B1 | 8/2007 |
| EP | 1819304 A2 | 8/2007 |
| EP | 1519962 B1 | 9/2007 |
| EP | 1337285 B1 | 10/2007 |
| EP | 1112042 B1 | 11/2007 |
| EP | 1148821 B1 | 11/2007 |
| EP | 1143882 B1 | 12/2007 |
| EP | 1330189 B1 | 12/2007 |
| EP | 1489996 B1 | 12/2007 |
| EP | 1296618 B1 | 1/2008 |
| EP | 1401356 B1 | 1/2008 |
| EP | 1629795 B1 | 1/2008 |
| EP | 1128786 B1 | 2/2008 |
| EP | 1616532 B1 | 2/2008 |
| EP | 1289447 B1 | 3/2008 |
| EP | 1895942 A2 | 3/2008 |
| EP | 1115353 B1 | 5/2008 |
| EP | 1330190 B1 | 5/2008 |
| EP | 1383448 B1 | 6/2008 |
| EP | 1251804 B1 | 7/2008 |
| EP | 1294310 B1 | 7/2008 |

(56) References Cited

FOREIGN PATENT DOCUMENTS

| | | | |
|---|---|---|---|
| EP | 1313409 | B1 | 7/2008 |
| EP | 1395202 | B1 | 7/2008 |
| EP | 1395204 | B1 | 7/2008 |
| EP | 1395205 | B1 | 7/2008 |
| EP | 1423066 | B1 | 7/2008 |
| EP | 1560545 | B1 | 7/2008 |
| EP | 1605871 | B1 | 7/2008 |
| EP | 1671608 | B1 | 7/2008 |
| EP | 1690515 | B1 | 7/2008 |
| EP | 1180987 | B1 | 8/2008 |
| EP | 1337386 | B1 | 8/2008 |
| EP | 1492579 | B1 | 9/2008 |
| EP | 1524942 | B1 | 9/2008 |
| EP | 1627091 | B1 | 9/2008 |
| EP | 1827577 | B1 | 9/2008 |
| EP | 1259195 | B1 | 10/2008 |
| EP | 1704834 | B1 | 10/2008 |
| EP | 1146835 | B1 | 11/2008 |
| EP | 1498086 | B1 | 11/2008 |
| EP | 1622548 | B1 | 11/2008 |
| EP | 1235537 | B1 | 12/2008 |
| EP | 1237509 | B1 | 12/2008 |
| EP | 1355590 | B1 | 12/2008 |
| EP | 1455680 | B1 | 12/2008 |
| EP | 1472995 | B1 | 12/2008 |
| EP | 1513474 | B1 | 12/2008 |
| EP | 1562522 | B1 | 12/2008 |
| EP | 1620042 | B1 | 12/2008 |
| EP | 1690514 | B1 | 12/2008 |
| EP | 1258232 | B1 | 1/2009 |
| EP | 1420723 | B1 | 1/2009 |
| EP | 1570809 | B1 | 1/2009 |
| EP | 1395182 | B1 | 2/2009 |
| EP | 1408882 | B1 | 2/2009 |
| EP | 1482868 | B1 | 2/2009 |
| EP | 1255510 | B3 | 3/2009 |
| EP | 1330213 | B1 | 3/2009 |
| EP | 1429651 | B1 | 3/2009 |
| EP | 1610727 | B1 | 4/2009 |
| EP | 1617788 | B1 | 4/2009 |
| EP | 1634547 | B1 | 4/2009 |
| EP | 1790318 | B1 | 4/2009 |
| EP | 2040645 | A1 | 4/2009 |
| EP | 1250165 | B1 | 5/2009 |
| EP | 1842508 | B1 | 6/2009 |
| EP | 1968482 | B1 | 6/2009 |
| EP | 2072027 | A1 | 6/2009 |
| EP | 1343438 | B1 | 7/2009 |
| EP | 1406608 | B1 | 7/2009 |
| EP | 1509256 | B1 | 7/2009 |
| EP | 1626681 | B1 | 7/2009 |
| EP | 1723935 | B1 | 7/2009 |
| EP | 1803420 | B1 | 7/2009 |
| EP | 2073755 | A2 | 7/2009 |
| EP | 1401359 | B1 | 8/2009 |
| EP | 1411865 | B1 | 8/2009 |
| EP | 1485033 | B1 | 8/2009 |
| EP | 1581120 | B1 | 8/2009 |
| EP | 1620040 | B1 | 8/2009 |
| EP | 1684667 | B1 | 8/2009 |
| EP | 1872743 | B1 | 8/2009 |
| EP | 1100378 | B1 | 9/2009 |
| EP | 1198203 | B1 | 9/2009 |
| EP | 1370201 | B1 | 9/2009 |
| EP | 1408850 | B1 | 9/2009 |
| EP | 1472996 | B1 | 9/2009 |
| EP | 1478364 | B1 | 9/2009 |
| EP | 1653888 | B1 | 9/2009 |
| EP | 1785154 | B1 | 9/2009 |
| EP | 1881804 | B1 | 9/2009 |
| EP | 1903991 | B1 | 9/2009 |
| EP | 1418865 | B1 | 10/2009 |
| EP | 1561437 | B1 | 10/2009 |
| EP | 1615595 | B1 | 10/2009 |
| EP | 1353612 | B1 | 11/2009 |
| EP | 1348406 | B1 | 12/2009 |
| EP | 1370202 | B1 | 12/2009 |
| EP | 1603492 | B1 | 12/2009 |
| EP | 1670364 | B1 | 12/2009 |
| EP | 1759663 | B1 | 12/2009 |
| EP | 1994887 | B1 | 12/2009 |
| EP | 1615593 | B1 | 1/2010 |
| EP | 1643938 | B1 | 1/2010 |
| EP | 1863402 | B1 | 1/2010 |
| EP | 1943942 | B1 | 1/2010 |
| EP | 2010101 | B1 | 1/2010 |
| EP | 2081518 | B1 | 1/2010 |
| EP | 1703865 | B1 | 2/2010 |
| EP | 1276437 | B1 | 3/2010 |
| EP | 1276439 | B1 | 3/2010 |
| EP | 1411867 | B1 | 3/2010 |
| EP | 1458313 | B1 | 3/2010 |
| EP | 1520519 | B1 | 3/2010 |
| EP | 1648340 | B1 | 3/2010 |
| EP | 1682048 | B1 | 3/2010 |
| EP | 1773239 | B1 | 3/2010 |
| EP | 1935377 | B1 | 3/2010 |
| EP | 1994912 | B1 | 3/2010 |
| EP | 1154738 | B1 | 4/2010 |
| EP | 1531762 | B1 | 4/2010 |
| EP | 1600178 | B1 | 4/2010 |
| EP | 1626682 | B1 | 4/2010 |
| EP | 1511445 | B1 | 5/2010 |
| EP | 1198213 | B1 | 6/2010 |
| EP | 1250097 | B1 | 6/2010 |
| EP | 1272249 | B1 | 6/2010 |
| EP | 1978895 | B1 | 6/2010 |
| EP | 1572033 | B1 | 7/2010 |
| EP | 1968491 | B1 | 7/2010 |
| EP | 2019652 | B1 | 7/2010 |
| EP | 1610722 | B1 | 8/2010 |
| EP | 1682047 | B1 | 8/2010 |
| EP | 1952772 | B1 | 8/2010 |
| EP | 1427356 | B1 | 9/2010 |
| EP | 1631218 | B1 | 9/2010 |
| EP | 1765224 | B1 | 9/2010 |
| EP | 1871290 | B1 | 9/2010 |
| EP | 1895288 | B1 | 9/2010 |
| EP | 1895913 | B1 | 9/2010 |
| EP | 2014257 | B1 | 9/2010 |
| EP | 1176913 | B1 | 10/2010 |
| EP | 1178758 | B1 | 10/2010 |
| EP | 1248579 | B1 | 10/2010 |
| EP | 1913899 | B1 | 10/2010 |
| EP | 1259193 | B1 | 11/2010 |
| EP | 1928357 | B1 | 11/2010 |
| EP | 1968660 | B1 | 11/2010 |
| EP | 2249711 | A2 | 11/2010 |
| EP | 1408895 | B1 | 12/2010 |
| EP | 1465554 | B1 | 12/2010 |
| EP | 1732473 | B1 | 12/2010 |
| EP | 1768610 | B1 | 12/2010 |
| EP | 1827314 | B1 | 12/2010 |
| EP | 1940321 | B1 | 12/2010 |
| EP | 1964532 | B1 | 12/2010 |
| EP | 2078498 | B1 | 12/2010 |
| EP | 1600182 | B1 | 1/2011 |
| EP | 1617789 | B1 | 1/2011 |
| EP | 1663332 | B1 | 1/2011 |
| EP | 2147659 | B1 | 1/2011 |
| EP | 2268231 | A2 | 1/2011 |
| EP | 2273951 | A1 | 1/2011 |
| EP | 1187582 | B1 | 2/2011 |
| EP | 1450733 | B1 | 2/2011 |
| EP | 1803421 | B1 | 2/2011 |
| EP | 1833425 | B1 | 2/2011 |
| EP | 2029053 | B1 | 2/2011 |
| EP | 2068770 | B1 | 2/2011 |
| EP | 1441784 | B1 | 3/2011 |
| EP | 1534177 | B1 | 3/2011 |
| EP | 1893132 | B1 | 3/2011 |
| EP | 1951153 | B1 | 3/2011 |
| EP | 2289467 | A1 | 3/2011 |
| EP | 2299938 | A2 | 3/2011 |

(56) References Cited

FOREIGN PATENT DOCUMENTS

| | | | |
|---|---|---|---|
| EP | 1359978 | B1 | 4/2011 |
| EP | 1667750 | B1 | 4/2011 |
| EP | 1718249 | B1 | 4/2011 |
| EP | 1903989 | B1 | 4/2011 |
| EP | 2018122 | B1 | 4/2011 |
| EP | 1610728 | B1 | 5/2011 |
| EP | 2105110 | B1 | 5/2011 |
| EP | 1347717 | B1 | 6/2011 |
| EP | 2331018 | A1 | 6/2011 |
| EP | 1347791 | B1 | 7/2011 |
| EP | 1862128 | B1 | 7/2011 |
| EP | 2120795 | B1 | 7/2011 |
| EP | 2229920 | B1 | 7/2011 |
| EP | 1637087 | B1 | 8/2011 |
| EP | 2153799 | B1 | 8/2011 |
| EP | 2247263 | B1 | 8/2011 |
| EP | 2349095 | A1 | 8/2011 |
| EP | 2349097 | A1 | 8/2011 |
| EP | 2349098 | A1 | 8/2011 |
| EP | 2358307 | A1 | 8/2011 |
| EP | 1441672 | B1 | 9/2011 |
| EP | 1625832 | B1 | 9/2011 |
| EP | 2173279 | B1 | 9/2011 |
| EP | 2367505 | A1 | 9/2011 |
| EP | 2160150 | B1 | 10/2011 |
| EP | 2370138 | A2 | 10/2011 |
| EP | 1626679 | B1 | 11/2011 |
| EP | 1719476 | B1 | 11/2011 |
| EP | 1928355 | B1 | 11/2011 |
| EP | 2237747 | B1 | 11/2011 |
| EP | 2381895 | A2 | 11/2011 |
| EP | 2389121 | A1 | 11/2011 |
| EP | 1572031 | B1 | 12/2011 |
| EP | 1603493 | B1 | 12/2011 |
| EP | 1945109 | B1 | 12/2011 |
| EP | 1998688 | B1 | 12/2011 |
| EP | 2393442 | A2 | 12/2011 |
| EP | 2395944 | A1 | 12/2011 |
| EP | 1443877 | B1 | 1/2012 |
| EP | 2400922 | A1 | 1/2012 |
| EP | 1281375 | B1 | 2/2012 |
| EP | 1699501 | B1 | 2/2012 |
| EP | 1788984 | B1 | 2/2012 |
| EP | 1833415 | B1 | 2/2012 |
| EP | 1952785 | B1 | 2/2012 |
| EP | 2055266 | B1 | 2/2012 |
| EP | 2205184 | B1 | 2/2012 |
| EP | 2416736 | A1 | 2/2012 |
| EP | 1337188 | B1 | 3/2012 |
| EP | 1443974 | B1 | 3/2012 |
| EP | 1542623 | B1 | 3/2012 |
| EP | 1942835 | B1 | 3/2012 |
| EP | 2074964 | B1 | 3/2012 |
| EP | 2244661 | B1 | 3/2012 |
| EP | 2273928 | B1 | 3/2012 |
| EP | 2427144 | A1 | 3/2012 |
| EP | 2429455 | A1 | 3/2012 |
| EP | 1401336 | B1 | 4/2012 |
| EP | 1749544 | B1 | 4/2012 |
| EP | 2119417 | B1 | 4/2012 |
| EP | 2152330 | B1 | 4/2012 |
| EP | 2231069 | B1 | 4/2012 |
| EP | 2437688 | A1 | 4/2012 |
| EP | 2020958 | B1 | 5/2012 |
| EP | 2192875 | B1 | 5/2012 |
| EP | 2218425 | B1 | 5/2012 |
| EP | 2445450 | A2 | 5/2012 |
| EP | 1411847 | B1 | 6/2012 |
| EP | 1727499 | B1 | 6/2012 |
| EP | 2082690 | B1 | 6/2012 |
| EP | 1740747 | B1 | 7/2012 |
| EP | 1861044 | B1 | 7/2012 |
| EP | 2052699 | B1 | 7/2012 |
| EP | 2470121 | A2 | 7/2012 |
| EP | 2471492 | A1 | 7/2012 |
| EP | 1887975 | B1 | 8/2012 |
| EP | 2000116 | B1 | 8/2012 |
| EP | 2222247 | B1 | 8/2012 |
| EP | 2486894 | A1 | 8/2012 |
| EP | 1605870 | B1 | 9/2012 |
| EP | 1887980 | B1 | 9/2012 |
| EP | 2497445 | A1 | 9/2012 |
| EP | 1740126 | B1 | 10/2012 |
| EP | 1865889 | B1 | 10/2012 |
| EP | 2033593 | B1 | 10/2012 |
| EP | 2124824 | B1 | 10/2012 |
| EP | 2139431 | B1 | 10/2012 |
| EP | 2506777 | A1 | 10/2012 |
| EP | 2512952 | A2 | 10/2012 |
| EP | 1430853 | B1 | 11/2012 |
| EP | 1928512 | B1 | 11/2012 |
| EP | 2008615 | B1 | 11/2012 |
| EP | 2088965 | B1 | 11/2012 |
| EP | 2520249 | A1 | 11/2012 |
| EP | 2522307 | A1 | 11/2012 |
| EP | 1557138 | B1 | 12/2012 |
| EP | 1924221 | B1 | 12/2012 |
| EP | 2023859 | B1 | 12/2012 |
| EP | 2250970 | B1 | 12/2012 |
| EP | 2285317 | B1 | 12/2012 |
| EP | 2536353 | A1 | 12/2012 |
| EP | 2537486 | A1 | 12/2012 |
| EP | 1494731 | B1 | 1/2013 |
| EP | 1610752 | B1 | 1/2013 |
| EP | 1796597 | B1 | 1/2013 |
| EP | 1919397 | B1 | 1/2013 |
| EP | 1942834 | B1 | 1/2013 |
| EP | 2015709 | B1 | 1/2013 |
| EP | 2079400 | B1 | 1/2013 |
| EP | 2238947 | B1 | 1/2013 |
| EP | 2241287 | B1 | 1/2013 |
| EP | 2359774 | B1 | 1/2013 |
| EP | 2538878 | A1 | 1/2013 |
| EP | 2538881 | A1 | 1/2013 |
| EP | 2538882 | A1 | 1/2013 |
| EP | 2538883 | A1 | 1/2013 |
| EP | 1512383 | B1 | 2/2013 |
| EP | 1578474 | B1 | 2/2013 |
| EP | 1648339 | B1 | 2/2013 |
| EP | 1750622 | B1 | 2/2013 |
| EP | 1994482 | B1 | 2/2013 |
| EP | 2250975 | B1 | 2/2013 |
| EP | 2257242 | B1 | 2/2013 |
| EP | 2265225 | B1 | 2/2013 |
| EP | 2558032 | A1 | 2/2013 |
| EP | 1659992 | B1 | 3/2013 |
| EP | 1701668 | B1 | 3/2013 |
| EP | 2151216 | B1 | 3/2013 |
| EP | 2340075 | B1 | 3/2013 |
| EP | 2568924 | A2 | 3/2013 |
| EP | 1781183 | B1 | 4/2013 |
| EP | 1786367 | B1 | 4/2013 |
| EP | 1850795 | B1 | 4/2013 |
| EP | 1861041 | B1 | 4/2013 |
| EP | 2319458 | B1 | 4/2013 |
| EP | 2526898 | B1 | 4/2013 |
| EP | 2537487 | B1 | 4/2013 |
| EP | 2575681 | A1 | 4/2013 |
| EP | 1901682 | B1 | 5/2013 |
| EP | 1951166 | B1 | 5/2013 |
| EP | 1994913 | B1 | 5/2013 |
| EP | 2231070 | B1 | 5/2013 |
| EP | 2401970 | B1 | 5/2013 |
| EP | 2409651 | B1 | 5/2013 |
| EP | 2594230 | A1 | 5/2013 |
| EP | 1694246 | B1 | 6/2013 |
| EP | 1948087 | B1 | 6/2013 |
| EP | 2135559 | B1 | 6/2013 |
| EP | 1115335 | B1 | 7/2013 |
| EP | 1663339 | B1 | 7/2013 |
| EP | 1864687 | B1 | 7/2013 |
| EP | 1977719 | B1 | 7/2013 |
| EP | 2111337 | B1 | 7/2013 |
| EP | 2298237 | B1 | 7/2013 |

(56) References Cited

FOREIGN PATENT DOCUMENTS

| | | |
|---|---|---|
| EP | 2309949 B1 | 7/2013 |
| EP | 2608741 A2 | 7/2013 |
| EP | 2611388 A2 | 7/2013 |
| EP | 2611389 A2 | 7/2013 |
| EP | 2618781 A2 | 7/2013 |
| EP | 1599151 B1 | 8/2013 |
| EP | 1761211 B1 | 8/2013 |
| EP | 2047871 B1 | 8/2013 |
| EP | 2142144 B1 | 8/2013 |
| EP | 2150206 B1 | 8/2013 |
| EP | 2319459 B1 | 8/2013 |
| EP | 2397108 B1 | 8/2013 |
| EP | 2623068 A1 | 8/2013 |
| EP | 1758523 B1 | 9/2013 |
| EP | 1545392 B1 | 10/2013 |
| EP | 1638627 B1 | 10/2013 |
| EP | 1779868 B1 | 10/2013 |
| EP | 2073756 B1 | 10/2013 |
| EP | 2111190 B1 | 10/2013 |
| EP | 2651336 A1 | 10/2013 |
| EP | 1848375 B1 | 11/2013 |
| EP | 1928356 B1 | 11/2013 |
| EP | 1933766 B1 | 11/2013 |
| EP | 2109417 B1 | 11/2013 |
| EP | 2194925 B1 | 11/2013 |
| EP | 2387977 B1 | 11/2013 |
| EP | 2476394 B1 | 11/2013 |
| EP | 2529701 B1 | 11/2013 |
| EP | 1945142 B1 | 12/2013 |
| EP | 2387972 B1 | 12/2013 |
| EP | 2477555 B1 | 12/2013 |
| EP | 2670349 A2 | 12/2013 |
| EP | 2670351 A1 | 12/2013 |
| EP | 2117476 B1 | 1/2014 |
| EP | 2526895 B1 | 1/2014 |
| EP | 2526899 B1 | 1/2014 |
| EP | 2529696 B1 | 1/2014 |
| EP | 2529697 B1 | 1/2014 |
| EP | 2529698 B1 | 1/2014 |
| EP | 2529699 B1 | 1/2014 |
| EP | 2679198 A1 | 1/2014 |
| EP | 2688516 A1 | 1/2014 |
| EP | 1395214 B1 | 2/2014 |
| EP | 1499266 B1 | 2/2014 |
| EP | 1838241 B1 | 2/2014 |
| EP | 2520250 B1 | 2/2014 |
| EP | 2526977 B1 | 2/2014 |
| EP | 2693985 A1 | 2/2014 |
| EP | 2698129 A1 | 2/2014 |
| EP | 2699302 A2 | 2/2014 |
| EP | 1629794 B1 | 3/2014 |
| EP | 1919398 B1 | 3/2014 |
| EP | 2099508 B1 | 3/2014 |
| EP | 2399549 B1 | 3/2014 |
| EP | 2422823 B1 | 3/2014 |
| EP | 2706958 A1 | 3/2014 |
| EP | 1804860 B1 | 4/2014 |
| EP | 1926455 B1 | 4/2014 |
| EP | 2081519 B1 | 4/2014 |
| EP | 2117477 B1 | 4/2014 |
| EP | 2405966 B1 | 4/2014 |
| EP | 2420205 B1 | 4/2014 |
| EP | 2593048 B1 | 4/2014 |
| EP | 2713894 A2 | 4/2014 |
| EP | 2713955 A2 | 4/2014 |
| EP | 2723273 A2 | 4/2014 |
| EP | 1499265 B1 | 5/2014 |
| EP | 1594569 B1 | 5/2014 |
| EP | 2029056 B1 | 5/2014 |
| EP | 2257243 B1 | 5/2014 |
| EP | 1791500 B1 | 6/2014 |
| EP | 2073753 B1 | 6/2014 |
| EP | 2306933 B1 | 6/2014 |
| EP | 2331017 B1 | 6/2014 |
| EP | 2337522 B1 | 6/2014 |
| EP | 2389897 B1 | 6/2014 |
| EP | 2606723 B1 | 6/2014 |
| EP | 2739250 A1 | 6/2014 |
| EP | 1487350 B1 | 7/2014 |
| EP | 1977718 B1 | 7/2014 |
| EP | 2117469 B1 | 7/2014 |
| EP | 2124826 B1 | 7/2014 |
| EP | 2258316 B1 | 7/2014 |
| EP | 2747708 A1 | 7/2014 |
| EP | 2750630 A1 | 7/2014 |
| EP | 2750631 A1 | 7/2014 |
| EP | 1667604 B1 | 8/2014 |
| EP | 1786368 B1 | 8/2014 |
| EP | 2211779 B1 | 8/2014 |
| EP | 2217174 B1 | 8/2014 |
| EP | 2293740 B1 | 8/2014 |
| EP | 2367504 B1 | 8/2014 |
| EP | 2453942 B1 | 8/2014 |
| EP | 2475328 B1 | 8/2014 |
| EP | 2545884 B1 | 8/2014 |
| EP | 2571460 B1 | 8/2014 |
| EP | 2763708 A2 | 8/2014 |
| EP | 2765954 A1 | 8/2014 |
| EP | 1935378 B1 | 9/2014 |
| EP | 2246011 B1 | 9/2014 |
| EP | 2422749 B1 | 9/2014 |
| EP | 2531139 B1 | 9/2014 |
| EP | 2609893 B1 | 9/2014 |
| EP | 2777616 A1 | 9/2014 |
| EP | 2779945 A1 | 9/2014 |
| EP | 1853199 B1 | 10/2014 |
| EP | 2133039 B1 | 10/2014 |
| EP | 2549955 B1 | 10/2014 |
| EP | 2549956 B1 | 10/2014 |
| EP | 2651335 B1 | 10/2014 |
| EP | 2785281 A1 | 10/2014 |
| EP | 2793743 A1 | 10/2014 |
| EP | 2793749 A1 | 10/2014 |
| EP | 2793752 A1 | 10/2014 |
| EP | 2049721 B1 | 11/2014 |
| EP | 2142143 B1 | 11/2014 |
| EP | 2229921 B1 | 11/2014 |
| EP | 2288403 B1 | 11/2014 |
| EP | 2415421 B1 | 11/2014 |
| EP | 1551274 B1 | 12/2014 |
| EP | 1768735 B1 | 12/2014 |
| EP | 1959865 B1 | 12/2014 |
| EP | 2077718 B1 | 12/2014 |
| EP | 2303185 B1 | 12/2014 |
| EP | 2334857 B1 | 12/2014 |
| EP | 2365840 B1 | 12/2014 |
| EP | 2420207 B1 | 12/2014 |
| EP | 2422750 B1 | 12/2014 |
| EP | 2707073 B1 | 12/2014 |
| EP | 1768630 B1 | 1/2015 |
| EP | 2254515 B1 | 1/2015 |
| EP | 2641569 B1 | 1/2015 |
| EP | 2709559 B1 | 1/2015 |
| EP | 2825203 A1 | 1/2015 |
| EP | 1903990 B1 | 2/2015 |
| EP | 2255753 B1 | 2/2015 |
| EP | 2335649 B1 | 2/2015 |
| EP | 2522308 B1 | 2/2015 |
| EP | 2591754 B1 | 2/2015 |
| EP | 2835112 A1 | 2/2015 |
| EP | 2838473 A1 | 2/2015 |
| EP | 1861045 B1 | 3/2015 |
| EP | 2029057 B1 | 3/2015 |
| EP | 2193761 B1 | 3/2015 |
| EP | 2379010 B1 | 3/2015 |
| EP | 2416737 B1 | 3/2015 |
| EP | 2849678 A1 | 3/2015 |
| EP | 1791495 B1 | 4/2015 |
| EP | 2298252 B1 | 4/2015 |
| EP | 2536359 B1 | 4/2015 |
| EP | 2538879 B1 | 4/2015 |
| EP | 2609894 B1 | 4/2015 |
| EP | 2693984 B1 | 4/2015 |
| EP | 2712633 B1 | 4/2015 |

(56) References Cited

FOREIGN PATENT DOCUMENTS

| | | | |
|---|---|---|---|
| EP | 2747707 | B1 | 4/2015 |
| EP | 2856973 | A1 | 4/2015 |
| EP | 2862546 | A1 | 4/2015 |
| EP | 2863842 | A1 | 4/2015 |
| EP | 1465555 | B1 | 5/2015 |
| EP | 1924224 | B1 | 5/2015 |
| EP | 1992369 | B1 | 5/2015 |
| EP | 2410947 | B1 | 5/2015 |
| EP | 2484311 | B1 | 5/2015 |
| EP | 2654616 | B1 | 5/2015 |
| EP | 2866741 | A1 | 5/2015 |
| EP | 1646332 | B1 | 6/2015 |
| EP | 2745805 | B1 | 6/2015 |
| EP | 2749254 | B1 | 6/2015 |
| EP | 2877123 | A2 | 6/2015 |
| EP | 2882374 | A1 | 6/2015 |
| EP | 2884906 | A1 | 6/2015 |
| EP | 1729685 | B1 | 7/2015 |
| EP | 1976439 | B1 | 7/2015 |
| EP | 2068767 | B1 | 7/2015 |
| EP | 2068769 | B1 | 7/2015 |
| EP | 2444031 | B1 | 7/2015 |
| EP | 2455041 | B1 | 7/2015 |
| EP | 2498719 | B1 | 7/2015 |
| EP | 2558030 | B1 | 7/2015 |
| EP | 2752209 | B1 | 7/2015 |
| EP | 2892467 | A1 | 7/2015 |
| EP | 1702247 | B1 | 8/2015 |
| EP | 1729688 | B1 | 8/2015 |
| EP | 1887979 | B1 | 8/2015 |
| EP | 2032079 | B1 | 8/2015 |
| EP | 2219558 | B1 | 8/2015 |
| EP | 2234657 | B1 | 8/2015 |
| EP | 2250976 | B1 | 8/2015 |
| EP | 2262447 | B1 | 8/2015 |
| EP | 2303384 | B1 | 8/2015 |
| EP | 2387365 | B1 | 8/2015 |
| EP | 2560579 | B1 | 8/2015 |
| EP | 2575621 | B1 | 8/2015 |
| EP | 2590595 | B1 | 8/2015 |
| EP | 2709560 | B1 | 8/2015 |
| EP | 2755603 | B1 | 8/2015 |
| EP | 2906147 | A1 | 8/2015 |
| EP | 1534185 | B1 | 9/2015 |
| EP | 1765225 | B1 | 9/2015 |
| EP | 1778127 | B1 | 9/2015 |
| EP | 2094194 | B1 | 9/2015 |
| EP | 2201911 | B1 | 9/2015 |
| EP | 2306934 | B1 | 9/2015 |
| EP | 2397113 | B1 | 9/2015 |
| EP | 2453843 | B1 | 9/2015 |
| EP | 2459127 | B1 | 9/2015 |
| EP | 2675396 | B1 | 9/2015 |
| EP | 2675397 | B1 | 9/2015 |
| EP | 2736454 | B1 | 9/2015 |
| EP | 2754414 | A4 | 9/2015 |
| EP | 2790609 | B1 | 9/2015 |
| EP | 2805693 | B1 | 9/2015 |
| EP | 2911611 | A1 | 9/2015 |
| EP | 2916781 | A2 | 9/2015 |
| EP | 2919712 | A1 | 9/2015 |
| EP | 1734903 | B1 | 10/2015 |
| EP | 1863546 | B1 | 10/2015 |
| EP | 1900343 | B1 | 10/2015 |
| EP | 2081515 | B1 | 10/2015 |
| EP | 2191792 | B1 | 10/2015 |
| EP | 2254513 | B1 | 10/2015 |
| EP | 2381896 | B1 | 10/2015 |
| EP | 2450008 | B1 | 10/2015 |
| EP | 2544626 | B1 | 10/2015 |
| EP | 2561830 | B1 | 10/2015 |
| EP | 2600798 | B1 | 10/2015 |
| EP | 2626039 | B1 | 10/2015 |
| EP | 2647354 | B1 | 10/2015 |
| EP | 2729093 | B1 | 10/2015 |
| EP | 2836165 | B1 | 10/2015 |
| EP | 1863545 | B1 | 11/2015 |
| EP | 2303395 | B1 | 11/2015 |
| EP | 2497446 | B1 | 11/2015 |
| EP | 2772228 | B1 | 11/2015 |
| EP | 1482869 | B1 | 12/2015 |
| EP | 1551473 | B1 | 12/2015 |
| EP | 1748745 | B1 | 12/2015 |
| EP | 1755459 | B1 | 12/2015 |
| EP | 1850796 | B1 | 12/2015 |
| EP | 1922030 | B1 | 12/2015 |
| EP | 1954212 | B1 | 12/2015 |
| EP | 2424472 | B1 | 12/2015 |
| EP | 2470120 | B1 | 12/2015 |
| EP | 2542179 | B1 | 12/2015 |
| EP | 2948100 | A1 | 12/2015 |
| EP | 2948103 | A2 | 12/2015 |
| EP | 2950752 | A2 | 12/2015 |
| EP | 2959866 | A1 | 12/2015 |
| EP | 1991168 | B1 | 1/2016 |
| EP | 2254512 | B1 | 1/2016 |
| EP | 2422748 | B1 | 1/2016 |
| EP | 2962664 | A1 | 1/2016 |
| EP | 2964153 | A1 | 1/2016 |
| EP | 2967700 | A1 | 1/2016 |
| EP | 2967807 | A2 | 1/2016 |
| EP | 2967834 | A1 | 1/2016 |
| EP | 2967856 | A1 | 1/2016 |
| EP | 2967858 | A2 | 1/2016 |
| EP | 2967860 | A1 | 1/2016 |
| EP | 2967866 | A2 | 1/2016 |
| EP | 2977026 | A1 | 1/2016 |
| EP | 1754684 | B1 | 2/2016 |
| EP | 1835948 | B1 | 2/2016 |
| EP | 2012712 | B1 | 2/2016 |
| EP | 2285318 | B1 | 2/2016 |
| EP | 2731550 | B1 | 2/2016 |
| EP | 2926766 | B1 | 2/2016 |
| EP | 2982337 | A1 | 2/2016 |
| EP | 1585463 | B1 | 3/2016 |
| EP | 1638621 | B1 | 3/2016 |
| EP | 1804726 | B1 | 3/2016 |
| EP | 1865886 | B1 | 3/2016 |
| EP | 1887982 | B1 | 3/2016 |
| EP | 2150205 | B1 | 3/2016 |
| EP | 2278944 | B1 | 3/2016 |
| EP | 2291126 | B1 | 3/2016 |
| EP | 2517674 | B1 | 3/2016 |
| EP | 2520253 | B1 | 3/2016 |
| EP | 2526897 | B1 | 3/2016 |
| EP | 2621409 | A4 | 3/2016 |
| EP | 2670353 | B1 | 3/2016 |
| EP | 2674130 | B1 | 3/2016 |
| EP | 2780042 | B1 | 3/2016 |
| EP | 2991584 | A1 | 3/2016 |
| EP | 2991587 | A2 | 3/2016 |
| EP | 2991588 | A1 | 3/2016 |
| EP | 2994072 | A1 | 3/2016 |
| EP | 2994075 | A1 | 3/2016 |
| EP | 2996632 | A1 | 3/2016 |
| EP | 2996633 | A1 | 3/2016 |
| EP | 2996641 | A1 | 3/2016 |
| EP | 2999435 | A1 | 3/2016 |
| EP | 1420730 | B1 | 4/2016 |
| EP | 1545371 | B1 | 4/2016 |
| EP | 1592367 | B1 | 4/2016 |
| EP | 1708649 | B1 | 4/2016 |
| EP | 1871300 | B1 | 4/2016 |
| EP | 2168536 | B1 | 4/2016 |
| EP | 2399550 | B1 | 4/2016 |
| EP | 2433591 | B1 | 4/2016 |
| EP | 2478871 | B1 | 4/2016 |
| EP | 2536355 | B1 | 4/2016 |
| EP | 2572676 | B1 | 4/2016 |
| EP | 2606852 | B1 | 4/2016 |
| EP | 2621408 | B1 | 4/2016 |
| EP | 2626041 | B1 | 4/2016 |
| EP | 2633821 | B1 | 4/2016 |
| EP | 2670354 | B1 | 4/2016 |

(56) References Cited

FOREIGN PATENT DOCUMENTS

| | | | |
|---|---|---|---|
| EP | 2702965 B1 | 4/2016 |
| EP | 2704669 B1 | 4/2016 |
| EP | 2815725 B1 | 4/2016 |
| EP | 3007651 A1 | 4/2016 |
| EP | 3010564 A1 | 4/2016 |
| EP | 2194933 B1 | 5/2016 |
| EP | 2237746 B1 | 5/2016 |
| EP | 2378947 B1 | 5/2016 |
| EP | 2542184 B1 | 5/2016 |
| EP | 2572684 B1 | 5/2016 |
| EP | 2582326 B1 | 5/2016 |
| EP | 2618784 B1 | 5/2016 |
| EP | 2654623 B1 | 5/2016 |
| EP | 2656816 B1 | 5/2016 |
| EP | 2680791 B1 | 5/2016 |
| EP | 2693986 B1 | 5/2016 |
| EP | 2806805 B1 | 5/2016 |
| EP | 2866739 B1 | 5/2016 |
| EP | 2889020 B1 | 5/2016 |
| EP | 2926767 B1 | 5/2016 |
| EP | 2949292 B1 | 5/2016 |
| EP | 3019092 A1 | 5/2016 |
| EP | 1734902 B1 | 6/2016 |
| EP | 1906884 B1 | 6/2016 |
| EP | 2111800 B1 | 6/2016 |
| EP | 2160156 B1 | 6/2016 |
| EP | 2190379 B1 | 6/2016 |
| EP | 2193762 B1 | 6/2016 |
| EP | 2416739 B1 | 6/2016 |
| EP | 2453969 B1 | 6/2016 |
| EP | 2515800 B1 | 6/2016 |
| EP | 2558031 B1 | 6/2016 |
| EP | 2563236 B1 | 6/2016 |
| EP | 2572675 B1 | 6/2016 |
| EP | 2626040 B1 | 6/2016 |
| EP | 2704668 B1 | 6/2016 |
| EP | 2777611 B1 | 6/2016 |
| EP | 2815724 B1 | 6/2016 |
| EP | 2854710 B1 | 6/2016 |
| EP | 2901966 B1 | 6/2016 |
| EP | 3024527 A2 | 6/2016 |
| EP | 1605866 B1 | 7/2016 |
| EP | 1933756 B1 | 7/2016 |
| EP | 2393452 B1 | 7/2016 |
| EP | 2410948 B1 | 7/2016 |
| EP | 2412397 B1 | 7/2016 |
| EP | 2724690 B1 | 7/2016 |
| EP | 2815723 B1 | 7/2016 |
| EP | 2870945 B1 | 7/2016 |
| EP | 3038567 A1 | 7/2016 |
| EP | 3040054 A1 | 7/2016 |
| EP | 3042635 A1 | 7/2016 |
| EP | 3043745 A1 | 7/2016 |
| EP | 3043747 A1 | 7/2016 |
| EP | 3043755 A1 | 7/2016 |
| EP | 1401358 B1 | 8/2016 |
| EP | 1915105 B1 | 8/2016 |
| EP | 1937186 B1 | 8/2016 |
| EP | 2292186 B1 | 8/2016 |
| EP | 2379012 B1 | 8/2016 |
| EP | 2385809 B1 | 8/2016 |
| EP | 2536345 B1 | 8/2016 |
| EP | 2537490 B1 | 8/2016 |
| EP | 2549954 B1 | 8/2016 |
| EP | 2618779 B1 | 8/2016 |
| EP | 2670352 B1 | 8/2016 |
| EP | 2829235 B1 | 8/2016 |
| EP | 2853238 B1 | 8/2016 |
| EP | 2866738 B1 | 8/2016 |
| EP | 2906150 B1 | 8/2016 |
| EP | 3052053 A1 | 8/2016 |
| EP | 3052611 A1 | 8/2016 |
| EP | 3060171 A1 | 8/2016 |
| EP | 3060174 A1 | 8/2016 |
| EP | 3061421 A1 | 8/2016 |
| EP | 3061422 A1 | 8/2016 |
| EP | 1156755 B1 | 9/2016 |
| EP | 1492478 B1 | 9/2016 |
| EP | 1912697 B1 | 9/2016 |
| EP | 2393449 B1 | 9/2016 |
| EP | 2670356 B1 | 9/2016 |
| EP | 2793969 B1 | 9/2016 |
| EP | 2809271 B1 | 9/2016 |
| EP | 2896425 B1 | 9/2016 |
| EP | 3068345 A1 | 9/2016 |
| EP | 3068346 A1 | 9/2016 |
| EP | 3071148 A1 | 9/2016 |
| EP | 3071149 A1 | 9/2016 |
| EP | 2023858 B1 | 10/2016 |
| EP | 2112912 B1 | 10/2016 |
| EP | 2640319 B1 | 10/2016 |
| EP | 2663257 B1 | 10/2016 |
| EP | 2727612 B1 | 10/2016 |
| EP | 2760384 B1 | 10/2016 |
| EP | 2806829 B1 | 10/2016 |
| EP | 2858599 B1 | 10/2016 |
| EP | 2918250 B1 | 10/2016 |
| EP | 2922592 A4 | 10/2016 |
| EP | 2934387 B1 | 10/2016 |
| EP | 3076901 A1 | 10/2016 |
| EP | 3079633 A1 | 10/2016 |
| EP | 1539047 B1 | 11/2016 |
| EP | 2282700 B1 | 11/2016 |
| EP | 2400926 B1 | 11/2016 |
| EP | 2467104 B1 | 11/2016 |
| EP | 2525743 B1 | 11/2016 |
| EP | 2549953 B1 | 11/2016 |
| EP | 2575696 B1 | 11/2016 |
| EP | 2598045 B1 | 11/2016 |
| EP | 2670355 B1 | 11/2016 |
| EP | 2676640 B1 | 11/2016 |
| EP | 2680792 B1 | 11/2016 |
| EP | 2707053 B1 | 11/2016 |
| EP | 2717803 B1 | 11/2016 |
| EP | 2773297 B1 | 11/2016 |
| EP | 2801387 B1 | 11/2016 |
| EP | 2844192 B1 | 11/2016 |
| EP | 2849679 B1 | 11/2016 |
| EP | 2877122 B1 | 11/2016 |
| EP | 2908778 B1 | 11/2016 |
| EP | 2922500 B1 | 11/2016 |
| EP | 2922501 B1 | 11/2016 |
| EP | 2967854 B1 | 11/2016 |
| EP | 3020365 B1 | 11/2016 |
| EP | 3090703 A1 | 11/2016 |
| EP | 3096713 A1 | 11/2016 |
| EP | 1645244 B1 | 12/2016 |
| EP | 1667614 B1 | 12/2016 |
| EP | 1684656 B1 | 12/2016 |
| EP | 1684670 B1 | 12/2016 |
| EP | 1750592 B1 | 12/2016 |
| EP | 1883375 B1 | 12/2016 |
| EP | 2293739 B1 | 12/2016 |
| EP | 2339988 B1 | 12/2016 |
| EP | 2512375 B1 | 12/2016 |
| EP | 2754417 B1 | 12/2016 |
| EP | 2754418 B1 | 12/2016 |
| EP | 2755562 B1 | 12/2016 |
| EP | 2889019 B1 | 12/2016 |
| EP | 3010442 B1 | 12/2016 |
| EP | 3099271 A1 | 12/2016 |
| EP | 3102150 A1 | 12/2016 |
| EP | 3107495 A1 | 12/2016 |
| EP | 3107498 A2 | 12/2016 |
| EP | 3107500 A1 | 12/2016 |
| EP | 1893127 B1 | 1/2017 |
| EP | 1951352 B1 | 1/2017 |
| EP | 2109419 B1 | 1/2017 |
| EP | 2185107 B1 | 1/2017 |
| EP | 2266503 B1 | 1/2017 |
| EP | 2340055 B1 | 1/2017 |
| EP | 2395941 B1 | 1/2017 |
| EP | 2400923 B1 | 1/2017 |
| EP | 2629699 B1 | 1/2017 |

(56) References Cited

FOREIGN PATENT DOCUMENTS

| | | | |
|---|---|---|---|
| EP | 2645963 | B1 | 1/2017 |
| EP | 2654622 | B1 | 1/2017 |
| EP | 2706952 | B1 | 1/2017 |
| EP | 2760347 | B1 | 1/2017 |
| EP | 2771064 | B1 | 1/2017 |
| EP | 2780077 | B1 | 1/2017 |
| EP | 2809272 | B1 | 1/2017 |
| EP | 2934385 | B1 | 1/2017 |
| EP | 2986255 | B1 | 1/2017 |
| EP | 3119351 | A1 | 1/2017 |
| EP | 1507493 | B1 | 2/2017 |
| EP | 2563238 | B1 | 2/2017 |
| EP | 2752170 | B1 | 2/2017 |
| EP | 2760371 | B1 | 2/2017 |
| EP | 2793709 | B1 | 2/2017 |
| EP | 2793748 | B1 | 2/2017 |
| EP | 2793763 | B1 | 2/2017 |
| EP | 2832317 | B1 | 2/2017 |
| EP | 2921135 | B1 | 2/2017 |
| EP | 2967931 | B1 | 2/2017 |
| EP | 2974693 | B1 | 2/2017 |
| EP | 3025680 | B1 | 2/2017 |
| EP | 3025681 | B1 | 2/2017 |
| EP | 3125826 | A1 | 2/2017 |
| EP | 3125827 | A2 | 2/2017 |
| EP | 3128927 | A1 | 2/2017 |
| EP | 3131502 | A1 | 2/2017 |
| EP | 1845895 | B1 | 3/2017 |
| EP | 2190385 | B1 | 3/2017 |
| EP | 2266504 | B1 | 3/2017 |
| EP | 2341871 | B1 | 3/2017 |
| EP | 2379011 | B1 | 3/2017 |
| EP | 2379013 | B1 | 3/2017 |
| EP | 2640316 | B1 | 3/2017 |
| EP | 2731552 | B1 | 3/2017 |
| EP | 2756109 | B1 | 3/2017 |
| EP | 2773298 | B1 | 3/2017 |
| EP | 2832316 | B1 | 3/2017 |
| EP | 2854718 | B1 | 3/2017 |
| EP | 2881083 | B1 | 3/2017 |
| EP | 2934390 | B1 | 3/2017 |
| EP | 2934391 | B1 | 3/2017 |
| EP | 3010564 | A4 | 3/2017 |
| EP | 3145451 | A2 | 3/2017 |
| EP | 3146938 | A1 | 3/2017 |
| EP | 2014239 | B1 | 4/2017 |
| EP | 2111189 | B1 | 4/2017 |
| EP | 2393451 | B1 | 4/2017 |
| EP | 2617388 | B1 | 4/2017 |
| EP | 2629700 | B1 | 4/2017 |
| EP | 2832318 | B1 | 4/2017 |
| EP | 2893904 | B1 | 4/2017 |
| EP | 2982340 | B1 | 4/2017 |
| EP | 3000436 | B1 | 4/2017 |
| EP | 3001979 | B1 | 4/2017 |
| EP | 3043749 | B1 | 4/2017 |
| EP | 3045147 | B1 | 4/2017 |
| EP | 3054893 | B1 | 4/2017 |
| EP | 3154474 | A1 | 4/2017 |
| EP | 3156007 | A1 | 4/2017 |
| EP | 3157469 | A1 | 4/2017 |
| EP | 3158975 | A1 | 4/2017 |
| EP | 1855614 | B1 | 5/2017 |
| EP | 2001402 | B1 | 5/2017 |
| EP | 2032080 | B1 | 5/2017 |
| EP | 2262451 | B1 | 5/2017 |
| EP | 2470119 | B1 | 5/2017 |
| EP | 2478869 | B1 | 5/2017 |
| EP | 2538880 | B1 | 5/2017 |
| EP | 2545850 | B1 | 5/2017 |
| EP | 2600799 | B1 | 5/2017 |
| EP | 2717926 | B1 | 5/2017 |
| EP | 2726024 | B1 | 5/2017 |
| EP | 2805678 | B1 | 5/2017 |
| EP | 2809270 | B1 | 5/2017 |
| EP | 2918245 | B1 | 5/2017 |
| EP | 2953579 | B1 | 5/2017 |
| EP | 2976043 | B1 | 5/2017 |
| EP | 2979666 | B1 | 5/2017 |
| EP | 3011931 | B1 | 5/2017 |
| EP | 3025682 | B1 | 5/2017 |
| EP | 3033135 | B1 | 5/2017 |
| EP | 3160396 | A1 | 5/2017 |
| EP | 3167847 | A1 | 5/2017 |
| EP | 3169245 | A1 | 5/2017 |
| EP | 3169276 | A1 | 5/2017 |
| EP | 2351541 | B1 | 6/2017 |
| EP | 2384165 | B1 | 6/2017 |
| EP | 2400924 | B1 | 6/2017 |
| EP | 2419041 | B1 | 6/2017 |
| EP | 2419050 | B1 | 6/2017 |
| EP | 2489331 | B1 | 6/2017 |
| EP | 2493417 | B1 | 6/2017 |
| EP | 2560585 | B1 | 6/2017 |
| EP | 2611387 | B1 | 6/2017 |
| EP | 2645967 | B1 | 6/2017 |
| EP | 2677965 | B1 | 6/2017 |
| EP | 2760349 | B1 | 6/2017 |
| EP | 2826443 | B1 | 6/2017 |
| EP | 2906148 | B1 | 6/2017 |
| EP | 2929860 | B1 | 6/2017 |
| EP | 2934669 | B1 | 6/2017 |
| EP | 2967852 | B1 | 6/2017 |
| EP | 3076901 | A4 | 6/2017 |
| EP | 3174502 | A1 | 6/2017 |
| EP | 3175823 | A1 | 6/2017 |
| EP | 3178443 | A1 | 6/2017 |
| EP | 3178445 | A1 | 6/2017 |
| EP | 3184081 | A1 | 6/2017 |
| EP | 1624810 | B1 | 7/2017 |
| EP | 2026703 | B1 | 7/2017 |
| EP | 2293718 | B1 | 7/2017 |
| EP | 2339989 | B1 | 7/2017 |
| EP | 2344076 | B1 | 7/2017 |
| EP | 2486893 | B1 | 7/2017 |
| EP | 2536356 | B1 | 7/2017 |
| EP | 2548534 | B1 | 7/2017 |
| EP | 2608742 | B1 | 7/2017 |
| EP | 2673038 | B1 | 7/2017 |
| EP | 2676638 | B1 | 7/2017 |
| EP | 2774630 | B1 | 7/2017 |
| EP | 2825107 | B1 | 7/2017 |
| EP | 2841020 | B1 | 7/2017 |
| EP | 2934386 | B1 | 7/2017 |
| EP | 2943151 | B1 | 7/2017 |
| EP | 3058894 | B1 | 7/2017 |
| EP | 3071151 | B1 | 7/2017 |
| EP | 3191025 | A1 | 7/2017 |
| EP | 3193740 | A2 | 7/2017 |
| EP | 3193782 | A1 | 7/2017 |
| EP | 1530441 | B1 | 8/2017 |
| EP | 1722716 | B1 | 8/2017 |
| EP | 1971289 | B1 | 8/2017 |
| EP | 2323591 | B1 | 8/2017 |
| EP | 2344070 | B1 | 8/2017 |
| EP | 2393442 | A4 | 8/2017 |
| EP | 2413842 | B1 | 8/2017 |
| EP | 2427143 | B1 | 8/2017 |
| EP | 2459077 | B1 | 8/2017 |
| EP | 2480167 | B1 | 8/2017 |
| EP | 2482749 | B1 | 8/2017 |
| EP | 2496181 | B1 | 8/2017 |
| EP | 2568925 | B1 | 8/2017 |
| EP | 2617389 | B1 | 8/2017 |
| EP | 2713954 | B1 | 8/2017 |
| EP | 2755602 | B1 | 8/2017 |
| EP | 2800602 | B1 | 8/2017 |
| EP | 2809263 | B1 | 8/2017 |
| EP | 2830536 | B1 | 8/2017 |
| EP | 2841009 | B1 | 8/2017 |
| EP | 2844190 | B1 | 8/2017 |
| EP | 2849681 | B1 | 8/2017 |
| EP | 2858600 | B1 | 8/2017 |
| EP | 2897556 | B1 | 8/2017 |

(56) References Cited

FOREIGN PATENT DOCUMENTS

| | | | |
|---|---|---|---|
| EP | 2934388 | B1 | 8/2017 |
| EP | 2979667 | B1 | 8/2017 |
| EP | 3197397 | A1 | 8/2017 |
| EP | 3202371 | A1 | 8/2017 |
| EP | 3206629 | A1 | 8/2017 |
| EP | 3206631 | A2 | 8/2017 |
| EP | 1799093 | B1 | 9/2017 |
| EP | 2010103 | B1 | 9/2017 |
| EP | 2114304 | B1 | 9/2017 |
| EP | 2344090 | B1 | 9/2017 |
| EP | 2398421 | B1 | 9/2017 |
| EP | 2437687 | B1 | 9/2017 |
| EP | 2453970 | B1 | 9/2017 |
| EP | 2509538 | B1 | 9/2017 |
| EP | 2713956 | B1 | 9/2017 |
| EP | 2772227 | B1 | 9/2017 |
| EP | 2787924 | B1 | 9/2017 |
| EP | 2803335 | B1 | 9/2017 |
| EP | 2811939 | B1 | 9/2017 |
| EP | 2830537 | B1 | 9/2017 |
| EP | 2865355 | B1 | 9/2017 |
| EP | 2872047 | B1 | 9/2017 |
| EP | 2934389 | B1 | 9/2017 |
| EP | 3213715 | A1 | 9/2017 |
| EP | 3213716 | A1 | 9/2017 |
| EP | 3215061 | A1 | 9/2017 |
| EP | 3220856 | A2 | 9/2017 |
| EP | 3220857 | A1 | 9/2017 |
| EP | 1945141 | B1 | 10/2017 |
| EP | 2317956 | B1 | 10/2017 |
| EP | 2613737 | B1 | 10/2017 |
| EP | 2620125 | B1 | 10/2017 |
| EP | 2720642 | B1 | 10/2017 |
| EP | 2741682 | B1 | 10/2017 |
| EP | 2872077 | B1 | 10/2017 |
| EP | 3021925 | B1 | 10/2017 |
| EP | 3231395 | A1 | 10/2017 |
| EP | 3232989 | A1 | 10/2017 |
| EP | 1651148 | B1 | 11/2017 |
| EP | 1913901 | B1 | 11/2017 |
| EP | 2222248 | B1 | 11/2017 |
| EP | 2296581 | B1 | 11/2017 |
| EP | 2326264 | B1 | 11/2017 |
| EP | 2427142 | B1 | 11/2017 |
| EP | 2456483 | B1 | 11/2017 |
| EP | 2493423 | B1 | 11/2017 |
| EP | 2611391 | B1 | 11/2017 |
| EP | 2618780 | B1 | 11/2017 |
| EP | 2658480 | B1 | 11/2017 |
| EP | 2710978 | B1 | 11/2017 |
| EP | 2832315 | B1 | 11/2017 |
| EP | 2954875 | B1 | 11/2017 |
| EP | 2967861 | B1 | 11/2017 |
| EP | 2982338 | B1 | 11/2017 |
| EP | 3027144 | B1 | 11/2017 |
| EP | 3043746 | B1 | 11/2017 |
| EP | 3049026 | B1 | 11/2017 |
| EP | 3068311 | B1 | 11/2017 |
| EP | 3110368 | B1 | 11/2017 |
| EP | 3110369 | B1 | 11/2017 |
| EP | 3132773 | B1 | 11/2017 |
| EP | 3238662 | A1 | 11/2017 |
| EP | 3245980 | A1 | 11/2017 |
| EP | 3247312 | A1 | 11/2017 |
| EP | 1667603 | B1 | 12/2017 |
| EP | 1874954 | B1 | 12/2017 |
| EP | 2427145 | B1 | 12/2017 |
| EP | 2542185 | B1 | 12/2017 |
| EP | 2670351 | A4 | 12/2017 |
| EP | 2723274 | B1 | 12/2017 |
| EP | 2736455 | B1 | 12/2017 |
| EP | 2736457 | B1 | 12/2017 |
| EP | 2830534 | B1 | 12/2017 |
| EP | 2830535 | B1 | 12/2017 |
| EP | 2911592 | B1 | 12/2017 |
| EP | 2916772 | B1 | 12/2017 |
| EP | 2967922 | B1 | 12/2017 |
| EP | 3009105 | B1 | 12/2017 |
| EP | 3088037 | B1 | 12/2017 |
| EP | 3115023 | B1 | 12/2017 |
| EP | 3251633 | A1 | 12/2017 |
| EP | 3256074 | A1 | 12/2017 |
| EP | 3256076 | A1 | 12/2017 |
| EP | 3256178 | A1 | 12/2017 |
| EP | 1492458 | B1 | 1/2018 |
| EP | 1768604 | B1 | 1/2018 |
| EP | 1951154 | B1 | 1/2018 |
| EP | 2091465 | B1 | 1/2018 |
| EP | 2345380 | B1 | 1/2018 |
| EP | 2456363 | B1 | 1/2018 |
| EP | 2531143 | B1 | 1/2018 |
| EP | 2621407 | B1 | 1/2018 |
| EP | 2694123 | B1 | 1/2018 |
| EP | 2775962 | B1 | 1/2018 |
| EP | 2874568 | B1 | 1/2018 |
| EP | 2967863 | B1 | 1/2018 |
| EP | 2967869 | B1 | 1/2018 |
| EP | 3033047 | B1 | 1/2018 |
| EP | 3037065 | B1 | 1/2018 |
| EP | 3049025 | B1 | 1/2018 |
| EP | 3052052 | B1 | 1/2018 |
| EP | 3078350 | B1 | 1/2018 |
| EP | 3266417 | A1 | 1/2018 |
| EP | 3267946 | A1 | 1/2018 |
| EP | 3269331 | A1 | 1/2018 |
| EP | 3273911 | A1 | 1/2018 |
| EP | 3275404 | A1 | 1/2018 |
| EP | 2197512 | B1 | 2/2018 |
| EP | 2248486 | B1 | 2/2018 |
| EP | 2344066 | B1 | 2/2018 |
| EP | 2381854 | B1 | 2/2018 |
| EP | 2667823 | B1 | 2/2018 |
| EP | 2699169 | B1 | 2/2018 |
| EP | 2714177 | B1 | 2/2018 |
| EP | 2736544 | B1 | 2/2018 |
| EP | 2846736 | B1 | 2/2018 |
| EP | 2886082 | B1 | 2/2018 |
| EP | 2886084 | B1 | 2/2018 |
| EP | 2931178 | B1 | 2/2018 |
| EP | 2934392 | B1 | 2/2018 |
| EP | 3150173 | B1 | 2/2018 |
| EP | 3277221 | A1 | 2/2018 |
| EP | 3277222 | A1 | 2/2018 |
| EP | 3280358 | A1 | 2/2018 |
| EP | 3281608 | A1 | 2/2018 |
| EP | 3283011 | A1 | 2/2018 |
| EP | 3287099 | A1 | 2/2018 |
| EP | 1959864 | B1 | 3/2018 |
| EP | 2513200 | B1 | 3/2018 |
| EP | 2608815 | B1 | 3/2018 |
| EP | 2858711 | B1 | 3/2018 |
| EP | 2938292 | B1 | 3/2018 |
| EP | 2943132 | B1 | 3/2018 |
| EP | 2983620 | B1 | 3/2018 |
| EP | 3003219 | B1 | 3/2018 |
| EP | 3005979 | B1 | 3/2018 |
| EP | 3037064 | B1 | 3/2018 |
| EP | 3046511 | B1 | 3/2018 |
| EP | 3142603 | B1 | 3/2018 |
| EP | 3288479 | A1 | 3/2018 |
| EP | 3288491 | A1 | 3/2018 |
| EP | 3288494 | A1 | 3/2018 |
| EP | 3288497 | A2 | 3/2018 |
| EP | 3288498 | A1 | 3/2018 |
| EP | 3288499 | A1 | 3/2018 |
| EP | 3290004 | A1 | 3/2018 |
| EP | 3290007 | A1 | 3/2018 |
| EP | 3294214 | A1 | 3/2018 |
| EP | 3294215 | A1 | 3/2018 |
| EP | 3294218 | A1 | 3/2018 |
| EP | 3296979 | A1 | 3/2018 |
| EP | 3298970 | A1 | 3/2018 |
| EP | 3298987 | A1 | 3/2018 |
| EP | 3298988 | A1 | 3/2018 |

(56) References Cited

FOREIGN PATENT DOCUMENTS

| | | | |
|---|---|---|---|
| EP | 2209440 | B1 | 4/2018 |
| EP | 2536357 | B1 | 4/2018 |
| EP | 2605725 | B1 | 4/2018 |
| EP | 2608743 | B1 | 4/2018 |
| EP | 2709561 | B1 | 4/2018 |
| EP | 2787925 | B1 | 4/2018 |
| EP | 2789314 | B1 | 4/2018 |
| EP | 2900150 | B1 | 4/2018 |
| EP | 2908779 | B1 | 4/2018 |
| EP | 2922502 | B1 | 4/2018 |
| EP | 2964441 | B1 | 4/2018 |
| EP | 2967868 | B1 | 4/2018 |
| EP | 2979665 | B1 | 4/2018 |
| EP | 2994073 | B1 | 4/2018 |
| EP | 3095394 | B1 | 4/2018 |
| EP | 3128927 | A4 | 4/2018 |
| EP | 3134033 | B1 | 4/2018 |
| EP | 3137146 | A4 | 4/2018 |
| EP | 3280482 | A4 | 4/2018 |
| EP | 3302362 | A1 | 4/2018 |
| EP | 3302367 | A1 | 4/2018 |
| EP | 3307208 | A1 | 4/2018 |
| EP | 3308745 | A1 | 4/2018 |
| EP | 3310301 | A1 | 4/2018 |
| EP | 3311775 | A1 | 4/2018 |
| EP | 1945112 | B1 | 5/2018 |
| EP | 2007313 | B1 | 5/2018 |
| EP | 2316381 | B2 | 5/2018 |
| EP | 2377469 | B1 | 5/2018 |
| EP | 2531115 | B1 | 5/2018 |
| EP | 2561831 | B1 | 5/2018 |
| EP | 2605724 | B1 | 5/2018 |
| EP | 2723277 | B1 | 5/2018 |
| EP | 2741711 | B1 | 5/2018 |
| EP | 2755573 | B1 | 5/2018 |
| EP | 2768429 | B1 | 5/2018 |
| EP | 2819618 | B1 | 5/2018 |
| EP | 2833836 | B1 | 5/2018 |
| EP | 2886083 | B1 | 5/2018 |
| EP | 2926840 | B1 | 5/2018 |
| EP | 2943157 | B1 | 5/2018 |
| EP | 2948099 | B1 | 5/2018 |
| EP | 3000437 | B1 | 5/2018 |
| EP | 3145448 | B1 | 5/2018 |
| EP | 3154475 | B1 | 5/2018 |
| EP | 3316819 | A1 | 5/2018 |
| EP | 3316821 | A1 | 5/2018 |
| EP | 3322381 | A1 | 5/2018 |
| EP | 3322383 | A1 | 5/2018 |
| EP | 3323353 | A1 | 5/2018 |
| EP | 3323439 | A1 | 5/2018 |
| EP | 3324892 | A1 | 5/2018 |
| EP | 3326584 | A1 | 5/2018 |
| EP | 2150312 | B1 | 6/2018 |
| EP | 2379322 | B1 | 6/2018 |
| EP | 2400925 | B1 | 6/2018 |
| EP | 2552355 | B1 | 6/2018 |
| EP | 2560589 | B1 | 6/2018 |
| EP | 2563277 | B1 | 6/2018 |
| EP | 2661305 | B1 | 6/2018 |
| EP | 2736456 | B1 | 6/2018 |
| EP | 2782523 | B1 | 6/2018 |
| EP | 3056170 | B1 | 6/2018 |
| EP | 3062745 | B1 | 6/2018 |
| EP | 3130320 | B1 | 6/2018 |
| EP | 3187150 | B1 | 6/2018 |
| EP | 3334378 | A1 | 6/2018 |
| EP | 3334380 | A1 | 6/2018 |
| EP | 3334381 | A1 | 6/2018 |
| EP | 3337412 | A1 | 6/2018 |
| EP | 3337424 | A1 | 6/2018 |
| EP | 2478872 | B1 | 7/2018 |
| EP | 2563278 | B1 | 7/2018 |
| EP | 2616004 | B1 | 7/2018 |
| EP | 2779943 | B1 | 7/2018 |
| EP | 2802290 | B1 | 7/2018 |
| EP | 2816980 | B1 | 7/2018 |
| EP | 2938293 | B1 | 7/2018 |
| EP | 3107496 | B1 | 7/2018 |
| EP | 3178450 | B1 | 7/2018 |
| EP | 3212097 | B1 | 7/2018 |
| EP | 3340923 | A1 | 7/2018 |
| EP | 3340932 | A1 | 7/2018 |
| EP | 3340934 | A1 | 7/2018 |
| EP | 3340936 | A1 | 7/2018 |
| EP | 3340945 | A1 | 7/2018 |
| EP | 3342355 | A1 | 7/2018 |
| EP | 3342377 | A1 | 7/2018 |
| EP | 3344158 | A1 | 7/2018 |
| EP | 3346952 | A1 | 7/2018 |
| EP | 3347182 | A1 | 7/2018 |
| EP | 3348235 | A1 | 7/2018 |
| EP | 2536354 | B1 | 8/2018 |
| EP | 2616006 | B1 | 8/2018 |
| EP | 2797556 | B1 | 8/2018 |
| EP | 2822473 | B1 | 8/2018 |
| EP | 2854711 | B1 | 8/2018 |
| EP | 2866847 | B1 | 8/2018 |
| EP | 2918246 | B1 | 8/2018 |
| EP | 2967845 | B1 | 8/2018 |
| EP | 2999436 | B1 | 8/2018 |
| EP | 3013281 | B1 | 8/2018 |
| EP | 3060170 | B1 | 8/2018 |
| EP | 3104811 | B1 | 8/2018 |
| EP | 3143944 | B1 | 8/2018 |
| EP | 3157467 | B1 | 8/2018 |
| EP | 3193791 | B1 | 8/2018 |
| EP | 3241526 | B1 | 8/2018 |
| EP | 3355800 | A1 | 8/2018 |
| EP | 3360513 | A1 | 8/2018 |
| EP | 3360514 | A1 | 8/2018 |
| EP | 3361988 | A1 | 8/2018 |
| EP | 3361991 | A1 | 8/2018 |
| EP | 2114305 | B1 | 9/2018 |
| EP | 2155115 | B1 | 9/2018 |
| EP | 2601910 | B1 | 9/2018 |
| EP | 2617390 | B1 | 9/2018 |
| EP | 2734157 | B1 | 9/2018 |
| EP | 2968674 | B1 | 9/2018 |
| EP | 2999415 | B1 | 9/2018 |
| EP | 3106130 | B1 | 9/2018 |
| EP | 3151763 | B1 | 9/2018 |
| EP | 3213717 | B1 | 9/2018 |
| EP | 3245985 | B1 | 9/2018 |
| EP | 3367979 | A1 | 9/2018 |
| EP | 3370649 | A1 | 9/2018 |
| EP | 3370650 | A1 | 9/2018 |
| EP | 3377000 | A1 | 9/2018 |
| EP | 1827256 | B1 | 10/2018 |
| EP | 1850790 | B1 | 10/2018 |
| EP | 2063823 | B1 | 10/2018 |
| EP | 2124825 | B1 | 10/2018 |
| EP | 2249746 | B1 | 10/2018 |
| EP | 2254514 | B1 | 10/2018 |
| EP | 2285309 | B1 | 10/2018 |
| EP | 2455042 | B1 | 10/2018 |
| EP | 2571561 | B1 | 10/2018 |
| EP | 2616008 | B1 | 10/2018 |
| EP | 2647393 | B1 | 10/2018 |
| EP | 2739214 | B1 | 10/2018 |
| EP | 2739247 | B1 | 10/2018 |
| EP | 2776114 | B1 | 10/2018 |
| EP | 2836171 | B1 | 10/2018 |
| EP | 2842581 | B1 | 10/2018 |
| EP | 2870946 | B1 | 10/2018 |
| EP | 2923665 | B1 | 10/2018 |
| EP | 2964277 | B1 | 10/2018 |
| EP | 3001978 | B1 | 10/2018 |
| EP | 3010562 | B1 | 10/2018 |
| EP | 3072475 | B1 | 10/2018 |
| EP | 3081161 | B1 | 10/2018 |
| EP | 3081195 | B1 | 10/2018 |
| EP | 3099345 | B1 | 10/2018 |
| EP | 3120809 | B1 | 10/2018 |

(56) References Cited

FOREIGN PATENT DOCUMENTS

| | | | |
|---|---|---|---|
| EP | 3238663 | B1 | 10/2018 |
| EP | 3275404 | A4 | 10/2018 |
| EP | 3384879 | A1 | 10/2018 |
| EP | 3388027 | A1 | 10/2018 |
| EP | 3389557 | A1 | 10/2018 |
| EP | 3390706 | A1 | 10/2018 |
| EP | 1708650 | B1 | 11/2018 |
| EP | 1945143 | B1 | 11/2018 |
| EP | 2205183 | B1 | 11/2018 |
| EP | 2663258 | B1 | 11/2018 |
| EP | 2790615 | B1 | 11/2018 |
| EP | 2854709 | B1 | 11/2018 |
| EP | 2898859 | B1 | 11/2018 |
| EP | 2921139 | B1 | 11/2018 |
| EP | 2928538 | B1 | 11/2018 |
| EP | 3075354 | B1 | 11/2018 |
| EP | 3082949 | B1 | 11/2018 |
| EP | 3145452 | B1 | 11/2018 |
| EP | 3216424 | B1 | 11/2018 |
| EP | 3260084 | B1 | 11/2018 |
| EP | 3397206 | A1 | 11/2018 |
| EP | 3398562 | A1 | 11/2018 |
| EP | 3400908 | A1 | 11/2018 |
| EP | 3403616 | A1 | 11/2018 |
| EP | 3405139 | A1 | 11/2018 |
| EP | 1858450 | B1 | 12/2018 |
| EP | 2150208 | B1 | 12/2018 |
| EP | 2326261 | B1 | 12/2018 |
| EP | 2344075 | B1 | 12/2018 |
| EP | 2370028 | B1 | 12/2018 |
| EP | 2555709 | B1 | 12/2018 |
| EP | 2564812 | B1 | 12/2018 |
| EP | 2777618 | B1 | 12/2018 |
| EP | 2814427 | B1 | 12/2018 |
| EP | 2829240 | B1 | 12/2018 |
| EP | 2911594 | B1 | 12/2018 |
| EP | 2911729 | B1 | 12/2018 |
| EP | 2954876 | B1 | 12/2018 |
| EP | 2958520 | B1 | 12/2018 |
| EP | 2958605 | B1 | 12/2018 |
| EP | 3010446 | B1 | 12/2018 |
| EP | 3064174 | B1 | 12/2018 |
| EP | 3206628 | B1 | 12/2018 |
| EP | 3242629 | B1 | 12/2018 |
| EP | 3260085 | B1 | 12/2018 |
| EP | 3266416 | B1 | 12/2018 |
| EP | 3326583 | B1 | 12/2018 |
| EP | 3407834 | A1 | 12/2018 |
| EP | 3410984 | A1 | 12/2018 |
| EP | 3410987 | A1 | 12/2018 |
| EP | 3415120 | A1 | 12/2018 |
| EP | 3417813 | A1 | 12/2018 |
| EP | 2129332 | B1 | 1/2019 |
| EP | 2196159 | B1 | 1/2019 |
| EP | 2370025 | B1 | 1/2019 |
| EP | 2549957 | B1 | 1/2019 |
| EP | 2819619 | B1 | 1/2019 |
| EP | 2849680 | B1 | 1/2019 |
| EP | 2856972 | B1 | 1/2019 |
| EP | 2866742 | B1 | 1/2019 |
| EP | 2884946 | B1 | 1/2019 |
| EP | 2948102 | B1 | 1/2019 |
| EP | 2979664 | B1 | 1/2019 |
| EP | 3043748 | B1 | 1/2019 |
| EP | 3145449 | B1 | 1/2019 |
| EP | 3288491 | A4 | 1/2019 |
| EP | 3332743 | B1 | 1/2019 |
| EP | 3427695 | A1 | 1/2019 |
| EP | 3429507 | A1 | 1/2019 |
| EP | 3432832 | A1 | 1/2019 |
| EP | 3432834 | A1 | 1/2019 |
| EP | 1895943 | B1 | 2/2019 |
| EP | 2070490 | B1 | 2/2019 |
| EP | 2308425 | B1 | 2/2019 |
| EP | 2379009 | B1 | 2/2019 |
| EP | 2575685 | B1 | 2/2019 |
| EP | 2688562 | B1 | 2/2019 |
| EP | 2714068 | B1 | 2/2019 |
| EP | 2720641 | B1 | 2/2019 |
| EP | 2760375 | B1 | 2/2019 |
| EP | 2862590 | B1 | 2/2019 |
| EP | 2925259 | B1 | 2/2019 |
| EP | 2931179 | B1 | 2/2019 |
| EP | 3005983 | B1 | 2/2019 |
| EP | 3023117 | B1 | 2/2019 |
| EP | 3184083 | B1 | 2/2019 |
| EP | 3202333 | B1 | 2/2019 |
| EP | 3261583 | B1 | 2/2019 |
| EP | 3278832 | B1 | 2/2019 |
| EP | 3409454 | A4 | 2/2019 |
| EP | 3435919 | A1 | 2/2019 |
| EP | 3441045 | A1 | 2/2019 |
| EP | 3442469 | A1 | 2/2019 |
| EP | 3443937 | A1 | 2/2019 |
| EP | 1771132 | B1 | 3/2019 |
| EP | 1959866 | B1 | 3/2019 |
| EP | 2120794 | B1 | 3/2019 |
| EP | 2259728 | B1 | 3/2019 |
| EP | 2344074 | B1 | 3/2019 |
| EP | 2552356 | B1 | 3/2019 |
| EP | 2598044 | B1 | 3/2019 |
| EP | 2659861 | B1 | 3/2019 |
| EP | 2670357 | B1 | 3/2019 |
| EP | 2898902 | B1 | 3/2019 |
| EP | 2948098 | B1 | 3/2019 |
| EP | 2948101 | B1 | 3/2019 |
| EP | 2967865 | B1 | 3/2019 |
| EP | 2974695 | B1 | 3/2019 |
| EP | 3027243 | B1 | 3/2019 |
| EP | 3116446 | B1 | 3/2019 |
| EP | 3145445 | B1 | 3/2019 |
| EP | 3151783 | B1 | 3/2019 |
| EP | 3151784 | B1 | 3/2019 |
| EP | 3278768 | B1 | 3/2019 |
| EP | 3320943 | B1 | 3/2019 |
| EP | 3448314 | A1 | 3/2019 |
| EP | 3448315 | A1 | 3/2019 |
| EP | 3449969 | A1 | 3/2019 |
| EP | 3454785 | A1 | 3/2019 |
| EP | 3454786 | A1 | 3/2019 |
| EP | 3454789 | A1 | 3/2019 |
| EP | 3454794 | A1 | 3/2019 |
| EP | 3454795 | A1 | 3/2019 |
| EP | 3457987 | A1 | 3/2019 |
| EP | 3457988 | A1 | 3/2019 |
| EP | 3457990 | A1 | 3/2019 |
| EP | 3458136 | A2 | 3/2019 |
| EP | 3459499 | A2 | 3/2019 |
| EP | 1793745 | B1 | 4/2019 |
| EP | 1855623 | B1 | 4/2019 |
| EP | 2129333 | B1 | 4/2019 |
| EP | 2149349 | B1 | 4/2019 |
| EP | 2438888 | B1 | 4/2019 |
| EP | 2484309 | B1 | 4/2019 |
| EP | 2519268 | B1 | 4/2019 |
| EP | 2528545 | B1 | 4/2019 |
| EP | 2536358 | B1 | 4/2019 |
| EP | 2661239 | B1 | 4/2019 |
| EP | 2709563 | B1 | 4/2019 |
| EP | 2736451 | B1 | 4/2019 |
| EP | 2810619 | B1 | 4/2019 |
| EP | 2810622 | B1 | 4/2019 |
| EP | 2879589 | B1 | 4/2019 |
| EP | 2921198 | B1 | 4/2019 |
| EP | 2986256 | B1 | 4/2019 |
| EP | 3090704 | B1 | 4/2019 |
| EP | 3116445 | B1 | 4/2019 |
| EP | 3141217 | B1 | 4/2019 |
| EP | 3193745 | B1 | 4/2019 |
| EP | 3241525 | B1 | 4/2019 |
| EP | 3344167 | A4 | 4/2019 |
| EP | 3461531 | A1 | 4/2019 |
| EP | 3463120 | A1 | 4/2019 |
| EP | 3466373 | A1 | 4/2019 |

(56) References Cited

FOREIGN PATENT DOCUMENTS

| | | | |
|---|---|---|---|
| EP | 3471662 | A1 | 4/2019 |
| EP | 1703870 | B1 | 5/2019 |
| EP | 1708642 | B1 | 5/2019 |
| EP | 2240121 | B1 | 5/2019 |
| EP | 2663259 | B1 | 5/2019 |
| EP | 2695586 | B1 | 5/2019 |
| EP | 2726018 | B1 | 5/2019 |
| EP | 2954872 | B1 | 5/2019 |
| EP | 3071150 | B1 | 5/2019 |
| EP | 3110370 | B1 | 5/2019 |
| EP | 3111890 | B1 | 5/2019 |
| EP | 3182932 | B1 | 5/2019 |
| EP | 3192472 | B1 | 5/2019 |
| EP | 3238661 | B1 | 5/2019 |
| EP | 3284503 | B1 | 5/2019 |
| EP | 3302364 | B1 | 5/2019 |
| EP | 3315094 | B1 | 5/2019 |
| EP | 3316818 | B1 | 5/2019 |
| EP | 3474778 | A1 | 5/2019 |
| EP | 3476366 | A1 | 5/2019 |
| EP | 3476424 | A1 | 5/2019 |
| EP | 3478224 | A1 | 5/2019 |
| EP | 3479797 | A1 | 5/2019 |
| EP | 3481335 | A1 | 5/2019 |
| EP | 3481336 | A1 | 5/2019 |
| EP | 3481338 | A1 | 5/2019 |
| EP | 3481339 | A1 | 5/2019 |
| EP | 3482718 | A1 | 5/2019 |
| EP | 3484412 | A1 | 5/2019 |
| EP | 3485847 | A1 | 5/2019 |
| EP | 3485848 | A1 | 5/2019 |
| EP | 3485933 | A1 | 5/2019 |
| EP | 3487420 | A1 | 5/2019 |
| EP | 3487452 | A1 | 5/2019 |
| EP | 3488822 | A1 | 5/2019 |
| EP | 1624792 | B1 | 6/2019 |
| EP | 1737394 | B1 | 6/2019 |
| EP | 1858451 | B1 | 6/2019 |
| EP | 1895944 | B1 | 6/2019 |
| EP | 1968487 | B1 | 6/2019 |
| EP | 2004095 | B1 | 6/2019 |
| EP | 2010102 | B1 | 6/2019 |
| EP | 2131788 | B1 | 6/2019 |
| EP | 2560580 | B1 | 6/2019 |
| EP | 2618782 | B1 | 6/2019 |
| EP | 2868296 | B1 | 6/2019 |
| EP | 2961358 | B1 | 6/2019 |
| EP | 2967847 | B1 | 6/2019 |
| EP | 2985006 | B1 | 6/2019 |
| EP | 3033048 | B1 | 6/2019 |
| EP | 3119451 | B1 | 6/2019 |
| EP | 3131503 | B1 | 6/2019 |
| EP | 3213718 | B1 | 6/2019 |
| EP | 3275390 | B1 | 6/2019 |
| EP | 3300692 | B1 | 6/2019 |
| EP | 3326585 | B1 | 6/2019 |
| EP | 3338737 | B1 | 6/2019 |
| EP | 3357457 | B1 | 6/2019 |
| EP | 3372198 | B1 | 6/2019 |
| EP | 3490465 | A1 | 6/2019 |
| EP | 3490500 | A1 | 6/2019 |
| EP | 3490657 | A1 | 6/2019 |
| EP | 3490659 | A1 | 6/2019 |
| EP | 3496626 | A1 | 6/2019 |
| EP | 3496664 | A1 | 6/2019 |
| EP | 3498224 | A1 | 6/2019 |
| EP | 3501454 | A1 | 6/2019 |
| EP | 1659981 | B1 | 7/2019 |
| EP | 1924223 | B1 | 7/2019 |
| EP | 2249745 | B1 | 7/2019 |
| EP | 2296744 | B1 | 7/2019 |
| EP | 2331019 | B1 | 7/2019 |
| EP | 2368527 | B1 | 7/2019 |
| EP | 2509542 | B1 | 7/2019 |
| EP | 2555710 | B1 | 7/2019 |
| EP | 2575682 | B1 | 7/2019 |
| EP | 2575683 | B1 | 7/2019 |
| EP | 2640431 | B1 | 7/2019 |
| EP | 2641572 | B1 | 7/2019 |
| EP | 2649964 | B1 | 7/2019 |
| EP | 2767260 | B1 | 7/2019 |
| EP | 2777615 | B1 | 7/2019 |
| EP | 2838476 | B1 | 7/2019 |
| EP | 2861186 | B1 | 7/2019 |
| EP | 2877124 | B1 | 7/2019 |
| EP | 2877132 | B1 | 7/2019 |
| EP | 2921565 | B1 | 7/2019 |
| EP | 2938291 | B1 | 7/2019 |
| EP | 2999433 | B1 | 7/2019 |
| EP | 3145450 | B1 | 7/2019 |
| EP | 3254644 | B1 | 7/2019 |
| EP | 3315093 | B1 | 7/2019 |
| EP | 3344189 | B1 | 7/2019 |
| EP | 3503813 | A1 | 7/2019 |
| EP | 3503846 | A1 | 7/2019 |
| EP | 3503847 | A1 | 7/2019 |
| EP | 3503848 | A1 | 7/2019 |
| EP | 3505077 | A1 | 7/2019 |
| EP | 3512465 | A1 | 7/2019 |
| EP | 3515365 | A1 | 7/2019 |
| EP | 3517075 | A1 | 7/2019 |
| EP | 1861043 | B1 | 8/2019 |
| EP | 2303190 | B1 | 8/2019 |
| EP | 2593171 | B1 | 8/2019 |
| EP | 2632393 | B1 | 8/2019 |
| EP | 2663355 | B1 | 8/2019 |
| EP | 2665509 | B1 | 8/2019 |
| EP | 2688525 | B1 | 8/2019 |
| EP | 2699201 | B1 | 8/2019 |
| EP | 2755564 | B1 | 8/2019 |
| EP | 2769681 | B1 | 8/2019 |
| EP | 2793751 | B1 | 8/2019 |
| EP | 2900177 | B1 | 8/2019 |
| EP | 2967536 | B1 | 8/2019 |
| EP | 3050541 | B1 | 8/2019 |
| EP | 3102152 | B1 | 8/2019 |
| EP | 3157607 | B1 | 8/2019 |
| EP | 3231392 | B1 | 8/2019 |
| EP | 3284411 | B1 | 8/2019 |
| EP | 3328318 | B1 | 8/2019 |
| EP | 3348233 | B1 | 8/2019 |
| EP | 3366262 | B1 | 8/2019 |
| EP | 3527170 | A1 | 8/2019 |
| EP | 3530236 | A1 | 8/2019 |
| EP | 2358297 | B1 | 9/2019 |
| EP | 2368525 | B1 | 9/2019 |
| EP | 2542186 | B1 | 9/2019 |
| EP | 2656863 | B1 | 9/2019 |
| EP | 3003221 | B1 | 9/2019 |
| EP | 3003452 | B1 | 9/2019 |
| EP | 3220971 | B1 | 9/2019 |
| EP | 3223874 | B1 | 9/2019 |
| EP | 3288495 | B1 | 9/2019 |
| EP | 3311776 | B1 | 9/2019 |
| EP | 3334379 | B1 | 9/2019 |
| EP | 3531975 | A1 | 9/2019 |
| EP | 3534840 | A1 | 9/2019 |
| EP | 3534841 | A1 | 9/2019 |
| EP | 3534845 | A2 | 9/2019 |
| EP | 3535010 | A1 | 9/2019 |
| EP | 3538026 | A1 | 9/2019 |
| EP | 3538027 | A1 | 9/2019 |
| EP | 3539508 | A1 | 9/2019 |
| EP | 3539509 | A1 | 9/2019 |
| EP | 3541316 | A1 | 9/2019 |
| EP | 3541325 | A1 | 9/2019 |
| EP | 3541328 | A1 | 9/2019 |
| EP | 3542758 | A1 | 9/2019 |
| EP | 1740265 | B1 | 10/2019 |
| EP | 2039756 | B1 | 10/2019 |
| EP | 2456506 | B1 | 10/2019 |
| EP | 2470122 | B1 | 10/2019 |
| EP | 2613738 | B1 | 10/2019 |
| EP | 2637607 | B1 | 10/2019 |

(56) References Cited

FOREIGN PATENT DOCUMENTS

| | | | |
|---|---|---|---|
| EP | 2674174 B1 | 10/2019 |
| EP | 2811923 B1 | 10/2019 |
| EP | 2901967 B1 | 10/2019 |
| EP | 3010431 B1 | 10/2019 |
| EP | 3019091 B1 | 10/2019 |
| EP | 3019123 B1 | 10/2019 |
| EP | 3057522 B1 | 10/2019 |
| EP | 3067075 B1 | 10/2019 |
| EP | 3146937 B1 | 10/2019 |
| EP | 3238777 B1 | 10/2019 |
| EP | 3359211 B1 | 10/2019 |
| EP | 3388026 B1 | 10/2019 |
| EP | 3432806 B1 | 10/2019 |
| EP | 3496626 A4 | 10/2019 |
| EP | 3544548 A1 | 10/2019 |
| EP | 3545905 A1 | 10/2019 |
| EP | 3547936 A1 | 10/2019 |
| EP | 3547966 A1 | 10/2019 |
| EP | 3549555 A1 | 10/2019 |
| EP | 3549556 A1 | 10/2019 |
| EP | 3552585 A1 | 10/2019 |
| EP | 3554424 A1 | 10/2019 |
| EP | 3556323 A1 | 10/2019 |
| EP | 3558165 A1 | 10/2019 |
| EP | 3558168 A1 | 10/2019 |
| EP | 3558169 A2 | 10/2019 |
| EP | 2043559 B1 | 11/2019 |
| EP | 2358308 B1 | 11/2019 |
| EP | 2405863 B1 | 11/2019 |
| EP | 2701633 B1 | 11/2019 |
| EP | 2898857 B1 | 11/2019 |
| EP | 2967853 B1 | 11/2019 |
| EP | 3009104 B1 | 11/2019 |
| EP | 3021792 B1 | 11/2019 |
| EP | 3076900 B1 | 11/2019 |
| EP | 3111889 B1 | 11/2019 |
| EP | 3142607 B1 | 11/2019 |
| EP | 3167850 B1 | 11/2019 |
| EP | 3397205 B1 | 11/2019 |
| EP | 3563799 A1 | 11/2019 |
| EP | 3563806 A1 | 11/2019 |
| EP | 3570779 A1 | 11/2019 |
| EP | 3572045 A1 | 11/2019 |
| EP | 3572117 A1 | 11/2019 |
| EP | 3479800 A4 | 12/2019 |
| EP | 3576677 A1 | 12/2019 |
| EP | 3579761 A2 | 12/2019 |
| EP | 3579788 A1 | 12/2019 |
| EP | 3582697 A1 | 12/2019 |
| EP | 3583922 A1 | 12/2019 |
| EP | 3445443 A4 | 1/2020 |
| EP | 3590471 A1 | 1/2020 |
| EP | 3590472 A1 | 1/2020 |
| EP | 3592284 A1 | 1/2020 |
| EP | 3592288 A1 | 1/2020 |
| EP | 3592289 A1 | 1/2020 |
| EP | 3593763 A1 | 1/2020 |
| EP | 3595588 A1 | 1/2020 |
| EP | 3600156 A1 | 2/2020 |
| EP | 3600159 A1 | 2/2020 |
| EP | 3606443 A1 | 2/2020 |
| EP | 3606472 A1 | 2/2020 |
| EP | 2241287 B2 | 3/2020 |
| EP | 2376013 B1 | 3/2020 |
| EP | 2911593 B1 | 3/2020 |
| EP | 2995279 B1 | 3/2020 |
| EP | 3009103 B1 | 3/2020 |
| EP | 3038664 B1 | 3/2020 |
| EP | 3167848 B1 | 3/2020 |
| EP | 3175822 B1 | 3/2020 |
| EP | 3179960 B1 | 3/2020 |
| EP | 3280479 B1 | 3/2020 |
| EP | 3616651 A1 | 3/2020 |
| EP | 3619136 A1 | 3/2020 |
| EP | 3626208 A1 | 3/2020 |
| EP | 1667614 B2 | 4/2020 |
| EP | 2119417 B2 | 4/2020 |
| EP | 2155114 B1 | 4/2020 |
| EP | 2299937 B1 | 4/2020 |
| EP | 2331016 B1 | 4/2020 |
| EP | 2376013 B8 | 4/2020 |
| EP | 2413843 B1 | 4/2020 |
| EP | 2854705 B1 | 4/2020 |
| EP | 2918249 B1 | 4/2020 |
| EP | 2922593 B1 | 4/2020 |
| EP | 2950753 B1 | 4/2020 |
| EP | 2967810 B1 | 4/2020 |
| EP | 3110367 B1 | 4/2020 |
| EP | 3111888 B1 | 4/2020 |
| EP | 3128927 B1 | 4/2020 |
| EP | 3134032 B1 | 4/2020 |
| EP | 3142606 B1 | 4/2020 |
| EP | 3270825 B1 | 4/2020 |
| EP | 3300696 B1 | 4/2020 |
| EP | 3316823 B1 | 4/2020 |
| EP | 3334487 B1 | 4/2020 |
| EP | 3342355 B1 | 4/2020 |
| EP | 3373863 B1 | 4/2020 |
| EP | 3459498 B1 | 4/2020 |
| EP | 3470105 B1 | 4/2020 |
| EP | 3628274 A1 | 4/2020 |
| EP | 3632338 A1 | 4/2020 |
| EP | 3636312 A1 | 4/2020 |
| EP | 3639792 A1 | 4/2020 |
| EP | 3639888 A1 | 4/2020 |
| EP | 3643273 A1 | 4/2020 |
| EP | 1895942 B1 | 5/2020 |
| EP | 2120821 B1 | 5/2020 |
| EP | 2437688 B1 | 5/2020 |
| EP | 2785281 B1 | 5/2020 |
| EP | 2852354 B1 | 5/2020 |
| EP | 2884906 B1 | 5/2020 |
| EP | 2999412 B1 | 5/2020 |
| EP | 3060174 B1 | 5/2020 |
| EP | 3071147 B1 | 5/2020 |
| EP | 3104812 B1 | 5/2020 |
| EP | 3139861 B1 | 5/2020 |
| EP | 3232989 B1 | 5/2020 |
| EP | 3294219 B1 | 5/2020 |
| EP | 3298970 B1 | 5/2020 |
| EP | 3302366 B1 | 5/2020 |
| EP | 3323389 B1 | 5/2020 |
| EP | 3332744 B1 | 5/2020 |
| EP | 3402440 B1 | 5/2020 |
| EP | 3417813 B1 | 5/2020 |
| EP | 3417831 B1 | 5/2020 |
| EP | 3457987 B1 | 5/2020 |
| EP | 3484413 B1 | 5/2020 |
| EP | 3531975 B1 | 5/2020 |
| EP | 3644866 A1 | 5/2020 |
| EP | 3646822 A1 | 5/2020 |
| EP | 3646824 A1 | 5/2020 |
| EP | 3646825 A1 | 5/2020 |
| EP | 3648706 A1 | 5/2020 |
| EP | 3648709 A1 | 5/2020 |
| EP | 3656354 A1 | 5/2020 |
| EP | 1648339 B2 | 6/2020 |
| EP | 2072027 B1 | 6/2020 |
| EP | 2331016 B8 | 6/2020 |
| EP | 2616007 B1 | 6/2020 |
| EP | 2967856 B1 | 6/2020 |
| EP | 3042635 B1 | 6/2020 |
| EP | 3060165 B1 | 6/2020 |
| EP | 3280338 B1 | 6/2020 |
| EP | 3283010 B1 | 6/2020 |
| EP | 3400908 B1 | 6/2020 |
| EP | 3494928 B1 | 6/2020 |
| EP | 3498225 B1 | 6/2020 |
| EP | 3583920 B1 | 6/2020 |
| EP | 3659553 A1 | 6/2020 |
| EP | 3661429 A1 | 6/2020 |
| EP | 3661436 A1 | 6/2020 |
| EP | 3668450 A1 | 6/2020 |
| EP | 3668452 A1 | 6/2020 |

(56) References Cited

FOREIGN PATENT DOCUMENTS

| | | | |
|---|---|---|---|
| EP | 3669828 A1 | 6/2020 |
| EP | 3669829 A1 | 6/2020 |
| EP | 2271284 B1 | 7/2020 |
| EP | 2291145 B1 | 7/2020 |
| EP | 2512952 B1 | 7/2020 |
| EP | 2558029 B1 | 7/2020 |
| EP | 2693985 B1 | 7/2020 |
| EP | 2858708 B1 | 7/2020 |
| EP | 2862546 B1 | 7/2020 |
| EP | 2967807 B1 | 7/2020 |
| EP | 2967866 B1 | 7/2020 |
| EP | 3061421 B1 | 7/2020 |
| EP | 3107497 B1 | 7/2020 |
| EP | 3139862 B1 | 7/2020 |
| EP | 3423000 B1 | 7/2020 |
| EP | 3441045 B1 | 7/2020 |
| EP | 3451972 B1 | 7/2020 |
| EP | 3501454 B1 | 7/2020 |
| EP | 3512466 B1 | 7/2020 |
| EP | 3616652 B1 | 7/2020 |
| EP | 3672528 A1 | 7/2020 |
| EP | 3672529 A1 | 7/2020 |
| EP | 3672532 A1 | 7/2020 |
| EP | 3673925 A1 | 7/2020 |
| EP | 3679894 A1 | 7/2020 |
| EP | 3681439 A1 | 7/2020 |
| EP | 3681441 A1 | 7/2020 |
| EP | 3682852 A1 | 7/2020 |
| EP | 3682854 A1 | 7/2020 |
| EP | 3685802 A1 | 7/2020 |
| EP | 2367505 B1 | 8/2020 |
| EP | 2497445 B1 | 8/2020 |
| EP | 2537486 B1 | 8/2020 |
| EP | 2777616 B1 | 8/2020 |
| EP | 3007651 B1 | 8/2020 |
| EP | 3052053 B1 | 8/2020 |
| EP | 3237033 B1 | 8/2020 |
| EP | 3388005 B1 | 8/2020 |
| EP | 3410986 B1 | 8/2020 |
| EP | 3451974 B1 | 8/2020 |
| EP | 3463192 B1 | 8/2020 |
| EP | 3554423 B1 | 8/2020 |
| EP | 3568089 A4 | 8/2020 |
| EP | 3573544 B1 | 8/2020 |
| EP | 3634255 B1 | 8/2020 |
| EP | 3689299 A1 | 8/2020 |
| EP | 3691567 A1 | 8/2020 |
| EP | 3695810 A1 | 8/2020 |
| EP | 3697342 A1 | 8/2020 |
| EP | 3697346 A1 | 8/2020 |
| EP | 2485795 B1 | 9/2020 |
| EP | 3125777 B1 | 9/2020 |
| EP | 3182930 B1 | 9/2020 |
| EP | 3285690 B1 | 9/2020 |
| EP | 3459500 B1 | 9/2020 |
| EP | 3570782 B1 | 9/2020 |
| EP | 3700467 A1 | 9/2020 |
| EP | 3711711 A1 | 9/2020 |
| EP | 3714936 A1 | 9/2020 |
| EP | 2979667 B2 | 10/2020 |
| EP | 3193783 B1 | 10/2020 |
| EP | 3490501 B1 | 10/2020 |
| EP | 3718509 A1 | 10/2020 |
| EP | 3720363 A1 | 10/2020 |
| EP | 3721811 A1 | 10/2020 |
| EP | 2387973 B1 | 11/2020 |
| EP | 2427144 B1 | 11/2020 |
| EP | 2506777 B1 | 11/2020 |
| EP | 2793743 B1 | 11/2020 |
| EP | 2825203 B1 | 11/2020 |
| EP | 2863842 B1 | 11/2020 |
| EP | 2967700 B1 | 11/2020 |
| EP | 2977026 B1 | 11/2020 |
| EP | 3139864 B1 | 11/2020 |
| EP | 3145451 B1 | 11/2020 |
| EP | 3156007 B1 | 11/2020 |
| EP | 3244834 B1 | 11/2020 |
| EP | 3298987 B1 | 11/2020 |
| EP | 3302362 B1 | 11/2020 |
| EP | 3311777 B1 | 11/2020 |
| EP | 3316819 B1 | 11/2020 |
| EP | 3361988 B1 | 11/2020 |
| EP | 3503813 B1 | 11/2020 |
| EP | 3527170 B1 | 11/2020 |
| EP | 3530236 B1 | 11/2020 |
| EP | 3590471 B1 | 11/2020 |
| EP | 3593762 B1 | 11/2020 |
| EP | 3737336 A1 | 11/2020 |
| EP | 3740162 A1 | 11/2020 |
| EP | 2370138 B1 | 12/2020 |
| EP | 2445450 B1 | 12/2020 |
| EP | 2739250 B1 | 12/2020 |
| EP | 2877123 B1 | 12/2020 |
| EP | 2967834 B1 | 12/2020 |
| EP | 2996632 B1 | 12/2020 |
| EP | 3090703 B1 | 12/2020 |
| EP | 3191025 B1 | 12/2020 |
| EP | 3202371 B1 | 12/2020 |
| EP | 3316822 B1 | 12/2020 |
| EP | 3334382 B1 | 12/2020 |
| EP | 3337424 B1 | 12/2020 |
| EP | 3367896 B1 | 12/2020 |
| EP | 3368582 B1 | 12/2020 |
| EP | 3397208 B1 | 12/2020 |
| EP | 3476366 B1 | 12/2020 |
| EP | 3481303 B1 | 12/2020 |
| EP | 3538028 B1 | 12/2020 |
| EP | 3539510 B1 | 12/2020 |
| EP | 3544548 B1 | 12/2020 |
| EP | 3545906 B1 | 12/2020 |
| EP | 3572117 B1 | 12/2020 |
| EP | 3593763 B1 | 12/2020 |
| EP | 3744291 A1 | 12/2020 |
| EP | 3749254 A1 | 12/2020 |
| EP | 3753535 A1 | 12/2020 |
| EP | 3756623 A1 | 12/2020 |
| EP | 1906883 B1 | 1/2021 |
| EP | 2334261 B1 | 1/2021 |
| EP | 2349096 B1 | 1/2021 |
| EP | 2568924 B1 | 1/2021 |
| EP | 2699202 B1 | 1/2021 |
| EP | 2713894 B1 | 1/2021 |
| EP | 2835112 B1 | 1/2021 |
| EP | 3040054 B1 | 1/2021 |
| EP | 3131502 B1 | 1/2021 |
| EP | 3197397 B1 | 1/2021 |
| EP | 3256178 B1 | 1/2021 |
| EP | 3290007 B1 | 1/2021 |
| EP | 3316821 B1 | 1/2021 |
| EP | 3337412 B1 | 1/2021 |
| EP | 3432834 B1 | 1/2021 |
| EP | 3454786 B1 | 1/2021 |
| EP | 3474778 B1 | 1/2021 |
| EP | 3528748 B1 | 1/2021 |
| EP | 3547966 B1 | 1/2021 |
| EP | 3603576 B1 | 1/2021 |
| EP | 3758651 A1 | 1/2021 |
| EP | 3760164 A1 | 1/2021 |
| EP | 3763331 A1 | 1/2021 |
| EP | 3769721 A1 | 1/2021 |
| EP | 2273951 B1 | 2/2021 |
| EP | 2379008 B1 | 2/2021 |
| EP | 2996641 B1 | 2/2021 |
| EP | 3043747 B1 | 2/2021 |
| EP | 3340936 B1 | 2/2021 |
| EP | 3457985 B1 | 2/2021 |
| EP | 3503847 B1 | 2/2021 |
| EP | 3538027 B1 | 2/2021 |
| EP | 3558168 B1 | 2/2021 |
| EP | 3581232 B1 | 2/2021 |
| EP | 3656354 B1 | 2/2021 |
| EP | 3697324 B1 | 2/2021 |
| EP | 3773271 A1 | 2/2021 |
| EP | 3773329 A1 | 2/2021 |

(56) References Cited

FOREIGN PATENT DOCUMENTS

| | | | |
|---|---|---|---|
| EP | 2299938 | B1 | 3/2021 |
| EP | 2470121 | B1 | 3/2021 |
| EP | 2564811 | B1 | 3/2021 |
| EP | 2679198 | B1 | 3/2021 |
| EP | 3068346 | B1 | 3/2021 |
| EP | 3160394 | B1 | 3/2021 |
| EP | 3169245 | B1 | 3/2021 |
| EP | 3178443 | B1 | 3/2021 |
| EP | 3184081 | B1 | 3/2021 |
| EP | 3226956 | B1 | 3/2021 |
| EP | 3324892 | B1 | 3/2021 |
| EP | 3334354 | B1 | 3/2021 |
| EP | 3402446 | B1 | 3/2021 |
| EP | 3442469 | B1 | 3/2021 |
| EP | 3503851 | B1 | 3/2021 |
| EP | 3506855 | B1 | 3/2021 |
| EP | 3531979 | B1 | 3/2021 |
| EP | 3535010 | B1 | 3/2021 |
| EP | 3581151 | B1 | 3/2021 |
| EP | 3590472 | B1 | 3/2021 |
| EP | 3593760 | B1 | 3/2021 |
| EP | 3646825 | B1 | 3/2021 |
| EP | 3649985 | B1 | 3/2021 |
| EP | 3787561 | A1 | 3/2021 |
| EP | 3790501 | A1 | 3/2021 |
| EP | 3791795 | A1 | 3/2021 |
| EP | 3791828 | A1 | 3/2021 |
| EP | 3796872 | A1 | 3/2021 |
| EP | 3796873 | A1 | 3/2021 |
| EP | 3796875 | A1 | 3/2021 |
| EP | 3796876 | A1 | 3/2021 |
| EP | 1734872 | B1 | 4/2021 |
| EP | 2594230 | B1 | 4/2021 |
| EP | 2624785 | B1 | 4/2021 |
| EP | 2670349 | B1 | 4/2021 |
| EP | 2793752 | B1 | 4/2021 |
| EP | 2823769 | B1 | 4/2021 |
| EP | 2964152 | B1 | 4/2021 |
| EP | 3253331 | B1 | 4/2021 |
| EP | 3290004 | B1 | 4/2021 |
| EP | 3311778 | B1 | 4/2021 |
| EP | 3367979 | B1 | 4/2021 |
| EP | 3454794 | B1 | 4/2021 |
| EP | 3487420 | B1 | 4/2021 |
| EP | 3558165 | B1 | 4/2021 |
| EP | 3616651 | B1 | 4/2021 |
| EP | 3619136 | B1 | 4/2021 |
| EP | 3626208 | B1 | 4/2021 |
| EP | 3632379 | B1 | 4/2021 |
| EP | 3646823 | B1 | 4/2021 |
| EP | 3646824 | B1 | 4/2021 |
| EP | 3653173 | B1 | 4/2021 |
| EP | 1951155 | B1 | 5/2021 |
| EP | 2073755 | B1 | 5/2021 |
| EP | 2948100 | B1 | 5/2021 |
| EP | 3099270 | B1 | 5/2021 |
| EP | 3150172 | B1 | 5/2021 |
| EP | 3178445 | B1 | 5/2021 |
| EP | 3310301 | B1 | 5/2021 |
| EP | 3582697 | B1 | 5/2021 |
| EP | 3592295 | B1 | 5/2021 |
| EP | 3639888 | B1 | 5/2021 |
| EP | 3669828 | B1 | 5/2021 |
| EP | 2471492 | B1 | 6/2021 |
| EP | 2486894 | B1 | 6/2021 |
| EP | 2750630 | B1 | 6/2021 |
| EP | 3247312 | B1 | 6/2021 |
| EP | 3294215 | B1 | 6/2021 |
| EP | 3323353 | B1 | 6/2021 |
| EP | 3360513 | B1 | 6/2021 |
| EP | 3488821 | B1 | 6/2021 |
| EP | 3549555 | B1 | 6/2021 |
| EP | 3576677 | B1 | 6/2021 |
| EP | 3632338 | B1 | 6/2021 |
| EP | 3834879 | A1 | 6/2021 |
| EP | 2381895 | B1 | 7/2021 |
| EP | 2611389 | B1 | 7/2021 |
| EP | 2779945 | B1 | 7/2021 |
| EP | 3193740 | B1 | 7/2021 |
| EP | 3206629 | B1 | 7/2021 |
| EP | 3277222 | B1 | 7/2021 |
| EP | 3400907 | B1 | 7/2021 |
| EP | 3435919 | B1 | 7/2021 |
| EP | 3522800 | B1 | 7/2021 |
| EP | 3539508 | B1 | 7/2021 |
| EP | 3539509 | B1 | 7/2021 |
| EP | 3572044 | B1 | 7/2021 |
| EP | 3592289 | B1 | 7/2021 |
| EP | 3668450 | B1 | 7/2021 |
| EP | 3681439 | B1 | 7/2021 |
| EP | 3691567 | B1 | 7/2021 |
| EP | 3789077 | A4 | 7/2021 |
| EP | 3846740 | A1 | 7/2021 |
| EP | 3849472 | A1 | 7/2021 |
| EP | 2558032 | B1 | 8/2021 |
| EP | 2992857 | B1 | 8/2021 |
| EP | 2994075 | B1 | 8/2021 |
| EP | 3038539 | B1 | 8/2021 |
| EP | 3287099 | B1 | 8/2021 |
| EP | 3348235 | B1 | 8/2021 |
| EP | 3643273 | B1 | 8/2021 |
| EP | 3646822 | B1 | 8/2021 |
| EP | 3658215 | B1 | 8/2021 |
| EP | 3659553 | B1 | 8/2021 |
| EP | 3723665 | B1 | 8/2021 |
| EP | 3744290 | B1 | 8/2021 |
| EP | 3860530 | A1 | 8/2021 |
| EP | 3863567 | A1 | 8/2021 |
| EP | 2040645 | B1 | 9/2021 |
| EP | 2329796 | B1 | 9/2021 |
| EP | 3125827 | B1 | 9/2021 |
| EP | 3137146 | B1 | 9/2021 |
| EP | 3288494 | B1 | 9/2021 |
| EP | 3288497 | B1 | 9/2021 |
| EP | 3446660 | B1 | 9/2021 |
| EP | 3454784 | B1 | 9/2021 |
| EP | 3456293 | B1 | 9/2021 |
| EP | 3457989 | B1 | 9/2021 |
| EP | 3496664 | B1 | 9/2021 |
| EP | 3503848 | B1 | 9/2021 |
| EP | 3512465 | B1 | 9/2021 |
| EP | 3544664 | B1 | 9/2021 |
| EP | 3568089 | B1 | 9/2021 |
| EP | 3592288 | B1 | 9/2021 |
| EP | 3606472 | B1 | 9/2021 |
| EP | 3669829 | B1 | 9/2021 |
| EP | 3672528 | B1 | 9/2021 |
| EP | 3833302 | A4 | 9/2021 |
| EP | 3870110 | A1 | 9/2021 |
| EP | 3881801 | | 9/2021 |
| EP | 2249711 | B1 | 10/2021 |
| EP | 2538883 | B1 | 10/2021 |
| EP | 2723273 | B1 | 10/2021 |
| EP | 3119351 | B1 | 10/2021 |
| EP | 3267946 | B1 | 10/2021 |
| EP | 3275404 | B1 | 10/2021 |
| EP | 3280482 | B1 | 10/2021 |
| EP | 3334381 | B1 | 10/2021 |
| EP | 3639792 | B1 | 10/2021 |
| EP | 3886762 | A1 | 10/2021 |
| EP | 3886763 | A1 | 10/2021 |
| EP | 3892240 | A1 | 10/2021 |
| EP | 3897454 | A1 | 10/2021 |
| EP | 3900679 | A1 | 10/2021 |
| EP | 2331018 | B1 | 11/2021 |
| EP | 2429455 | B1 | 11/2021 |
| EP | 2538878 | B1 | 11/2021 |
| EP | 2699302 | B1 | 11/2021 |
| EP | 2706958 | B1 | 11/2021 |
| EP | 2892467 | B1 | 11/2021 |
| EP | 2999434 | B1 | 11/2021 |
| EP | 3024527 | B1 | 11/2021 |
| EP | 3061422 | B1 | 11/2021 |
| EP | 3107500 | B1 | 11/2021 |

(56) References Cited

FOREIGN PATENT DOCUMENTS

| | | | |
|---|---|---|---|
| EP | 3110468 | B1 | 11/2021 |
| EP | 3154474 | B1 | 11/2021 |
| EP | 3213715 | B1 | 11/2021 |
| EP | 3256076 | B1 | 11/2021 |
| EP | 3288499 | B1 | 11/2021 |
| EP | 3360514 | B1 | 11/2021 |
| EP | 3429507 | B1 | 11/2021 |
| EP | 3445443 | B1 | 11/2021 |
| EP | 3454785 | B1 | 11/2021 |
| EP | 3505077 | B1 | 11/2021 |
| EP | 3672529 | B1 | 11/2021 |
| EP | 3760164 | B1 | 11/2021 |
| EP | 3908228 | A1 | 11/2021 |
| EP | 3912595 | A1 | 11/2021 |
| EP | 3912596 | A1 | 11/2021 |
| EP | 2358307 | B1 | 12/2021 |
| EP | 2765954 | B1 | 12/2021 |
| EP | 2991584 | B1 | 12/2021 |
| EP | 3283011 | B1 | 12/2021 |
| EP | 3288479 | B1 | 12/2021 |
| EP | 3344167 | B1 | 12/2021 |
| EP | 3410987 | B1 | 12/2021 |
| EP | 3481339 | B1 | 12/2021 |
| EP | 3482718 | B1 | 12/2021 |
| EP | 3490465 | B1 | 12/2021 |
| EP | 3498224 | B1 | 12/2021 |
| EP | 3503846 | B1 | 12/2021 |
| EP | 3592284 | B1 | 12/2021 |
| EP | 3749254 | B1 | 12/2021 |
| EP | 3914191 | A1 | 12/2021 |
| EP | 3915493 | A1 | 12/2021 |
| EP | 3740162 | B1 | 1/2022 |
| EP | 3294218 | B1 | 2/2022 |
| EP | 3457988 | B1 | 2/2022 |
| EP | 3481336 | B1 | 2/2022 |
| EP | 3673925 | B1 | 2/2022 |
| EP | 3689299 | B1 | 2/2022 |
| EP | 3753535 | B1 | 2/2022 |
| EP | 3860530 | B1 | 2/2022 |
| EP | 2520249 | B1 | 3/2022 |
| EP | 2558033 | B1 | 3/2022 |
| EP | 2623068 | B1 | 3/2022 |
| EP | 2866737 | B1 | 3/2022 |
| EP | 3107495 | B1 | 3/2022 |
| EP | 3160396 | B1 | 3/2022 |
| EP | 3193782 | B1 | 3/2022 |
| EP | 3334380 | B1 | 3/2022 |
| EP | 3355800 | B1 | 3/2022 |
| EP | 3479797 | B1 | 3/2022 |
| EP | 3479800 | B1 | 3/2022 |
| EP | 3547936 | B1 | 3/2022 |
| EP | 3628274 | B1 | 3/2022 |
| EP | 3679894 | B1 | 3/2022 |
| EP | 3711711 | B1 | 3/2022 |
| EP | 3714936 | B1 | 3/2022 |
| EP | 3787561 | B1 | 3/2022 |
| EP | 3791795 | B1 | 3/2022 |
| EP | 3962415 | A1 | 3/2022 |
| EP | 2488126 | B1 | 4/2022 |
| EP | 2536360 | B1 | 4/2022 |
| EP | 2611388 | B1 | 4/2022 |
| EP | 2651336 | B1 | 4/2022 |
| EP | 2699200 | B1 | 4/2022 |
| EP | 2916781 | B1 | 4/2022 |
| EP | 3174502 | B1 | 4/2022 |
| EP | 3209221 | B1 | 4/2022 |
| EP | 3302297 | B1 | 4/2022 |
| EP | 3349693 | B1 | 4/2022 |
| EP | 3487451 | B1 | 4/2022 |
| EP | 3500184 | B1 | 4/2022 |
| EP | 3600159 | B1 | 4/2022 |
| EP | 3628239 | B1 | 4/2022 |
| EP | 3644866 | B1 | 4/2022 |
| EP | 3681441 | B1 | 4/2022 |
| EP | 3796873 | B1 | 4/2022 |
| EP | 2268231 | B1 | 5/2022 |
| EP | 2856973 | B1 | 5/2022 |
| EP | 2962664 | B1 | 5/2022 |
| EP | 3311774 | B1 | 5/2022 |
| EP | 3335670 | B1 | 5/2022 |
| EP | 3403616 | B1 | 5/2022 |
| EP | 3445290 | B1 | 5/2022 |
| EP | 3541316 | B1 | 5/2022 |
| EP | 3648709 | B1 | 5/2022 |
| EP | 3695810 | B1 | 5/2022 |
| EP | 3721811 | B1 | 5/2022 |
| EP | 3773271 | B1 | 5/2022 |
| EP | 2538893 | B1 | 6/2022 |
| EP | 2575681 | B1 | 6/2022 |
| EP | 2583640 | B1 | 6/2022 |
| EP | 3071149 | B1 | 6/2022 |
| EP | 3253332 | B1 | 6/2022 |
| EP | 3283009 | B1 | 6/2022 |
| EP | 3296979 | B1 | 6/2022 |
| EP | 3298988 | B1 | 6/2022 |
| EP | 3342377 | B1 | 6/2022 |
| EP | 3365349 | B1 | 6/2022 |
| EP | 3397206 | B1 | 6/2022 |
| EP | 3426194 | B1 | 6/2022 |
| EP | 3595588 | B1 | 6/2022 |
| EP | 3636312 | B1 | 6/2022 |
| EP | 3661436 | B1 | 6/2022 |
| EP | 3790501 | B1 | 6/2022 |
| EP | 3846740 | B1 | 6/2022 |
| EP | 3849472 | B1 | 6/2022 |
| EP | 3897454 | B1 | 6/2022 |
| EP | 4014928 | A1 | 6/2022 |
| EP | 2621409 | B1 | 7/2022 |
| EP | 2787926 | B1 | 7/2022 |
| EP | 2838473 | B1 | 7/2022 |
| EP | 2950752 | B1 | 7/2022 |
| EP | 3060171 | B1 | 7/2022 |
| EP | 3206631 | B1 | 7/2022 |
| EP | 3245980 | B1 | 7/2022 |
| EP | 3256073 | B1 | 7/2022 |
| EP | 3311783 | B1 | 7/2022 |
| EP | 3347182 | B1 | 7/2022 |
| EP | 3389557 | B1 | 7/2022 |
| EP | 3463120 | B1 | 7/2022 |
| EP | 3579788 | B1 | 7/2022 |
| EP | 3756623 | B1 | 7/2022 |
| EP | 3796872 | B1 | 7/2022 |
| EP | 3796876 | B1 | 7/2022 |
| EP | 2313152 | B1 | 8/2022 |
| EP | 2688516 | B1 | 8/2022 |
| EP | 2849678 | B1 | 8/2022 |
| EP | 2950751 | B1 | 8/2022 |
| EP | 2964153 | B1 | 8/2022 |
| EP | 3019092 | B1 | 8/2022 |
| EP | 3184082 | B1 | 8/2022 |
| EP | 3231395 | B1 | 8/2022 |
| EP | 3266417 | B1 | 8/2022 |
| EP | 3407834 | B1 | 8/2022 |
| EP | 3458136 | B1 | 8/2022 |
| EP | 3459499 | B1 | 8/2022 |
| EP | 3471662 | B1 | 8/2022 |
| EP | 3484412 | B1 | 8/2022 |
| EP | 3534841 | B1 | 8/2022 |
| EP | 3541328 | B1 | 8/2022 |
| EP | 3672532 | B1 | 8/2022 |
| EP | 3718509 | B1 | 8/2022 |
| EP | 3769721 | B1 | 8/2022 |
| EP | 3789077 | B1 | 8/2022 |
| EP | 3908228 | B1 | 8/2022 |
| EP | 3915493 | B1 | 8/2022 |
| EP | 3967274 | B1 | 8/2022 |
| EP | 2670351 | B1 | 9/2022 |
| EP | 2777617 | B1 | 9/2022 |
| EP | 2810620 | B1 | 9/2022 |
| EP | 2922592 | B1 | 9/2022 |
| EP | 3038567 | B1 | 9/2022 |
| EP | 3096713 | B1 | 9/2022 |
| EP | 3220857 | B1 | 9/2022 |
| EP | 3448315 | B1 | 9/2022 |

(56) References Cited

FOREIGN PATENT DOCUMENTS

| | | | |
|---|---|---|---|
| EP | 3481335 | B1 | 9/2022 |
| EP | 3520715 | B1 | 9/2022 |
| EP | 3645065 | B1 | 9/2022 |
| EP | 3737336 | B1 | 9/2022 |
| EP | 2104470 | B1 | 10/2022 |
| EP | 2536353 | B1 | 10/2022 |
| EP | 2991588 | B1 | 10/2022 |
| EP | 3043755 | B1 | 10/2022 |
| EP | 3288491 | B1 | 10/2022 |
| EP | 3466373 | B1 | 10/2022 |
| EP | 3552585 | B1 | 10/2022 |
| EP | 3791828 | B1 | 10/2022 |
| EP | 3914191 | B1 | 10/2022 |
| EP | 2538882 | B1 | 11/2022 |
| EP | 2698129 | B1 | 11/2022 |
| EP | 2959866 | B1 | 11/2022 |
| EP | 3175823 | B1 | 11/2022 |
| EP | 3280358 | B1 | 11/2022 |
| EP | 3340923 | B1 | 11/2022 |
| EP | 3478224 | B1 | 11/2022 |
| EP | 3490659 | B1 | 11/2022 |
| EP | 3744291 | B1 | 11/2022 |
| FR | 2815844 | B1 | 1/2003 |
| FR | 2826863 | B1 | 9/2003 |
| FR | 2828091 | B1 | 11/2003 |
| FR | 2847800 | B1 | 10/2005 |
| FR | 2858543 | B1 | 2/2006 |
| FR | 2828263 | B1 | 5/2007 |
| FR | 2874812 | B1 | 6/2007 |
| FR | 2874813 | B1 | 6/2007 |
| FR | 2883721 | B1 | 6/2007 |
| FR | 2894131 | B1 | 12/2008 |
| FR | 2899096 | B1 | 12/2008 |
| FR | 2910269 | B1 | 2/2009 |
| FR | 2909857 | B1 | 3/2009 |
| FR | 2906454 | B1 | 4/2009 |
| FR | 2906998 | B1 | 4/2009 |
| FR | 2913879 | B1 | 6/2009 |
| FR | 2916959 | B1 | 9/2009 |
| FR | 2892939 | B1 | 1/2010 |
| FR | 2915678 | B1 | 4/2010 |
| FR | 2930137 | B1 | 4/2010 |
| FR | 2915903 | B1 | 6/2010 |
| FR | 2916627 | B1 | 9/2010 |
| FR | 2920664 | B1 | 9/2010 |
| FR | 2932376 | B1 | 4/2011 |
| FR | 2947716 | B1 | 9/2011 |
| FR | 2945440 | B1 | 12/2012 |
| FR | 2951549 | B1 | 8/2013 |
| FR | 2964855 | B1 | 10/2013 |
| FR | 2977792 | B1 | 10/2013 |
| FR | 2980968 | B1 | 12/2013 |
| FR | 2986149 | B1 | 12/2014 |
| FR | 2997288 | B1 | 1/2015 |
| FR | 2998167 | B1 | 1/2015 |
| FR | 2996747 | B1 | 2/2015 |
| FR | 2996748 | B1 | 2/2015 |
| FR | 3004638 | B1 | 5/2015 |
| FR | 2982763 | B1 | 7/2015 |
| FR | 2991162 | B1 | 7/2015 |
| FR | 3006582 | B1 | 7/2015 |
| FR | 3001121 | B1 | 1/2016 |
| FR | 2998166 | B1 | 2/2016 |
| FR | 3021862 | B1 | 5/2016 |
| FR | 3004917 | B1 | 6/2016 |
| FR | 3006884 | B1 | 6/2016 |
| FR | 3023704 | B1 | 8/2016 |
| FR | 3008885 | B1 | 12/2016 |
| FR | 3033494 | B1 | 3/2017 |
| FR | 3057154 | B1 | 10/2018 |
| FR | 3058631 | B1 | 1/2019 |
| FR | 3058632 | B1 | 1/2019 |
| FR | 3060292 | B1 | 1/2019 |
| FR | 3063631 | B1 | 3/2019 |
| FR | 3020265 | B1 | 9/2019 |
| FR | 3072013 | B1 | 9/2019 |
| GB | 243370 | A | 8/1926 |
| GB | 2407146 | B | 4/2006 |
| GB | 2398245 | B | 3/2007 |
| GB | 2433700 | B | 12/2007 |
| GB | 2478498 | B | 7/2012 |
| GB | 2530487 | B | 12/2016 |
| GB | 2517609 | B | 5/2017 |
| GB | 2538749 | B | 8/2017 |
| GB | 2538072 | B | 11/2017 |
| GB | 2536538 | B | 7/2018 |
| GB | 2548891 | B | 7/2018 |
| JP | 2003518984 | A | 6/2003 |
| JP | 2018519880 | A | 7/2018 |
| JP | 2019069241 | A | 5/2019 |
| JP | 2022537559 | A | 8/2022 |
| WO | 2011137531 | | 11/2011 |
| WO | 2016196933 | | 12/2016 |
| WO | WO-2020257643 | A1 | 12/2020 |

OTHER PUBLICATIONS

"U.S. Appl. No. 16/906,782, Notice of Allowability dated Feb. 16, 2022", 2 pgs.

"U.S. Appl. No. 16/906,782, Notice of Allowance dated Dec. 22, 2021", 11 pgs.

"U.S. Appl. No. 16/906,782, Response filed Nov. 8, 2021 to Restriction Requirement dated Sep. 9, 2021", 8 pgs.

"U.S. Appl. No. 16/906,782, Restriction Requirement dated Sep. 9, 2021", 7 pgs.

"International Application Serial No. PCT/US2020/038726, International Preliminary Report on Patentability dated Dec. 30, 2021", 9 pgs.

"International Application Serial No. PCT/US2020/038726, International Search Report dated Nov. 6, 2020", 4 pgs.

"International Application Serial No. PCT/US2020/038726, Invitation to Pay Additional Fees dated Aug. 25, 2020", 2 pgs.

"International Application Serial No. PCT/US2020/038726, Written Opinion dated Nov. 6, 2020", 7 pgs.

"Japanese Application Serial No. 2021-575410, Voluntary Amendment filed Feb. 8, 2022", w/ English Claims, 11 pgs.

"European Application Serial No. 20827239.3, Response to Communication pursuant to Rules 161 and 162 filed Jul. 26, 2022", 14 pgs.

"Australian Application Serial No. 2020295566, First Examination Report dated Sep. 2, 2022", 3 pgs.

U.S. Appl. No. 16/906,782 U.S. Pat. No. 11,311,376, filed Jun. 19, 2020, Low Profile Prosthetic Mitral Valve.

"European Application Serial No. 20827239.3, Extended European Search Report dated Jun. 19, 2023", 9 pgs.

"Japanese Application Serial No. 2021-575410, Response filed Aug. 22, 2023 to Notification of Reasons for Refusal dated Feb. 28, 2023", w English claims, 14 pgs.

"Australian Application Serial No. 2020295566, Response filed Jun. 28, 2023 to First Examination Report dated Sep. 2, 2022", 28 pgs.

"Canadian Application Serial No. 3143344, Office Action dated Jan. 28, 2023", 4 pgs.

"Canadian Application Serial No. 3143344, Response filed May 23, 2023 to Office Action dated Jan. 28, 2023", 18 pgs.

"Japanese Application Serial No. 2021-575410, Notification of Reasons for Refusal dated Feb. 28, 2023", w/ English Translation, 8 pgs.

"Japanese Application Serial No. 2021-575410, Notification of Reasons for Rejection dated Nov. 10, 2023", W English Translation, 7 pgs.

\* cited by examiner

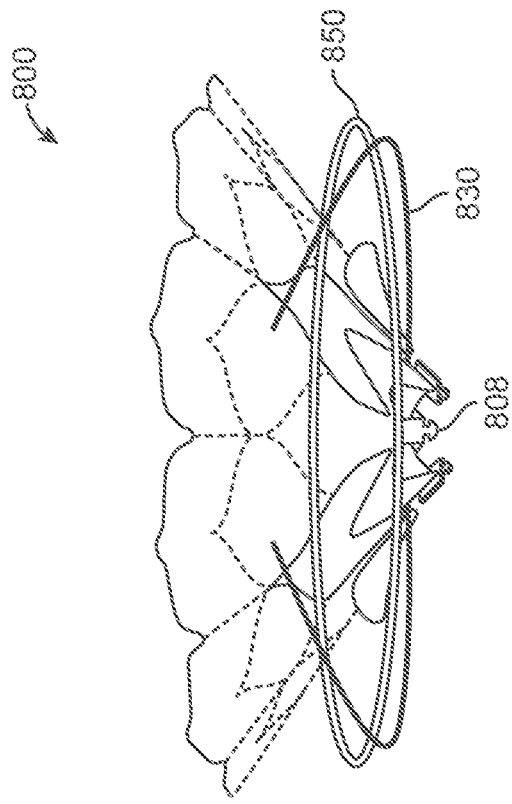
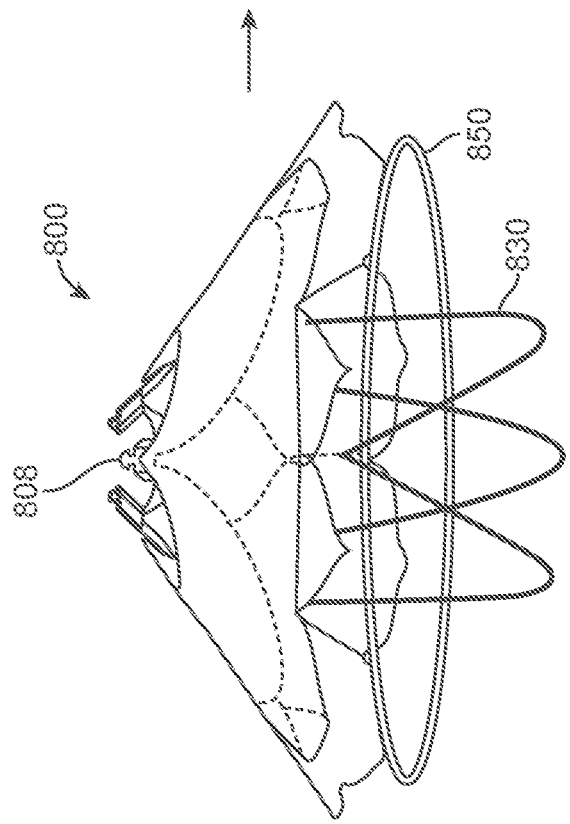
FIG. 8C
FIG. 8B

LOW PROFILE PROSTHETIC MITRAL VALVE

CLAIM OF PRIORITY

The present application is a division of U.S. Non-Provisional patent application Ser. No. 16/906,782 filed on Jun. 19, 2020 and claims the benefit of U.S. Provisional Patent Application No. 62/864,008 filed on Jun. 20, 2019; the entire contents of which are incorporated herein by reference.

BACKGROUND

Mitral valve regurgitation, also known as mitral incompetence, is a serious cardiac condition where the mitral valve fails to properly close and prevent retrograde blood flow across the native mitral valve. This condition can compromise cardiac function and can be debilitating or life threatening.

Current treatments for mitral insufficiency include traditional surgical repair of the native valve. Less invasive transcatheter treatments are being developed.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 8B shows the prosthetic valve of FIG. 8A in a partially deployed configuration.

FIG. 8C shows the prosthetic valve of FIG. 8A in a fully deployed configuration.

DETAILED DESCRIPTION

Traditional surgical repair of the mitral valve can be an effective treatment but requires open heart surgery, a long hospitalization and recovery period. Less invasive transcatheter treatments are being developed and are promising but can be challenging to implant and many have not received regulatory approval for commercial distribution. Therefore, there is a need for improved devices to treat mitral insufficiency. At least some of these challenges are addressed by the examples disclosed herein.

While the examples disclosed herein are directed to an implantable prosthetic mitral valve for treating mitral regurgitation, one of skill in the art will appreciate that this is not intended to be limiting, and the device and methods disclosed herein may also be used to treat other cardiac valves such as the tricuspid valve, aortic valve, pulmonary valve, etc., as well as other valves in the body such as venous valves or any anatomical structure which is used to control the flow of fluids or other materials.

Cardiac Anatomy.

Figure 1:
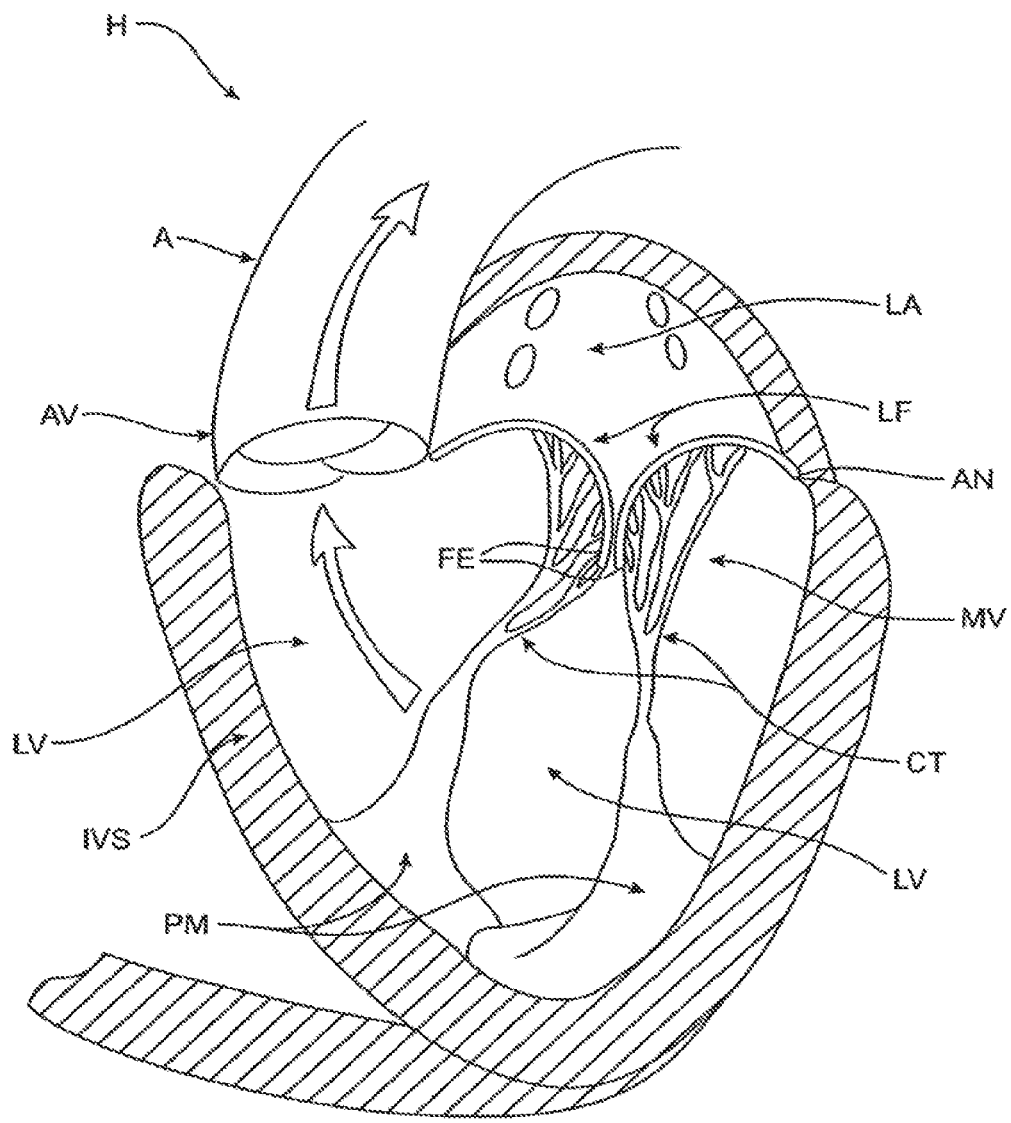
FIG. 1 is a schematic illustration of the left ventricle of a heart showing blood flow during systole.

The left ventricle LV of a normal heart H in systole is illustrated in FIG. 1. The left ventricle LV is contracting and blood flows outwardly through the aortic valve AV, a tricuspid valve in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (also referred to herein as the chordae) which include a plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
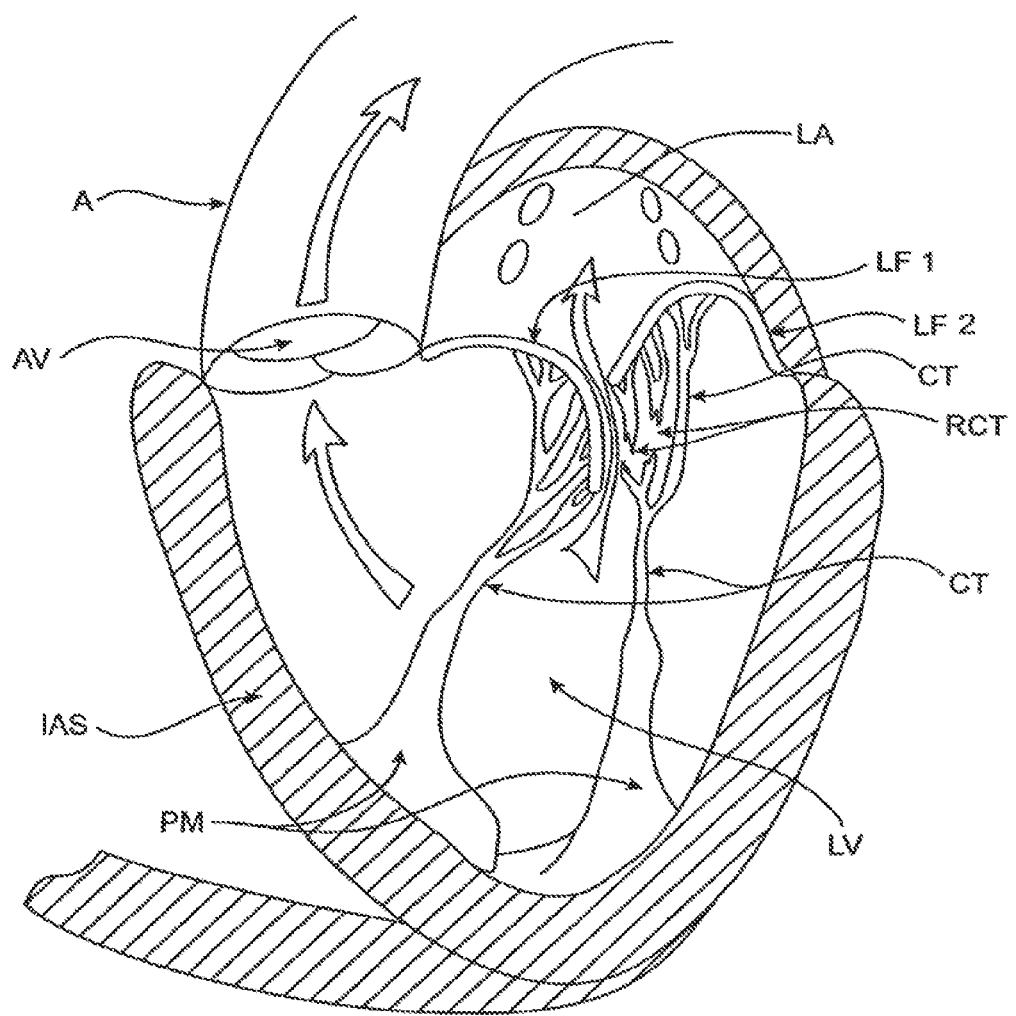
FIG. 2 is a schematic illustration of the left ventricle of a heart having prolapsed leaflets in the mitral valve.
Figure 3A:
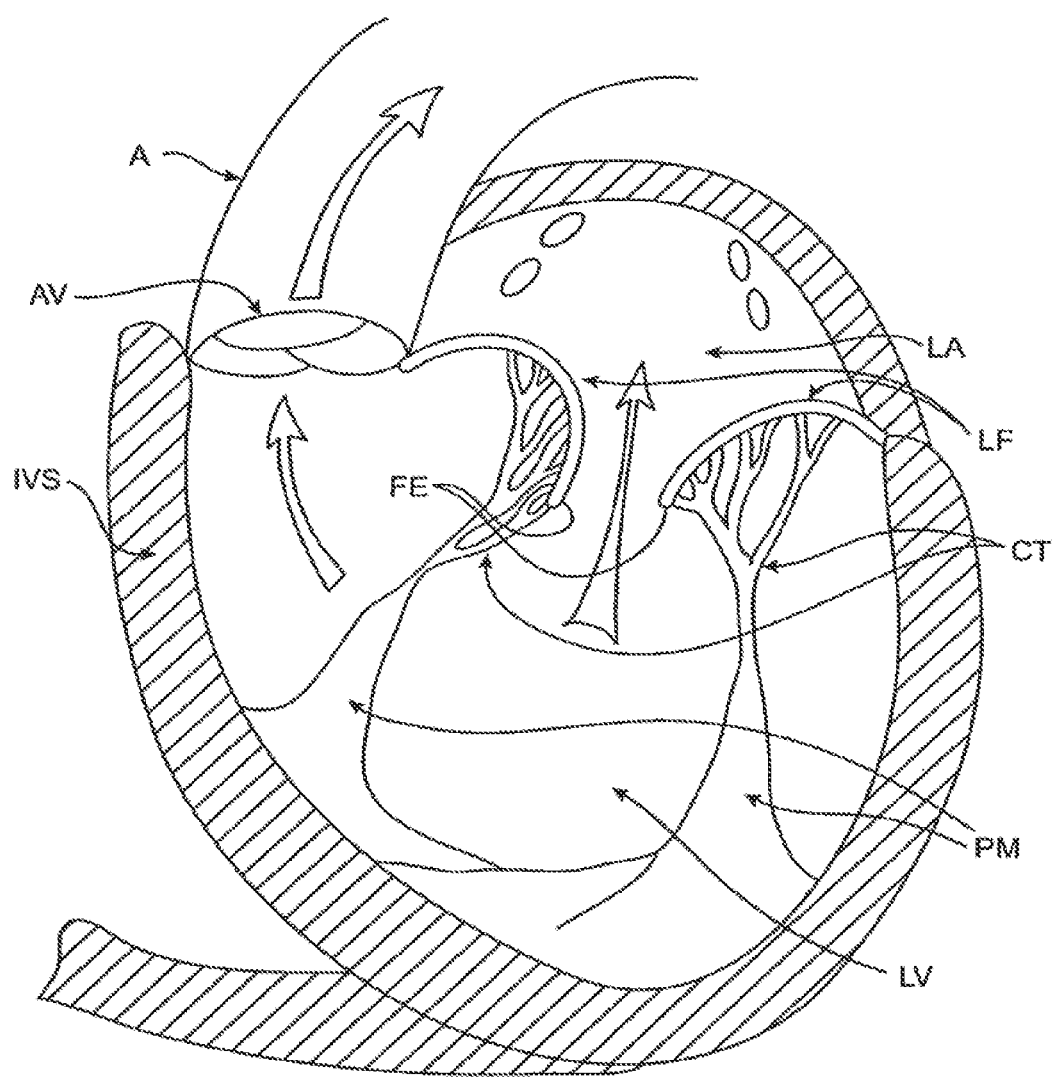
FIG. 3A is a schematic illustration of a heart in a patient suffering from cardiomyopathy where the heart is dilated, and the leaflets do not meet.
Figure 3B:
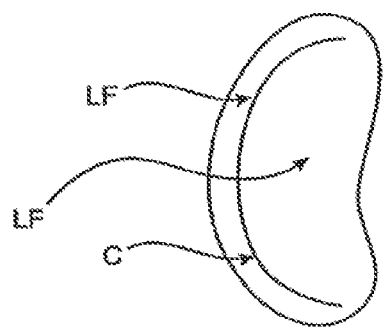
FIG. 3B shows, normal closure of the leaflets.
Figure 3C:
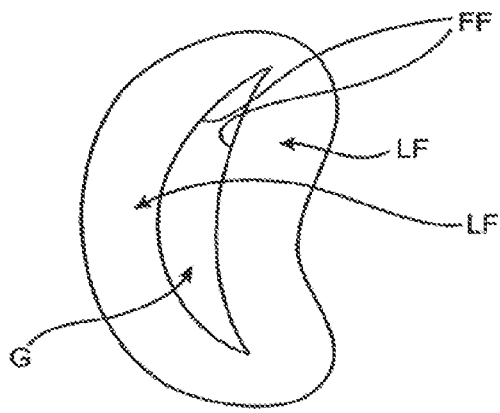
FIG. 3C shows abnormal closure in the dilated heart.
Figure 4:
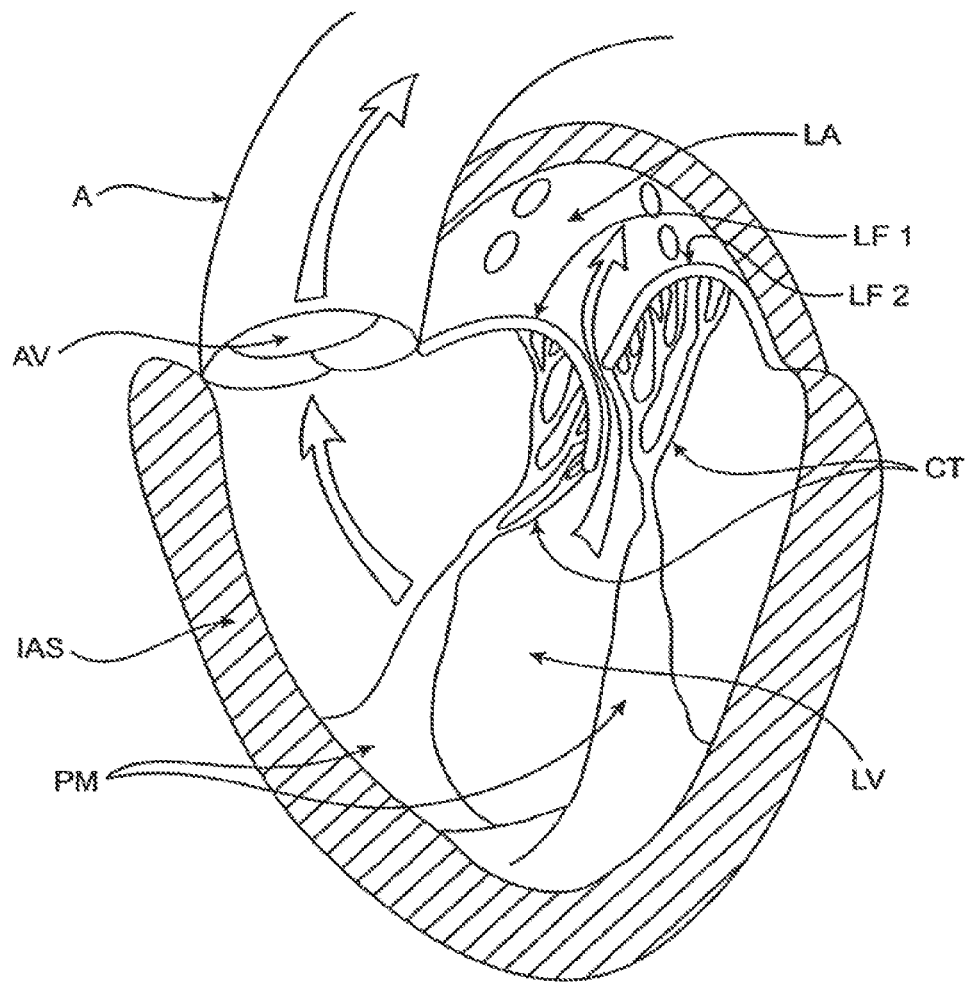
FIG. 4 illustrates mitral valve regurgitation in the left ventricle of a heart having impaired papillary muscles.

Referring now to FIGS. 2-4, a number of structural defects in the heart can cause mitral prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Regurgitation also occurs in the patients suffering from cardiomyopathy where the heart is dilated and the increased size prevents the valve leaflets LF from meeting properly, as shown in FIG. 3A. The enlargement of the heart causes the mitral annulus to become enlarged, making it impossible for the free edges FE to meet during systole. The free edges of the anterior and posterior leaflets normally meet along a line of coaptation C as shown in FIG. 3B, but a significant gap G can be left in patients suffering from cardiomyopathy, as shown in FIG. 3C.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

Figure 5A:
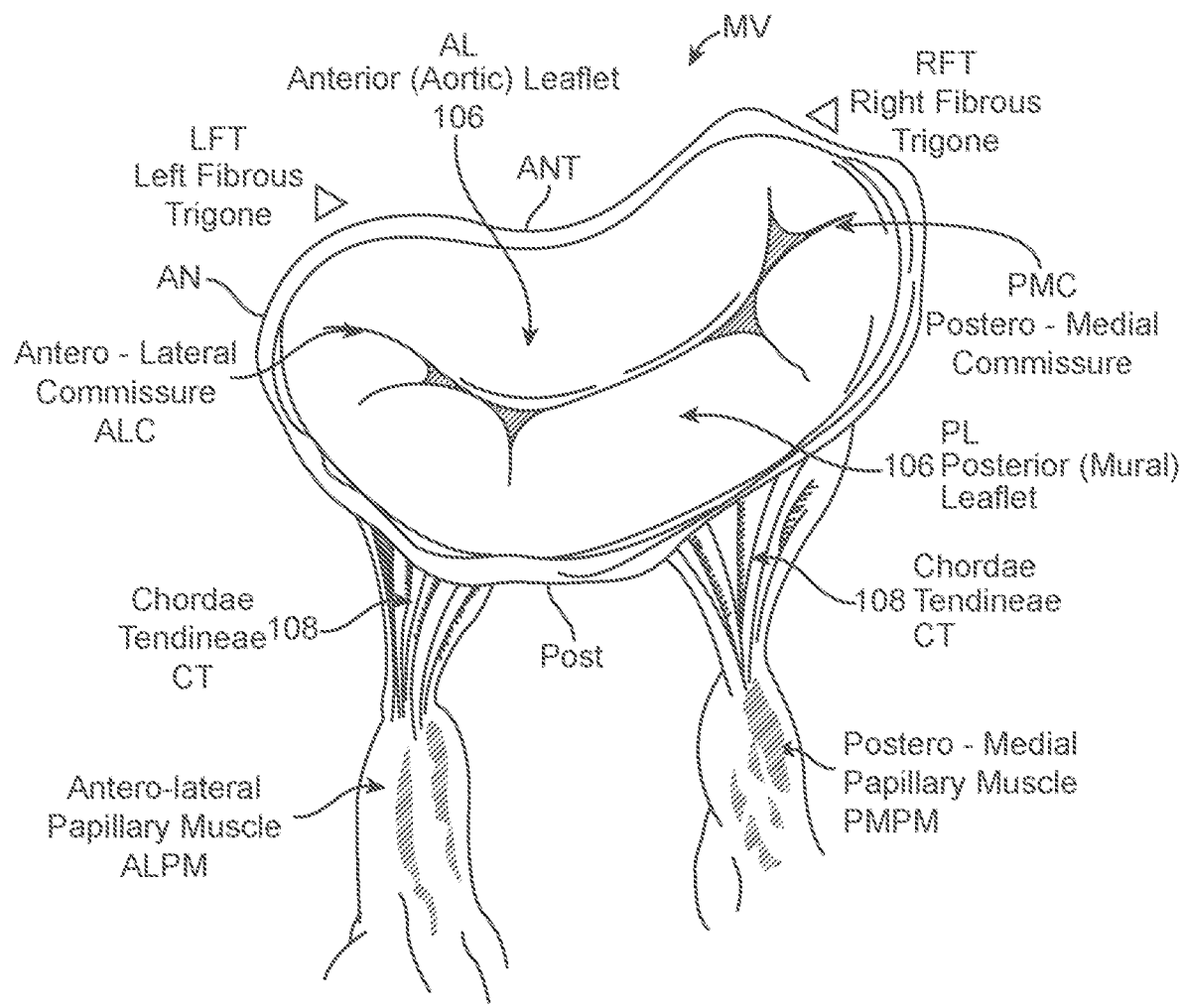
FIGS. 5A-5B illustrate the anatomy of the mitral valve.
Figure 5B:
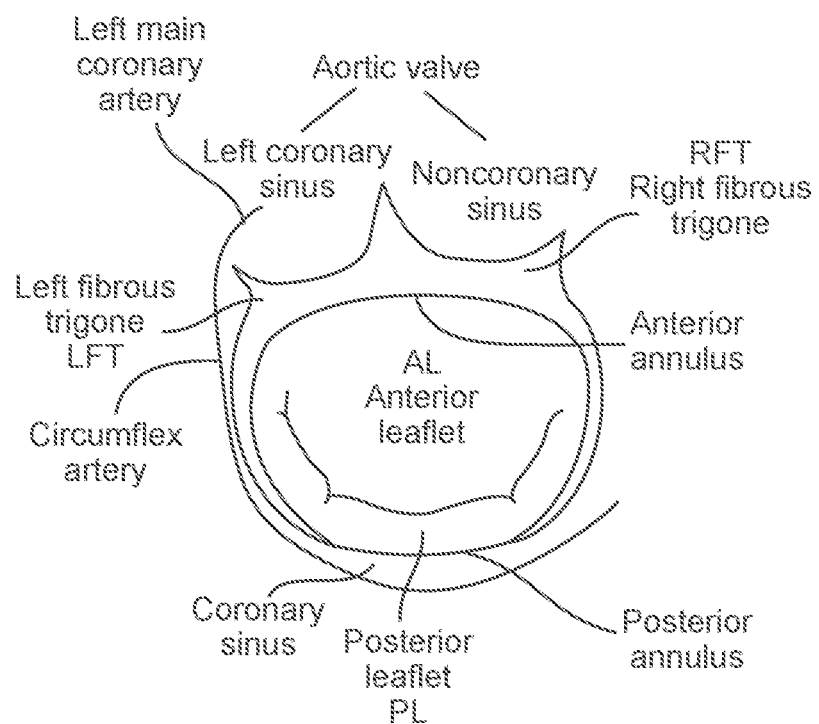

FIG. 5A more clearly illustrates the anatomy of a mitral valve MV which is a bicuspid valve having an anterior side ANT and a posterior side POST. The valve includes an anterior (aortic) leaflet AL and a posterior (mural) leaflet PL. Chordae tendineae CT couple the valve leaflets AL, PL with the antero-lateral papillary muscle ALPM and the postero-medial papillary muscle PMPM. The valve leaflets AL, PL join one another along a line referred to as the antero-lateral commissure ALC and the posterior-medial commissure PMC. The annulus AN circumscribes the valve leaflets, and two regions adjacent an anterior portion of the annulus, on opposite sides of the anterior leaflet are referred to as the left fibrous trigone LFT and also the right fibrous trigone RFT. These areas are indicted by generally by the solid triangles. FIG. 5B more clearly illustrates the left and right fibrous trigones, LFT, RFT.

Prosthetic Valve

Prosthetic valves have been surgically implanted in the heart as a treatment for mitral regurgitation. Some of these valves have been valves harvested from animals such as porcine valves, and others have been prosthetic mechanical valves with or without a tissue covering. More recently, minimally invasive catheter technology has been used to deliver prosthetic valves to the heart. These valves typically include an anchor for securing the prosthetic valve to the patient's heart, and a valve mechanism coupled to the anchor. The valve mechanism often is either a mechanical valve, a valve with animal tissue, or combinations thereof. The prosthetic valve once implanted, takes over for the malfunctioning native valve, thereby reducing or eliminating valvar insufficiency. Some of these valves are challenging to deliver and some are difficult to accurately anchor. Others are large in size which can obstruct the chambers of the heart. While some of these valves appear promising, there still is a need for improved valves that address at least some of these challenges. The following specification discloses examples of a prosthetic valve, a delivery system for the prosthetic valve, and methods of delivering the valve that may overcome some of the challenges associated with existing prosthetic valves.

Figure 6A:
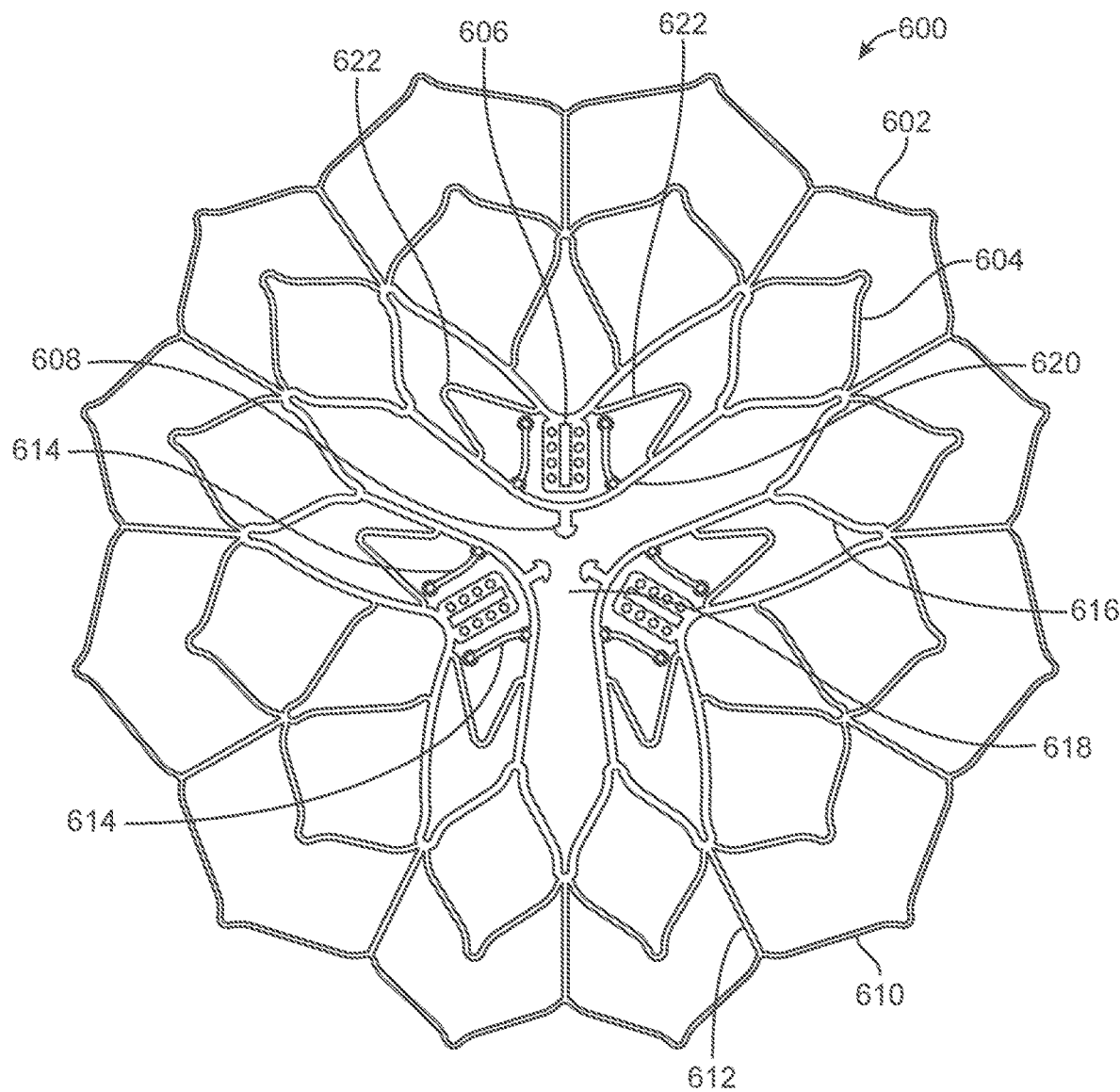
FIG. 6A shows a top view of an example of a low-profile prosthetic valve.

FIG. 6A illustrates an example of a low profile prosthetic mitral valve 600 shown in a flat cut view. The prosthetic mitral valve 600 is an expandable frame formed from a plurality of interconnected struts and may be cut from a flat sheet of material such as stainless steel, nitinol or other biocompatible materials. It may be balloon expandable or self-expanding. The expandable frame is in a flat planar configuration after cutting from the sheet of material and may be heat treated and shape set into a desired shape as will be discussed below. The flat pattern includes a plurality of concentric annular rings 602, 604 that are formed from a plurality of struts which extend around the circumference of the prosthesis. Rings are smaller in diameter and circumference as they get closer to the center of the prosthetic valve. Thus ring 602 has a larger diameter and larger circumference than ring 604. Adjacent rings are coupled together with a plurality of radially extending struts 612 to form a plurality of closed cells circumferentially disposed around the prosthetic valve with adjacent closed cells sharing at least one common strut. Each ring 602, 604 may include a plurality of circumferentially oriented struts that all have the same geometry. For example, outer-most ring 602 incudes a plurality of wishbone shaped struts coupled together to form the annular ring. The wishbone shaped struts may all be the same in ring 602 and they may include two oppositely sloped struts that are coupled together with an arcuate strut that forms a protuberance or peak in the wishbone shaped strut at the inflection point between the two oppositely sloped struts.

The next adjacent ring 604 disposed radially inward from ring 602 is similarly formed with a plurality of wishbone shaped struts coupled together. The wishbone shaped struts in ring 604 may all be the same in ring 604 and they may be similarly formed from two oppositely sloped struts that are coupled together with an arcuate strut that forms a protuberance or peak in the wishbone shaped strut at the inflection point between the two oppositely sloped struts. The sizes and angles of the struts in ring 604 may be different than ring 602 since the two rings are concentric with one another and therefore ring 604 has a smaller diameter and circumference than outer ring 602. A plurality of linear struts 612 that extend radially outward from the center of the prosthesis couple rings 602 and 604 together to form closed cells 610. The closed cells 610 formed between ring 602 and 604 may all have the same geometry, or they may vary.

Struts may be wishbone shaped in order to divert stress and strain away from the apex of the wishbone thereby allowing a greater angular range of motion to be achieved for a given maximum strain, or allowing a lower maximum strain to occur for the same given range of motion.

A Y-shaped strut 616 is coupled to the wishbone shaped second ring 604 with the tail of the Y extending radially inward toward the center of the prosthesis, thereby forming a lemon shaped closed cell with a peak and valley on opposite sides of the closed cell, and pointed ends on the two other sides of the closed cell. The tails of the Y may be coupled together to define a central aperture 618 in the prosthesis. In this example, the central aperture 618 is star shaped with three pointed arms extending radially outward to form the star shape.

A plurality of inner closed cells 620, here three closed cells 620, are formed by two V-shaped struts 622 on opposite sides of the closed cell 620 coupled to the tails of adjacent Y-shaped struts 616 to form the closed cells 620. Each closed cell 620 contains a commissure tab 606 and two ventricular anchor struts 614

Commissure tabs 606 may be adjacent the center of the prosthesis and may include a plurality of suture holes so that the prosthetic valve leaflets may be sutured to the commissure tabs. The commissure tabs 606 may be a rectangular shaped strut with a slit through the middle for receiving prosthetic leaflets. In this example there are three prosthetic valve leaflets (not shown) attached to the commissure tabs forming a tricuspid prosthetic valve. The prosthetic valve leaflets are not illustrated for ease in viewing the expandable frame. The commissure tabs are disposed in between struts 614 which form ventricular anchor tabs that anchor the prosthesis to a ventricular portion of the native valve, such as an anterior portion of the native valve (such as the fibrous trigones) and a posterior portion of the native valve. Struts 614 form part of the ventricular anchors. Two struts 614 are disposed on either side of the commissure tabs 606. One end of strut 614 is coupled to a tail of the Y-shaped strut 616, and the opposite end of struts 614 is a free end that may be bend radially outward. The free end may include a through hole which is used for attachment of a cover (not shown). The cover may be any material such as a polymer like Dacron, and forms a foot which is a soft atraumatic tip for engaging tissue. The Dacron or other polymer cover material provides greater surface area and therefore reduces the chance of the ventricular anchor tabs piercing tissue. The ventricular tabs can then angulate away from the valve frame during expansion to allow anchoring on the fibrous trigones or any other anterior portion of the ventricular side of the native valve, or any portion on the posterior annulus of the native valve.

Facing radially inward toward the center of the device may be a plurality of anchor tabs 608, here mushroom head shaped tabs 608 or T-shaped heads, which allow the prosthesis to be coupled to a delivery catheter as will be described below. In this or any other example, the T-shaped or mushroom head anchor tabs may be omitted and simply have an aperture through the tab that allows a pin or other connector element to be disposed in the aperture for releasable coupling with a delivery catheter, as will be described in greater detail below. The anchor tabs 608 are disposed on a portion of strut that joins two tails of Y-shaped struts 616 together. Thus, in this example there are three connection points that may be made with a delivery catheter.

Figure 6B:
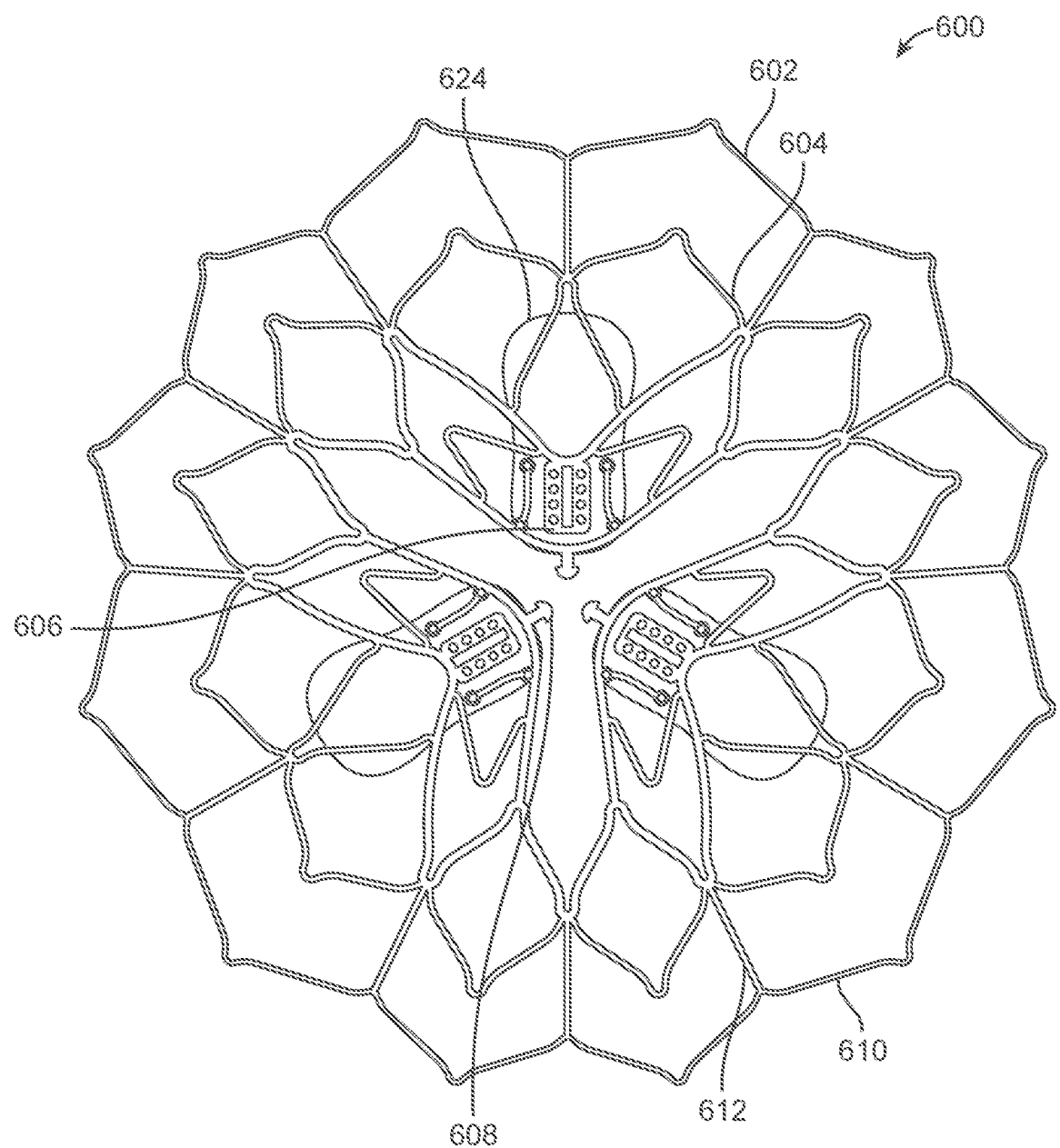
FIG. 6B shows the ventricular anchors of the example in FIG. 6A.

FIG. 6B illustrates prosthetic valve 600 with the cover 624 disposed over the struts 614 and prosthetic frame to form a foot which helps create the ventricular anchors. This is shown by the shaded regions. The foot includes an enlarged head region and a narrower body. Again, the enlarged head provides a larger surface area and therefore minimizes pressure applied to tissue during anchoring in order to eliminate or reduce tissue trauma. Other aspects of FIG. 6B are the same as FIG. 6A.

Figure 6C:
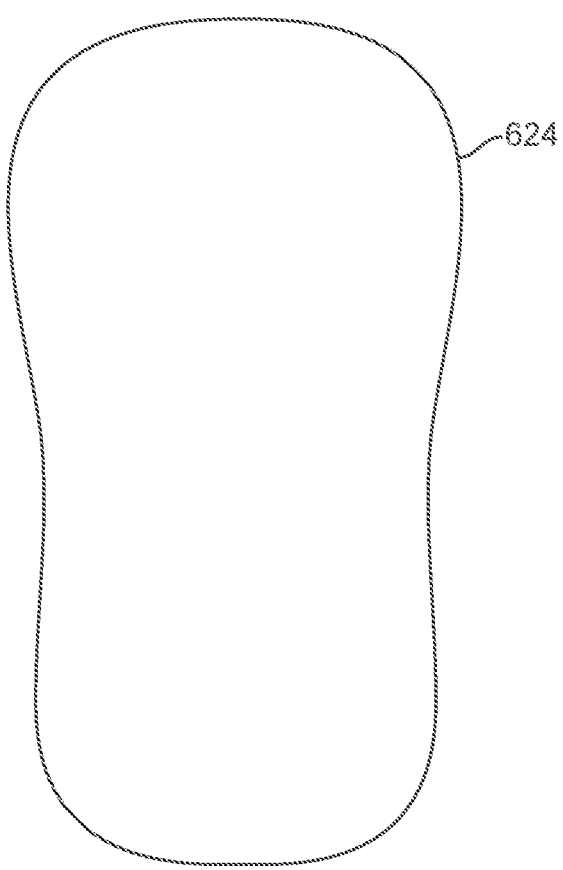
FIG. 6C shows a cover that may be attached to the ventricular anchors of the valve in FIG. 6A

FIG. 6C shows an example of a cover 624 that may be attached to struts 614 to form the atraumatic tip of the ventricular anchors. The cover may be Dacron, or another polymer, or any material that has the desired mechanical properties. Cover 624 has an enlarged head region and a thinner elongate body region. The enlarged head region provided greater surface area in order to reduce contact pressure with tissue during anchoring in order to eliminate or reduce tissue piercing and trauma.

Figure 6D:
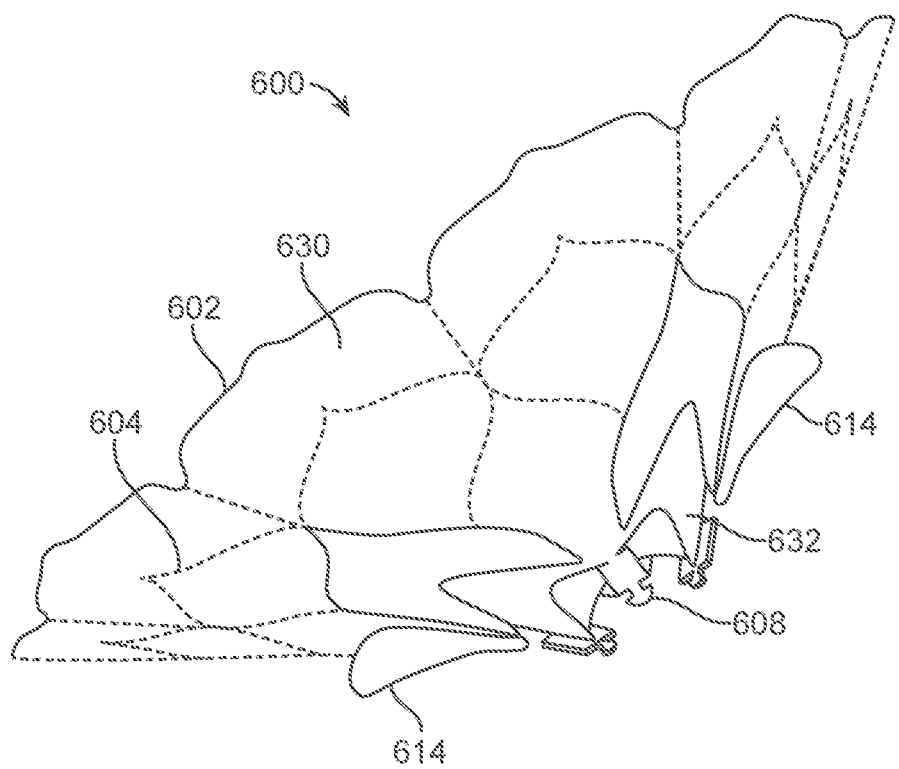
FIG. 6D shows a perspective view of the valve in FIG. 6A.

FIG. 6D is a perspective view of the prosthetic valve 600 shown in FIGS. 6A-6B but with the covering 630 shown disposed over the expandable frame and after shape setting. In addition to a covering disposed over the ventricular anchors 614 to form atraumatic anchor tabs, the same material or another material may be disposed over any or all of the struts and closed cells to minimize perivalvular leakage and promote tissue ingrowth. FIG. 6D shows the prosthetic valve 600 in the fully expanded configuration after shape setting, where the prosthesis is flared upward in an atrial direction (or tapered in a ventricular direction) and the upper atrial end which is the inflow end of the prosthesis is the largest diameter and the valve tapers down to a smaller diameter on the ventricular end which is the outflow end. The funnel shape of the frame may also be described as parabaloidal-like with the concave portion of the paraboloid facing up toward the atrium and the convex portion of the paraboloid facing downward toward the ventricle. The prosthetic valve has an intermediate expanded configuration where the paraboloid is inverted so that the prosthesis flares outward from the upper to lower ends so the flaring is in the direction of the ventricle or the tapering is in the direction of the atrium. If parabaloid shaped, then and the concave portion of the paraboloid faces downward toward the ventricle while the convex portion of the paraboloid faces upward toward the atrium. This intermediate expanded configuration is illustrated and described in greater detail below. Prosthetic valve 600 also includes three commissure posts with three prosthetic valve leaflets 632 coupled to the commissure posts to form the prosthetic valve mechanism.

Figure 7A:
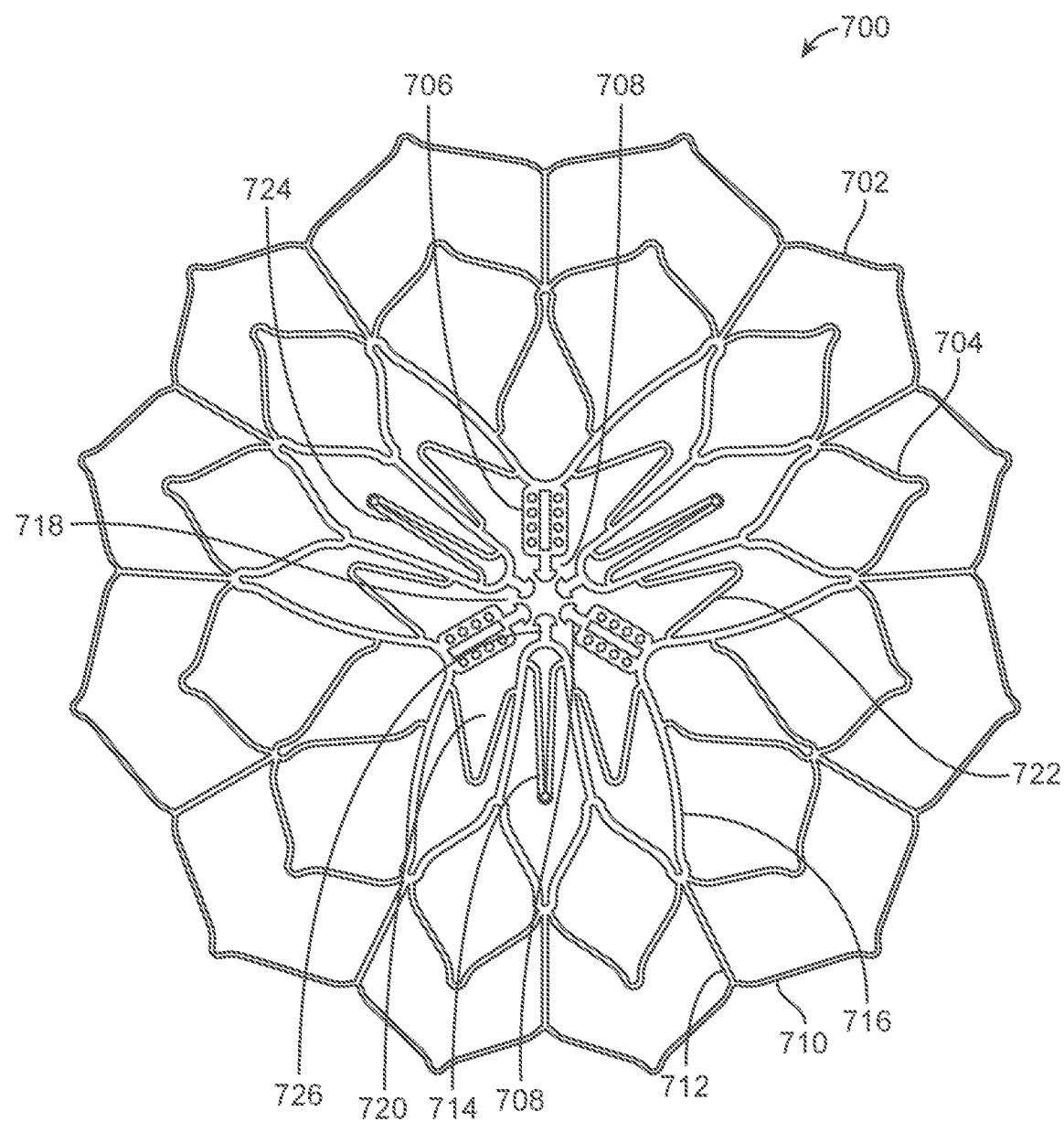
FIG. 7A shows a top view of another example of a low-profile prosthetic valve.

FIG. 7A illustrates an example of a low profile prosthetic mitral valve 700 shown in a flat cut view. The prosthetic mitral valve 700 is an expandable frame formed from a plurality of interconnected struts and may be cut from a flat sheet of material such as stainless steel, nitinol or other biocompatible materials. It may be balloon expandable or self-expanding. The expandable frame is in a flat planar configuration after cutting from the sheet of material and may be heat treated and shape set into a desired shape as will be discussed below. The flat pattern includes a plurality of concentric annular rings 702, 704 that are formed from a plurality of struts which extend around the circumference of the prosthesis. Rings are smaller in diameter and circumference as they get closer to the center of the prosthetic valve. Thus ring 702 has a larger diameter and larger circumference than ring 704. Adjacent rings are coupled together with a plurality of radially extending struts 712 to form a plurality of closed cells circumferentially disposed around the prosthetic valve with adjacent closed cells sharing at least one common strut. Each ring 702, 704 may include a plurality of circumferentially oriented struts that all have the same geometry. For example, outer-most ring 702 incudes a plurality of wishbone shaped struts coupled together to form the annular ring. The wishbone shaped struts may all be the same in ring 702 and they may include two oppositely sloped struts that are coupled together with an arcuate strut that forms a protuberance or peak in the wishbone shaped strut at the inflection point between the two oppositely sloped struts.

The next adjacent ring 704 disposed radially inward from ring 702 is similarly formed with a plurality of wishbone shaped struts coupled together. The wishbone shaped struts in ring 704 may all be the same in ring 704 and they may be similarly formed from two oppositely sloped struts that are coupled together with an arcuate strut that forms a protuberance or peak in the wishbone shaped strut at the inflection point between the two oppositely sloped struts. The sizes and angles of the struts in ring 704 may be different than ring 702 since the two rings are concentric with one another and therefore ring 704 has a smaller diameter and circumference than outer ring 702. A plurality of linear struts 712 that extend radially outward from the center of the prosthesis couple rings 702 and 704 together to form closed cells 710. The closed cells 710 formed between ring 702 and 704 may all have the same geometry, or they may vary. The construct of the connected struts making rings coupled together to form closed cells creates a lattice structure that once shape set provides a flower-like shape, for example similar to a daisy.

Struts may be wishbone shaped in order to divert stress and strain away from the apex of the wishbone thereby allowing a greater angular range of motion to be achieved for a given maximum strain, or allowing a lower maximum strain to occur for the same given range of motion.

A Y-shaped strut 716 is coupled to the wishbone shaped second ring 704 with the tail of the Y extending radially inward toward the center of the prosthesis, thereby forming several tear drop shaped closed cells with pointed ends on opposite sides of the tear drop shape as well as several lemon shaped closed cells which are substantially the same as in the example FIG. 6A. The tails of the Y may be coupled together with V-shaped struts to define an inner closed cell 720 with a central aperture 718 in the prosthesis. In this example, the central aperture 718 has a central circular hole with a plurality of pointed arms extending radially outward from the central circular hole.

Inner closed cell 720 is formed by V-shaped struts 722 coupled to the tails of adjacent Y-shaped struts 716 to form the closed cell 720. Closed cell 720 contains three commissure tabs 706 and extending radially outward from closed cell 720 are three V-shaped struts which form ventricular anchors 724 configured to engage a ventricular inferior surface of the native valve. The legs of the ventricular anchors may be coupled to the tails of the Y-shaped struts, and the apex of the V (or the trough of the V, or free end of the V) may include a hole extending therethrough sized to receive a suture so that a cover similar to the cover in FIG. 6C may be attached to the anchor to form an atraumatic tip.

Commissure tabs 706 may be adjacent the center of the prosthesis and may include a plurality of suture holes so that the prosthetic valve leaflets may be sutured to the commissure tabs. The commissure tabs 706 may be a rectangular shaped strut with a slit through the middle for receiving prosthetic leaflets. In this example there are three prosthetic valve leaflets (not shown) attached to the commissure tabs forming a tricuspid prosthetic valve. The prosthetic valve leaflets are not illustrated for ease in viewing the expandable frame. The commissure tabs are disposed in between adjacent ventricular anchors 724 that anchor the prosthesis to a ventricular portion of the native valve, such as an anterior portion of the native valve (such as the fibrous trigones) and a posterior portion of the native valve. The free end of the ventricular anchor may be bend radially outward. The free end may include a through hole which is used for attachment of a cover (not shown). The cover may be any material such as a polymer like Dacron, and forms a foot which is a soft atraumatic tip for engaging tissue. The Dacron or other polymer cover material provides greater surface area and therefore reduces the chance of the ventricular anchor tabs piercing tissue. The ventricular tabs can then angulate away from the valve frame during expansion to allow anchoring on the fibrous trigones or any other anterior portion of the ventricular side of the native valve, or any portion on the posterior annulus of the native valve.

Facing radially inward toward the center of the device may be a plurality of anchor tabs 708 coupled to the commissures 706, here mushroom head shaped tabs 708 or T-shaped heads, which allow the prosthesis to be coupled to a delivery catheter as will be described below. In addition to the three anchor tabs 708 on the commissures, three additional anchor tabs 726 are coupled to a strut that joins the tails of two adjacent Y-shaped struts 716 and anchor tabs 726 face radially inward toward the center of the prosthesis. Anchor tabs 726 may also be mushroom head shaped, or T-shaped, or other shapes. Both anchor tabs 708, 726 may be used to releasably couple the prosthesis with a delivery catheter. Thus, in this example there are six connection points that may be made with a delivery catheter. Other aspects of the example in FIG. 7A may be substantially similar to the example in FIG. 6A.

Figure 7B:
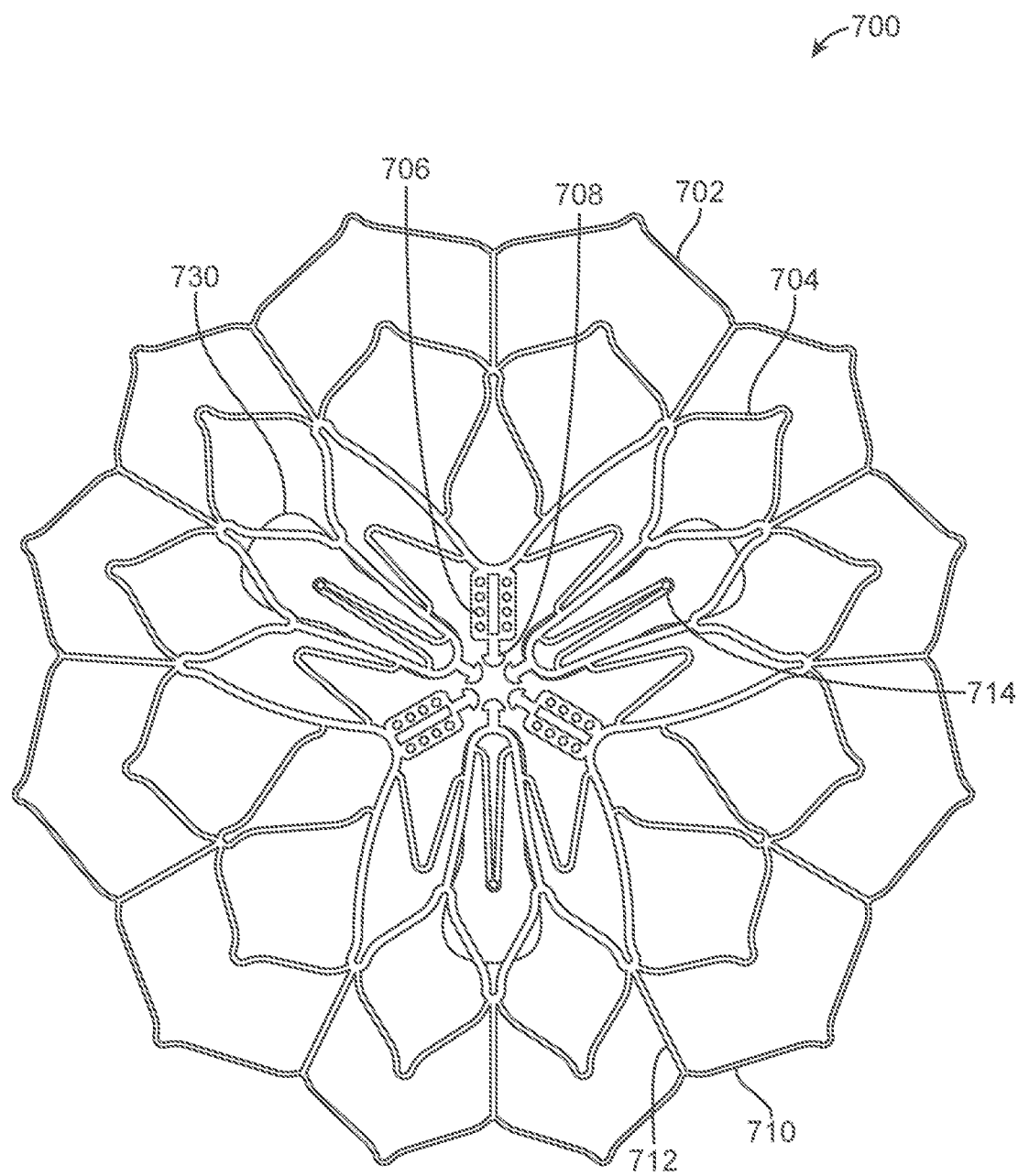
FIG. 7B shows the ventricular anchors of the example in FIG. 7A.

FIG. 7B illustrates prosthetic valve 700 with the cover 730 disposed over the ventricular anchors 714 and prosthetic frame to form a foot which helps create the ventricular anchors. The foot includes an enlarged head region and a narrower body. Again, the enlarged head provides a larger surface area and therefore minimizes pressure applied to tissue during anchoring in order to eliminate or reduce tissue trauma. Other aspects of FIG. 7B are the same as FIG. 7A.

Figure 7C:
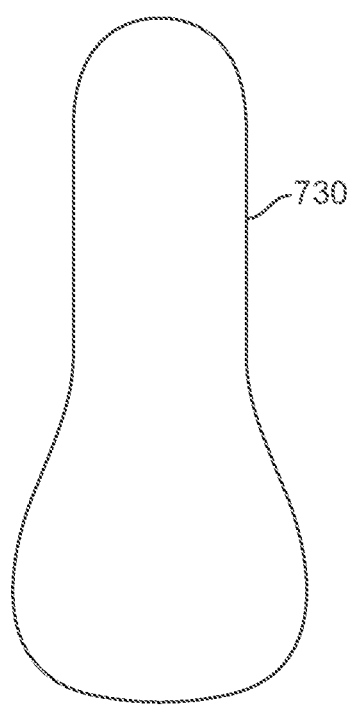
FIG. 7C shows an example of a cover that may be used on the ventricular anchors of FIG. 7B.

FIG. 7C shows an example of a cover 730 that may be attached to ventricular anchors 714 to form the atraumatic tip of the ventricular anchors. The cover may be Dacron, or another polymer, or any material that has the desired mechanical properties. Cover 730 has an enlarged head region and a thinner elongate body region. The enlarged head region provides greater surface area in order to reduce contact pressure with tissue during anchoring in order to eliminate or reduce tissue piercing and trauma.

Figure 7D:
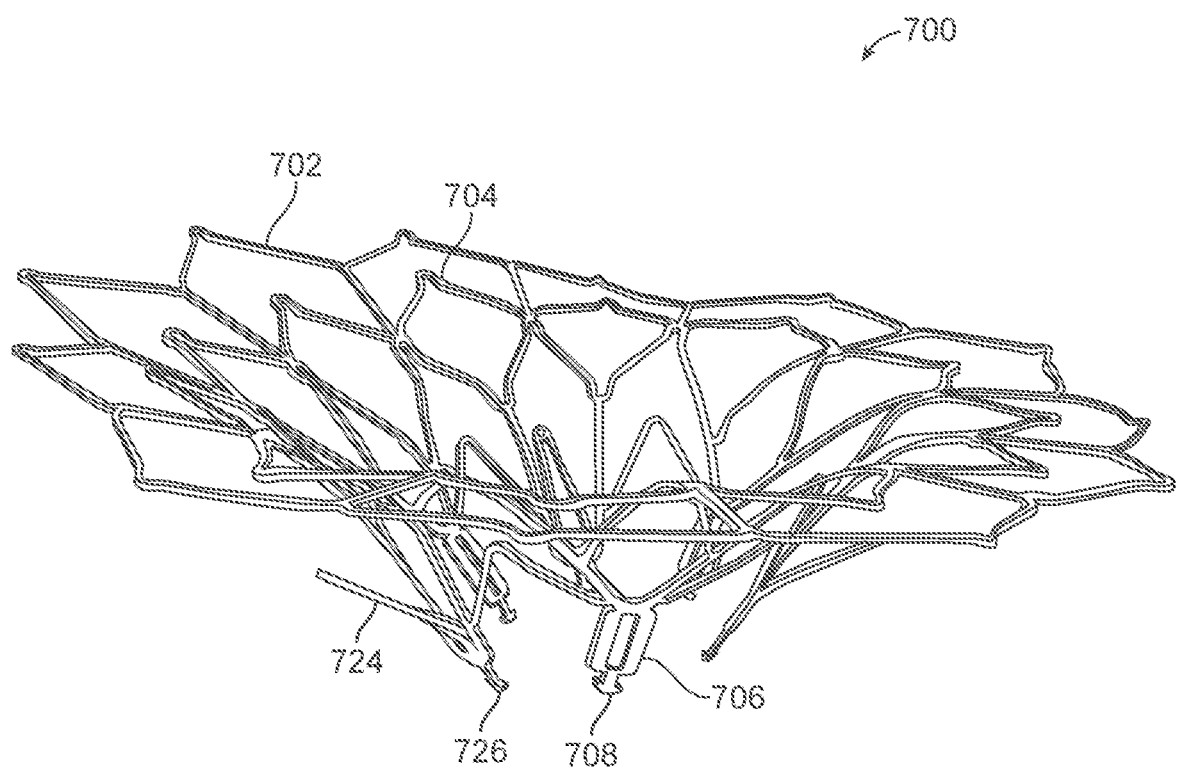
FIG. 7D shows a perspective view of the example in FIG. 7A.

FIG. 7D is a perspective view of the prosthetic valve 700 shown in FIGS. 7A-7B but with the covering removed for ease in viewing the struts of the expandable frame, and after shape setting. In addition to a covering disposed over the ventricular anchors, the same material or another material may be disposed over the any or all of the struts and closed cells. FIG. 7D shows the prosthetic valve 700 in the fully expanded configuration after shape setting, where the prosthesis flares in the atrial direction (or tapers toward the ventricle) and the upper atrial end which is the inflow end of the prosthesis is the largest diameter and the valve tapers down to a smaller diameter on the ventricular end which is the outflow end. The funnel shape of the frame may also be described as parabaloidal-like with the concave portion of the paraboloid facing up toward the atrium and the convex portion of the paraboloid facing downward toward the ventricle. The prosthetic valve has an intermediate expanded configuration where the prosthesis is tapered toward the atrium or flared toward the ventricle, and if paraboloid shaped, the paraboloid is inverted so that the prosthesis flares outward from the upper end to the lower end and the concave portion of the paraboloid faces downward toward the ventricle while the convex portion of the paraboloid faces upward toward the atrium. This intermediate expanded configuration is illustrated and described in greater detail below.

Figure 8A:
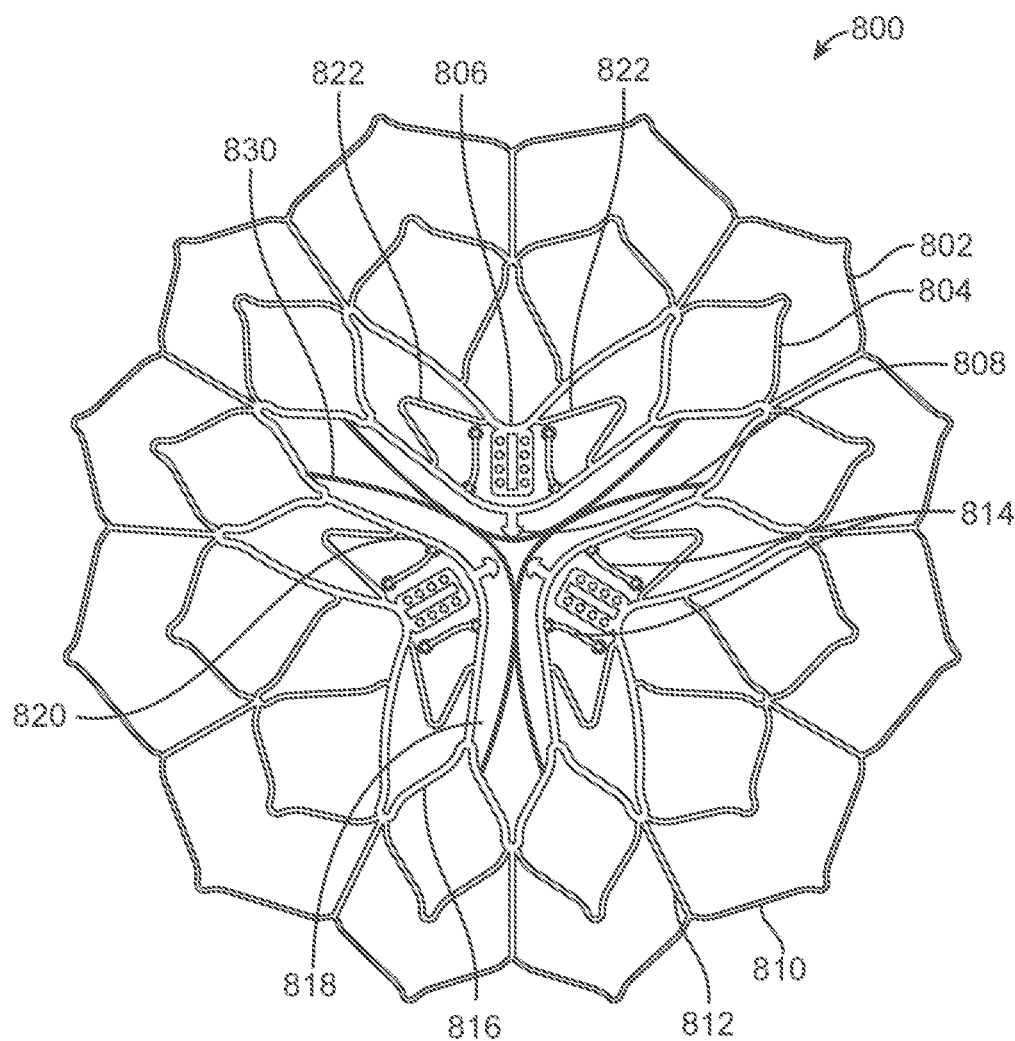
FIG. 8A shows a top view of another example of a low-profile prosthetic valve.

FIG. 8A illustrates another example of a low profile prosthetic mitral valve 800 shown in a flat cut view. Prosthetic valve 800 is substantially similar to the prosthetic valve 600 in FIGS. 6A-6D with the major difference being the addition of ventricular petals or wings 830 to help anchor the prosthesis to the ventricular side of the native valve and capture adjacent native valve leaflets. The prosthetic mitral valve 800 is an expandable frame formed from a plurality of interconnected struts and may be cut from a flat sheet of material such as stainless steel, nitinol or other biocompatible materials. It may be balloon expandable or self-expanding. The expandable frame is in a flat planar configuration after cutting from the sheet of material and may be heat treated and shape set into a desired shape as will be discussed below. The flat pattern includes a plurality of concentric annular rings 802, 804 that are formed from a plurality of struts which extend around the circumference of the prosthesis. Rings are smaller in diameter and circumference as they get closer to the center of the prosthetic valve. Thus ring 802 has a larger diameter and larger circumference than ring 804. Adjacent rings are coupled together with a plurality of radially extending struts 812 to form a plurality of closed cells circumferentially disposed around the prosthetic valve with adjacent closed cells sharing at least one common strut. Each ring 802, 804 may include a plurality of circumferentially oriented struts that all have the same geometry. For example, outer-most ring 802 includes a plurality of wishbone shaped struts coupled together to form the annular ring. The wishbone shaped struts may all be the same in ring 802 and they may include two oppositely sloped struts that are coupled together with an arcuate strut that forms a protuberance or peak in the wishbone shaped strut at the inflection point between the two oppositely sloped struts.

The next adjacent ring 804 disposed radially inward from ring 802 is similarly formed with a plurality of wishbone shaped struts coupled together. The wishbone shaped struts in ring 804 may all be the same in ring 804 and they may be similarly formed from two oppositely sloped struts that are coupled together with an arcuate strut that forms a protuberance or peak in the wishbone shaped strut at the inflection point between the two oppositely sloped struts. The sizes and angles of the struts in ring 804 may be different than ring 802 since the two rings are concentric with one another and therefore ring 804 has a smaller diameter and circumference than outer ring 802. A plurality of linear struts 812 that extend radially outward from the center of the prosthesis couple rings 802 and 804 together to form closed cells 810. The closed cells 810 formed between ring 802 and 804 may all have the same geometry, or they may vary.

Struts may be wishbone shaped in order to divert stress and strain away from the apex of the wishbone thereby allowing a greater angular range of motion to be achieved for a given maximum strain, or allowing a lower maximum strain to occur for the same given range of motion.

A Y-shaped strut 816 is coupled to the wishbone shaped second ring 804 with the tail of the Y extending radially inward toward the center of the prosthesis, thereby forming a lemon shaped closed cell with a peak and valley on opposite sides of the closed cell, and pointed ends on the two other sides of the closed cell. The Y-shaped strut may also be coupled to the wishbone shaped second ring 804 with the tail of the Y extending radially inward toward the center of the prosthesis to form several tear drop shaped closed cells with pointed ends on opposite side of the tear drop shape. The tails of the Y may be coupled together to define a central aperture 818 in the prosthesis. In this example, the central aperture 818 is star shaped with three pointed arms extending radially outward to form the star shape.

A plurality of inner closed cells 820, here three closed cells 820, are formed by two V-shaped struts 822 on opposite sides of the closed cell 820 coupled to the tails of adjacent Y-shaped struts 816 to form the closed cells 820. Each closed cell 820 contains a commissure tab 806 and two ventricular anchor struts 814.

Commissure tabs 806 may be adjacent the center of the prosthesis and may include a plurality of suture holes so that the prosthetic valve leaflets may be sutured to the commissure tabs. The commissure tabs 806 may be a rectangular shaped strut with a slit through the middle for receiving prosthetic leaflets. In this example there are three prosthetic valve leaflets (not shown) attached to the commissure tabs forming a tricuspid prosthetic valve. The prosthetic valve leaflets are not illustrated for ease in viewing the expandable frame. The commissure tabs are disposed in between struts 814 which form ventricular anchor tabs that anchor the prosthesis to a ventricular portion of the native valve, such as an anterior portion of the native valve (such as the fibrous trigones) and a posterior portion of the native valve. Struts 814 form part of the ventricular anchors. Two struts 814 are disposed on either side of the commissure tabs 806. One end of strut 814 is coupled to a tail of the Y-shaped strut 816, and the opposite end of struts 814 is a free end that may be bent radially outward. The free end may include a through hole which is used for attachment of a cover (not shown) such as suturing. The cover may be any material such as a polymer like Dacron, and forms a foot which is a soft atraumatic tip for engaging tissue. The Dacron or other polymer cover material provides greater surface area and therefore reduces the chance of the ventricular anchor tabs piercing tissue. The ventricular tabs can then angulate away from the valve frame during expansion to allow anchoring on the fibrous trigones or any other anterior portion of the ventricular side of the native valve, or any portion on the posterior annulus of the native valve. The ventricular anchors may also help capture the native valve leaflets between the ventricular anchor and an outer surface of the expandable frame. If the prosthetic valve has ventricular wings or petals (as described below), the native valve leaflets may also be captured by the wings or petals and this may help keep the native valve leaflets out of the flow path. There may be any number of ventricular anchors, but in this example, there are three.

Facing radially inward toward the center of the device may be a plurality of anchor tabs 808, here mushroom head shaped tabs or T-shaped heads, which allow the prosthesis to be coupled to a delivery catheter as will be described below. The anchor tabs 808 are disposed on a portion of strut that joins two tails of Y-shaped struts 816 together. Thus, in this example there are three connection points that may be made with a delivery catheter.

Prosthetic valve 800 also includes arcuate struts 830 which have opposed ends which slope in opposite directions and a curved connector at the inflection point. Here, there are three arcuate struts 830 and each end of the arcuate struts is coupled to the arms of a Y-shaped strut 818 to form petals or wings. The petals or wings form a second ventricular anchor on the ventricular side of the prosthesis as well helping to capture native valve leaflets. The petals or wings may extend downward away from the prosthesis toward the ventricle during delivery and initial deployment and then the petals or wings extend radially outward and away from the anchor in the fully expanded configuration to form a flange circumferentially disposed around the expandable frame that can engage a ventricular portion of the native valve just below the annulus so that the annulus is captured between the petals or wings, and the upper rings. The upper atrial flared region and the lower ventricular wings or petals therefore provide upper and lower shoulders that may act as a clamp that can capture or sandwich the native valve annulus therebetween, providing good purchase of the tissue for anchoring the prosthesis into the native anatomy. Additionally, the ventricular wings or petals also may help capture the native valve leaflets and move them out of the flow passage to ensure optimal valve function. Here, three struts 830 are shown but any number may be used. The ventricular anchors 814 are substantially the same as previously described in FIG. 6A and may be used in conjunction with the petals or wings to further help secure the prosthetic valve to the native valve.

FIG. 8B illustrates prosthetic valve 800 of FIG. 8A after shape setting and in a partially deployed configuration where the atrial end has expanded into a conical shape with the atrial diameter increasing toward the ventricle to form the cone or flared region. The expanded configuration may be a paraboloid with a concave portion facing downward toward the ventricle, but still disposed above the valve annulus 850. A delivery catheter is not shown for convenience. The petals or wings 830 extend axially downward from the expandable frame and pass through the native valve orifice through the annulus 850. The petals or wings 830 extend substantially parallel with the longitudinal axis of the prosthesis in this partially deployed configuration. A cover (not shown) similar to cover 624 in FIG. 6B may be disposed over the struts 814 and any or all portions of the prosthetic frame to form a foot which helps create the ventricular anchors. The foot may include an enlarged head region and a narrower body. Again, the enlarged head provides a larger surface area and therefore minimizes pressure applied to tissue during anchoring in order to eliminate or reduce tissue trauma. Other aspects of FIG. 8B are the same as FIG. 8A.

FIG. 8C shows the prosthetic valve 800 of FIG. 8B in the fully deployed configuration where the atrial cone has been inverted to now form a paraboloid with the concave portion facing upward toward the atrium but above the annulus 850. The cone can then fit into the native valve and the walls of flared cone prevent the valve from slipping through the native valve orifice. Also, the petals or wings 830 have now radially expanded outward so they are orthogonal or otherwise transverse to the longitudinal axis of the prosthesis to form a flange that can be anchored against a lower surface of the native valve on the ventricular side. Additionally, the prosthetic valve also has ventricular anchors and they are shown extending radially outward to engage with the underside of the annulus, for example on the fibrous trigones on the anterior side of the native valve or on a posterior portion of the native valve. Again, a cover like cover 624 in FIG. 6B may be disposed over the ventricular anchors 814 to form the atraumatic tip of the ventricular anchors. The cover may be Dacron, or another polymer, or any material that has the desired mechanical properties. The cover may have an enlarged head region and a thinner elongate body region. The enlarged head region provided greater surface area in order to reduce contact pressure with tissue during anchoring in order to eliminate or reduce tissue piercing and trauma.

Figure 8D:
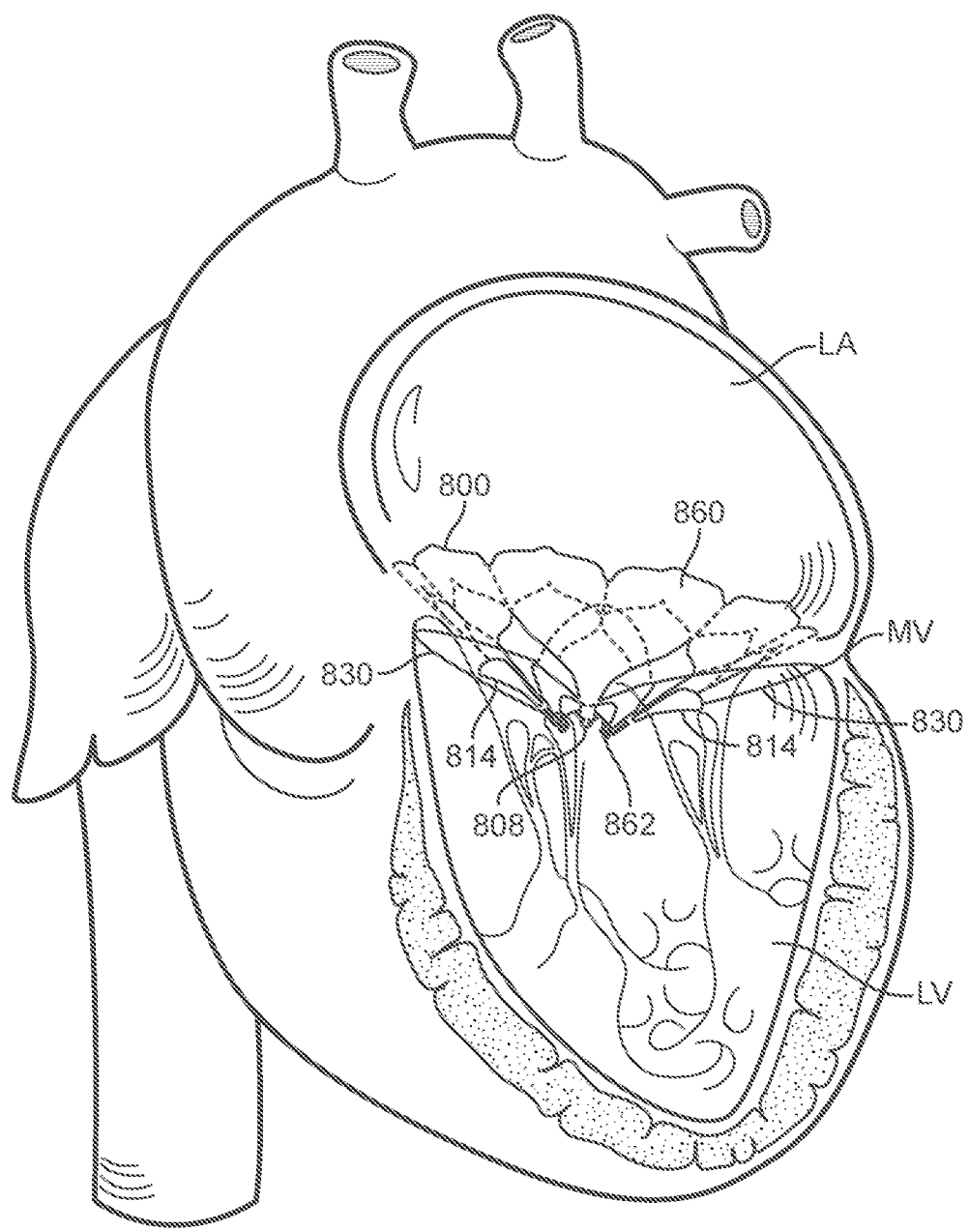
FIG. 8D shows the prosthetic valve of FIG. 8A disposed in a native mitral valve.

FIG. 8D shows the prosthetic valve 800 from FIG. 8A fully deployed in a native mitral valve MV. When fully deployed the larger diameter portion of the flare rests in the left atrium LA and prevents the prosthesis from migrating into the left ventricle LV. Ventricular anchor tabs 814 may include two anterior anchor tabs for anchoring on the fibrous trigones on an anterior portion of the native valve and a posterior anchor tab which anchors on a posterior portion such as a posterior shelf of the native valve. Ventricular wings 830 or petals are also disposed on the ventricular side to further help with anchoring on a ventricular side of the native valve. FIG. 8D is shown with the cover 860 such as Dacron or another polymer, fabric, or tissue coupled to the expandable frame. Prosthetic leaflets 862 are shown attached to the commissure posts. Anchor tabs 808 on the commissure posts are used to releasably couple the prosthesis with a delivery catheter. Here, there are three anchor tabs.

Releasable Coupling with a Delivery Catheter

FIGS. 9A-9F illustrate a delivery catheter which may be used to carry any of the prosthetic valves disclosed herein. The delivery catheter may be releasably coupled to the prosthesis so that once the prosthesis has been correctly positioned and deployed, the prosthetic valve is released from the delivery catheter and left in place while the delivery system is removed from the patient.

Figure 9A:
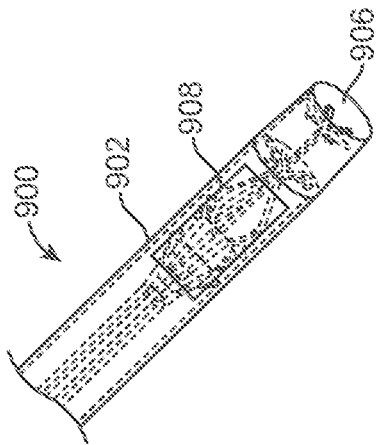
FIG. 9A-9F show a delivery catheter that is releasably coupled to a prosthetic valve.

FIG. 9A shows the outer surface of a delivery catheter 900 which includes an outer sheath 902 and a tapered atraumatic distal tip 904. The tapered atraumatic distal tip 904 may be removed before the prosthetic valve is inserted and expanded.

Figure 9B:
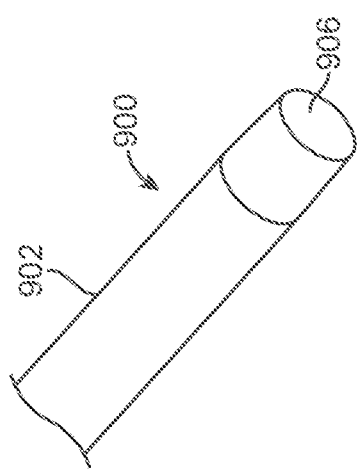

FIG. 9B shows that outer sheath 902 is generally tubular shaft with a single lumen 906 extending through the shaft. The lumen 906 is configured to house any of the prosthetic valves disclosed herein and provide a constraint that keeps the prosthetic valve in the collapsed configuration during delivery.

Figure 9C:
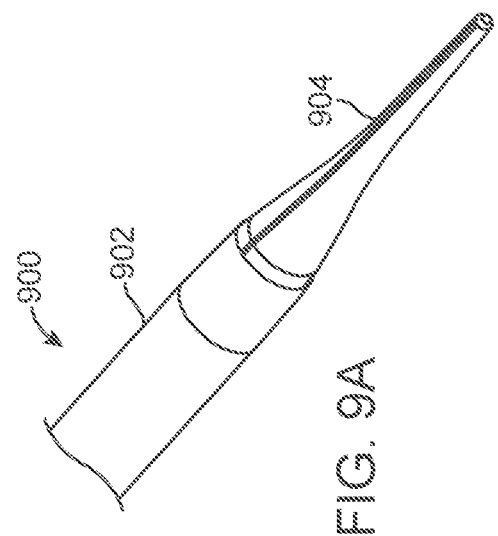

FIG. 9C shows the prosthesis 908 schematically disposed in lumen 906 of outer sheath 902. Prosthesis 908 may be any of the prosthetic valves disclosed herein, and is constrained in a collapsed configuration.

Figure 9D:
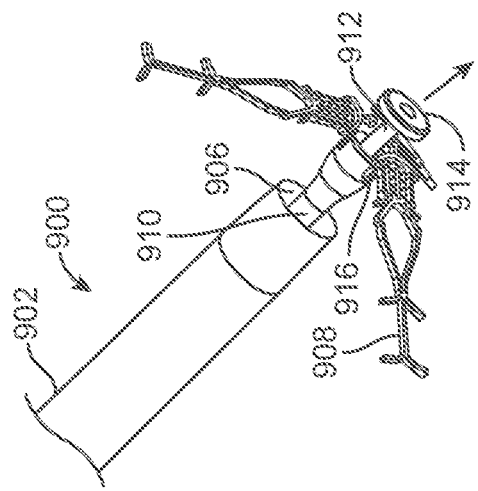

FIG. 9D shows proximal retraction of outer sheath 902 removes a constraint from prosthesis 908 and allows the prosthesis to partially self-expand but the sheath still is disposed over the portion of the prosthesis that is releasably engaged with the delivery catheter and this provides a constraint that prevents the prosthesis from inverting and fully expanding. Here, only the portions of the prosthesis which are releasably coupled to the delivery catheter are illustrated. The rest of the prosthetic valve has been omitted from FIGS. 9D-9F for convenience. As outer sheath 906 is retracted proximally, the prosthesis self-expands to form the partially deployed prosthesis where a paraboloid is formed with a concave portion facing downward toward the ventricle of the patient's heart. Therefore, an inverted cone shape is formed with the small end of the cone facing toward the atrium and the large end of the cone facing downward toward the ventricle. Only the arms of the prosthesis with the connector tabs remain coupled to the delivery catheter. Examples of tabs include the mushroom head shaped tabs or T-shaped tabs previously described above. The prosthesis remains in the atrium above the native valve at this stage of delivery and expansion.

Figure 9E:
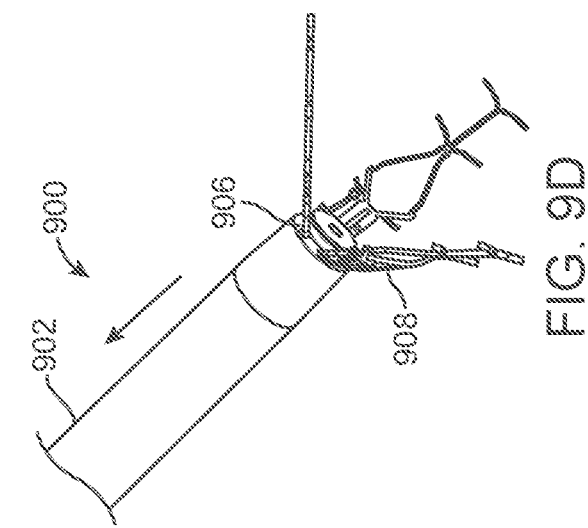

FIG. 9E shows that further proximal retraction of outer sheath 902 (or distal advancement of an intermediate shaft 910 disposed in the lumen 906 of outer sheath 902 allows the prosthetic valve to continue to open up and invert so that the paraboloid faces the opposite direction with the concave portion of the paraboloid facing toward the atrium. The prosthetic valve 908 remains coupled to the delivery catheter 900.

Figure 9F:
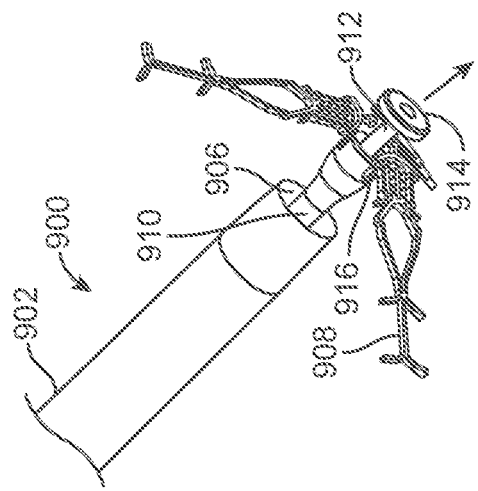

FIG. 9F shows release of the prosthetic valve 908 from the delivery catheter 900 once the prosthetic valve has been correctly positioned and expanded into the native valve. Here, an inner shaft 912 is slidably disposed in a lumen of intermediate shaft 910. As inner shaft 912 is advanced distally a disc or cap 914 is moved away from a hub coupled to the intermediate shaft 910. The hub includes slots 916 which capture the mushroom head or T-shaped head of the prosthesis. So, as the cap 914 moves away from the hub and slots 914, the mushroom head or T-shaped head becomes unconstrained and is free to self-expand out of the slot 914. Once out of the slot, the prosthesis 908 is then detached from the delivery catheter 900. Further details on the coupling mechanism are described below.

In the example of FIGS. 9A-9F, there are only 3 connections between the prosthetic valve and the delivery catheter. Additional connection points may be used such as by adding tabs on the ventricular anchors as seen in FIG. 7A so that there are six connection points. Any number of connection points may be used an any combination of connectors on the commissure or on the ventricular anchors may be used. Moreover, in this example or any example where there are multiple releasable connections between the prosthesis and the delivery catheter, the connections may all be released simultaneously, individually one after another in serial fashion and independently of one another, or in desired groupings, or in stages.

Figure 10C:
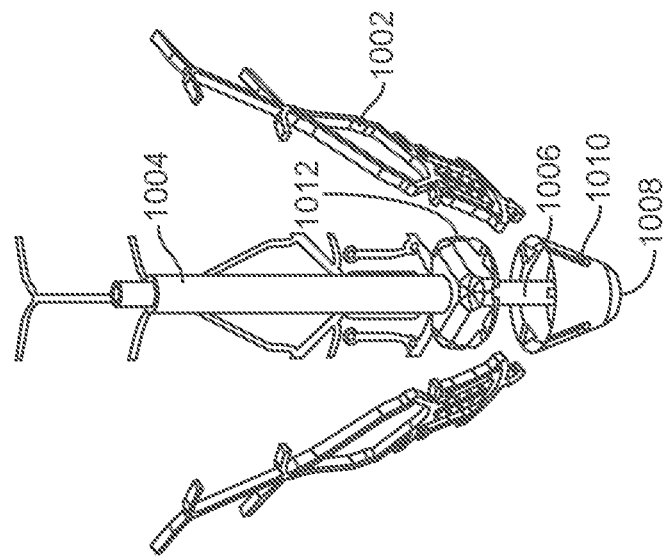
FIGS. 10A-10C show a locking mechanism for releasably coupling a prosthetic valve with a delivery catheter.
Figure 10B:
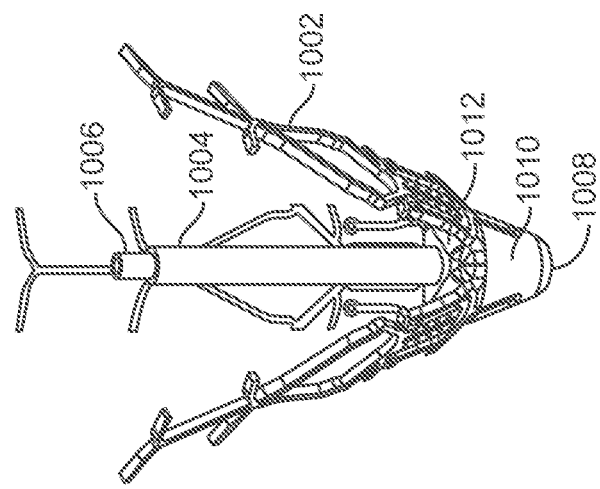
Figure 10A:
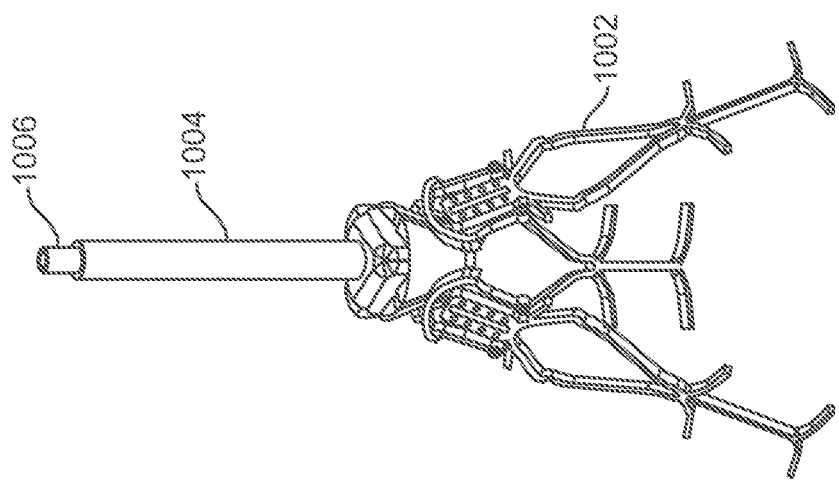

FIGS. 10A-10C show another example of a coupling mechanism that may be used to releasably couple a prosthetic valve with the delivery system. This example is similar to that shown in FIGS. 9A-9F with the major difference being that the slotted region on the hub and the disc or cap are reversed. The outer sheath is omitted from FIGS. 10A-10C for convenience.

In FIG. 10A the delivery catheter includes an inner shaft 1006 and an intermediate shaft 1004 slidably disposed over inner shaft 1006. Prosthetic valve 1002 is releasably coupled to the delivery catheter. Again, only the portions of prosthetic valve coupled to the delivery catheter are shown. The prosthetic valve 1002 may be any of the prosthetic valves disclosed herein. Also, in this view, the prosthesis is partially deployed and expanded to form the paraboloid with the concave portion facing downward toward the ventricle. The paraboloid also may be described as an inverted cone with the small end of the cone facing toward the atrium and the large end of the cone facing downward toward the ventricle.

In FIG. 10B further retraction of an outer sheath (not shown) allows the prosthesis to continue to expand and invert so that the prosthesis forms a cone with the larger diameter end facing toward the atrium and the smaller diameter end facing toward the ventricle. A hub 1008 with slots 1010 is coupled to the inner shaft 1006. The slots 1010 are sized to receive the T-shaped heads or mushroom heads on the prosthesis and hold them when the disc or cap 1012 is apposed with the hub 1008. Disc or cap 1012 is coupled to intermediate shaft 1004.

In FIG. 10C distal advancement of inner shaft 1006 moves hub 1008 away from cap or disc 1012 exposing slots 1010 and allowing the mushroom head or T-shaped heads of the prosthesis to release from the delivery catheter. Or intermediate shaft 1004 may be retracted proximally to separate the disc or cap from the hub, or a combination of proximal retraction of intermediate shaft 1004 and distal advancement inner shaft 1006 may be used to separate the two and release the prosthetic valve from the delivery catheter.

In the example of FIGS. 10A-10C, there are only 3 connections between the prosthetic valve and the delivery catheter. Additional connection points may be used such as by adding tabs on the ventricular anchors as seen in FIG. 7A so that there are six connection points. Any number of connection points may be used an any combination of connectors on the commissure or on the ventricular anchors may be used.

Figure 11:
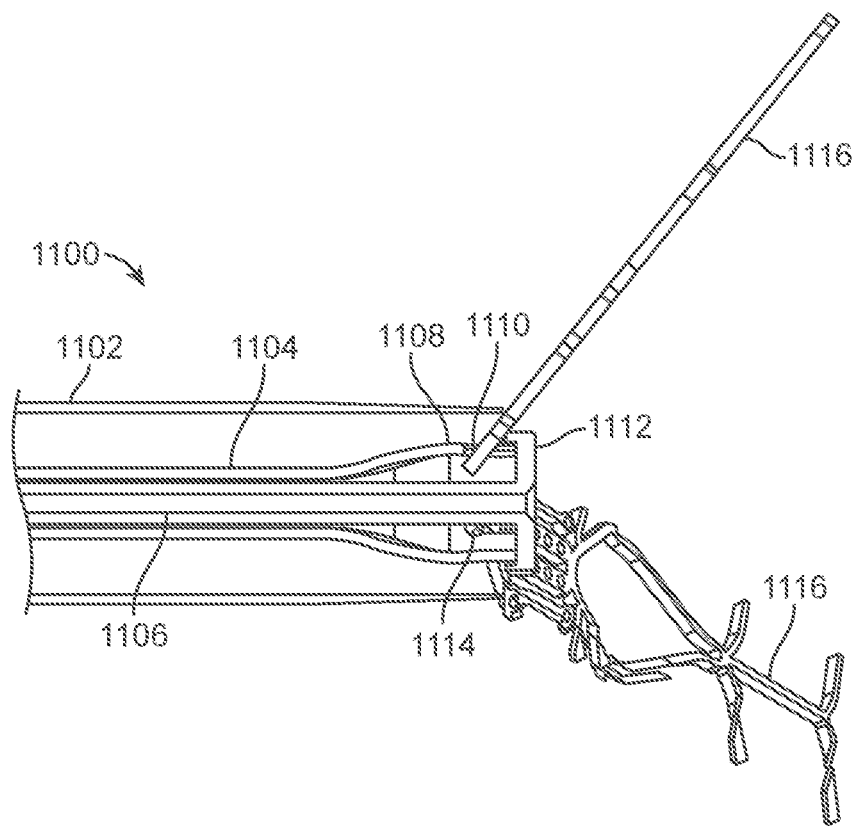
FIG. 11 shows a side view of a locking mechanism for releasably coupling a prosthetic valve with a delivery catheter.

FIG. 11 shows a side view of the releasable connection between a prosthetic valve and a delivery catheter and highlights an example of a locking mechanism that allows the prosthetic valve to be releasably coupled with the delivery catheter.

The delivery catheter 1100 includes an outer sheath 1102 slidably disposed over an intermediate shaft 1104 which is slidably disposed over an inner shaft 1106. All three shafts may move proximally or distally relative to one another. The outer sheath 1102 includes a lumen that houses a prosthetic valve 1116. The prosthetic valve 1116 may be any of the prosthetic valves disclosed herein. This figure only shows the portions of the prosthetic valve that are releasably coupled to the delivery catheter. The rest of the valve has been omitted for convenience. A hub 1108 with slots 1110 is coupled to the intermediate shaft. A cap or disc 1112 is coupled to the inner shaft 1106. Tabs 1114 such as mushroom heads or T-shaped heads may fit in the slots 1110 in the hub and when the cap 1112 is apposed with the hub, the tabs 1114 are captured and thus the prosthetic valve is coupled to the delivery catheter. Once the prosthetic valve is fully deployed and positioned, the inner shaft 1106 may be moved relative to the intermediate shaft 1104 so the cap is moved away from the hub, thereby allowing the tabs 1114 to release from the slots 1110 and decouple the prosthetic valve from the delivery catheter.

Figure 12B:
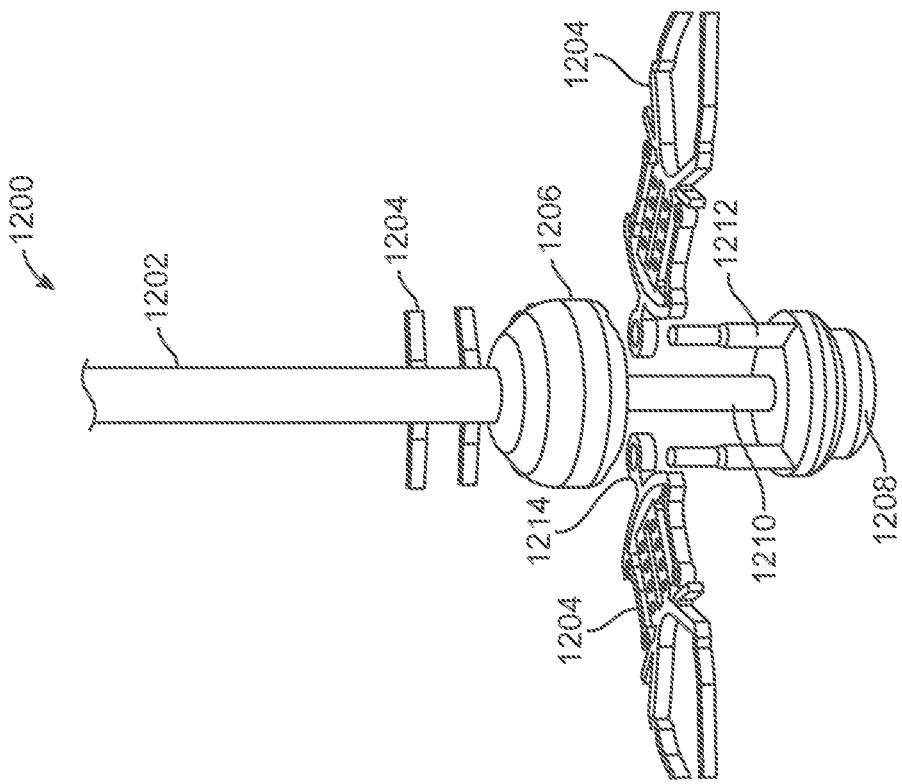
FIGS. 12A-12B show a locking mechanism for releasably coupling a prosthetic valve with a delivery catheter.
Figure 12A:
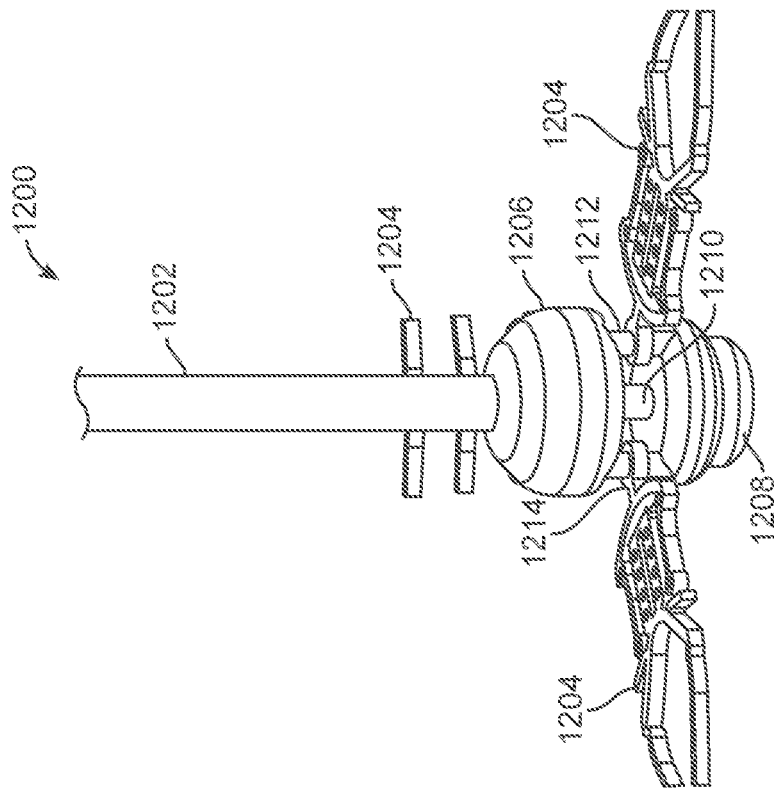

FIGS. 12A-12B illustrate another example of a locking mechanism for releasably coupling a prosthetic valve with a delivery catheter.

FIG. 12A shows delivery catheter 1200 which includes an outer sheath (not illustrated) for housing the prosthetic valve, an intermediate shaft 1202 slidably disposed in the outer sheath, and an inner shaft 1210 slidably disposed in the intermediate shaft 1202. A cap 1206 is coupled to the intermediate shaft 1202 and a hub 1208 has pins 1212 extending proximally from the hub and parallel with the longitudinal axis of the delivery catheter 1200. Here, only the arms or portions of the prosthetic valve 1204 that are releasably coupled with the delivery catheter are shown. The prosthetic valve 1204 may be any of the examples disclosed herein, and includes tabs 1214 with an aperture through the tip of the tab. The pins 1212 may be disposed in the apertures to releasably couple the prosthetic valve with the delivery catheter when the cap is apposed with the pins.

FIG. 12B shows release of the prosthetic valve 1204 from the delivery catheter 1200. Here, intermediate shaft 1202 is retracted proximally or inner shaft 1210 is advanced distally, or a combination of both proximal and distal motion of shafts 1202, 1210 move the cap 1206 away from the pins 1212 allowing the apertures 1214 in the connector tabs on the prosthetic valve 1204 to slide off the pins thereby decoupling the prosthetic valve from the delivery catheter.

In any of the examples of locking mechanisms for coupling and decoupling the prosthesis from the delivery catheter, it may be desirable to recapture the prosthetic valve. This may be accomplished any time up until the prosthetic valve is released from the delivery catheter. Thus, if the prosthesis requires repositioning or for some other reason the physician decides not to implant the prosthesis, the operator may allow the prosthesis to return to its unbiased shape of being concave facing downstream and the prosthesis may be resheathed and constrained in its collapsed configuration. Once it is repositioned or a decision is made to deploy the prosthesis, the deployment procedure may be recommenced.

Delivery Method

FIGS. 13A-13D illustrate an example of a method of delivering a prosthetic valve to a mitral valve in a patient.

Figure 13A:
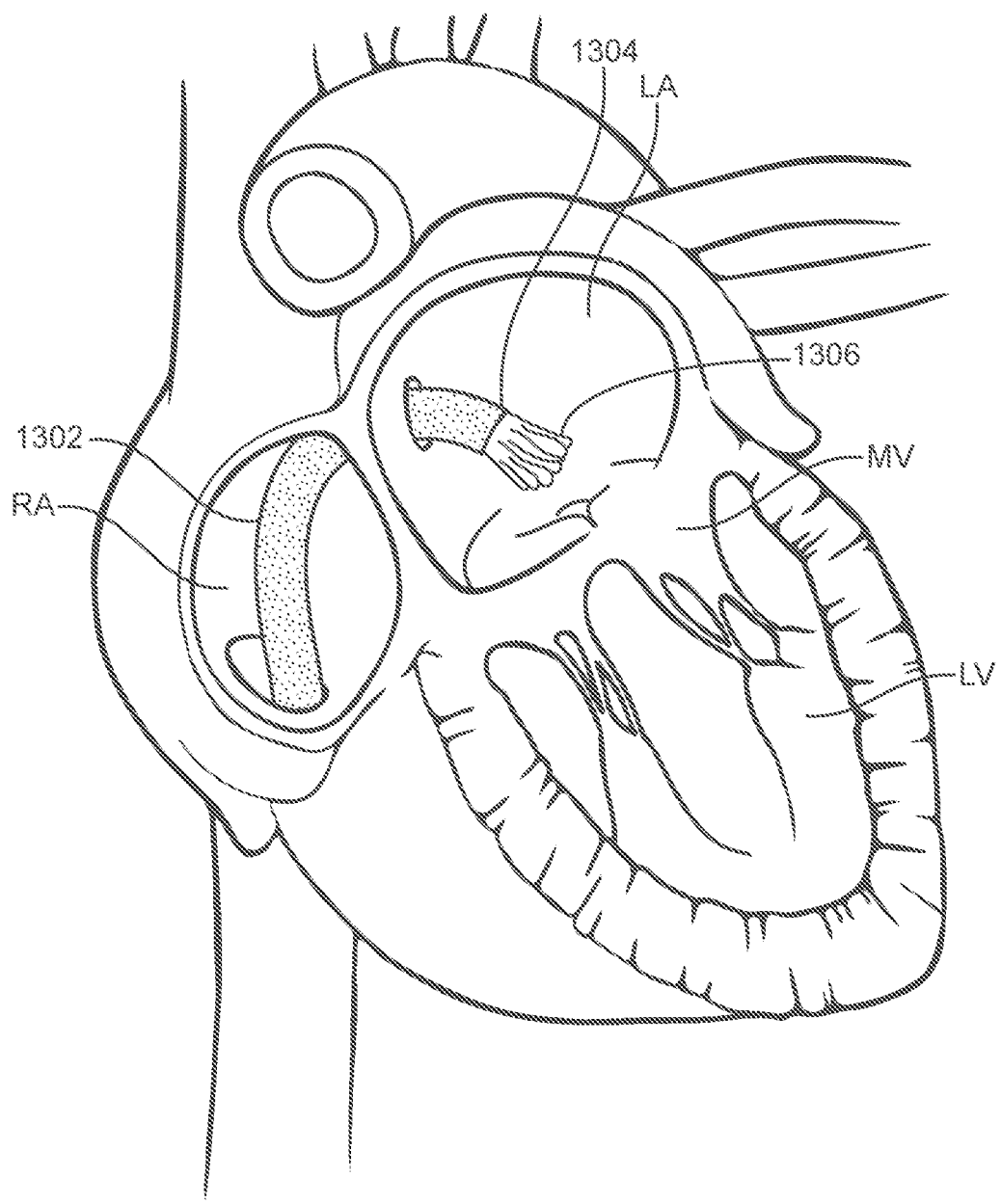
FIGS. 13A-13D illustrate an example of a method for deploying a prosthetic valve in a native valve.

In FIG. 13A, a sheath 1302 is introduced into the patient's heart using techniques known in the art such as percutaneously through a vein in the groin or via a cutdown, and over a guidewire. The sheath 1302 is advanced transseptally across the septal wall from the right atrium RA to the left atrium LA. A delivery catheter 1304 carrying a prosthetic valve 1306 such as any of the prosthetic valves described herein, is advanced through the sheath 1302 into the left atrium. The distal tip of the delivery catheter is positioned or steered so that it is adjacent the native mitral valve MV. The sheath may be proximally retracted or the delivery catheter advanced distally past the sheath to partially expose the prosthetic valve 1306.

Figure 13B:
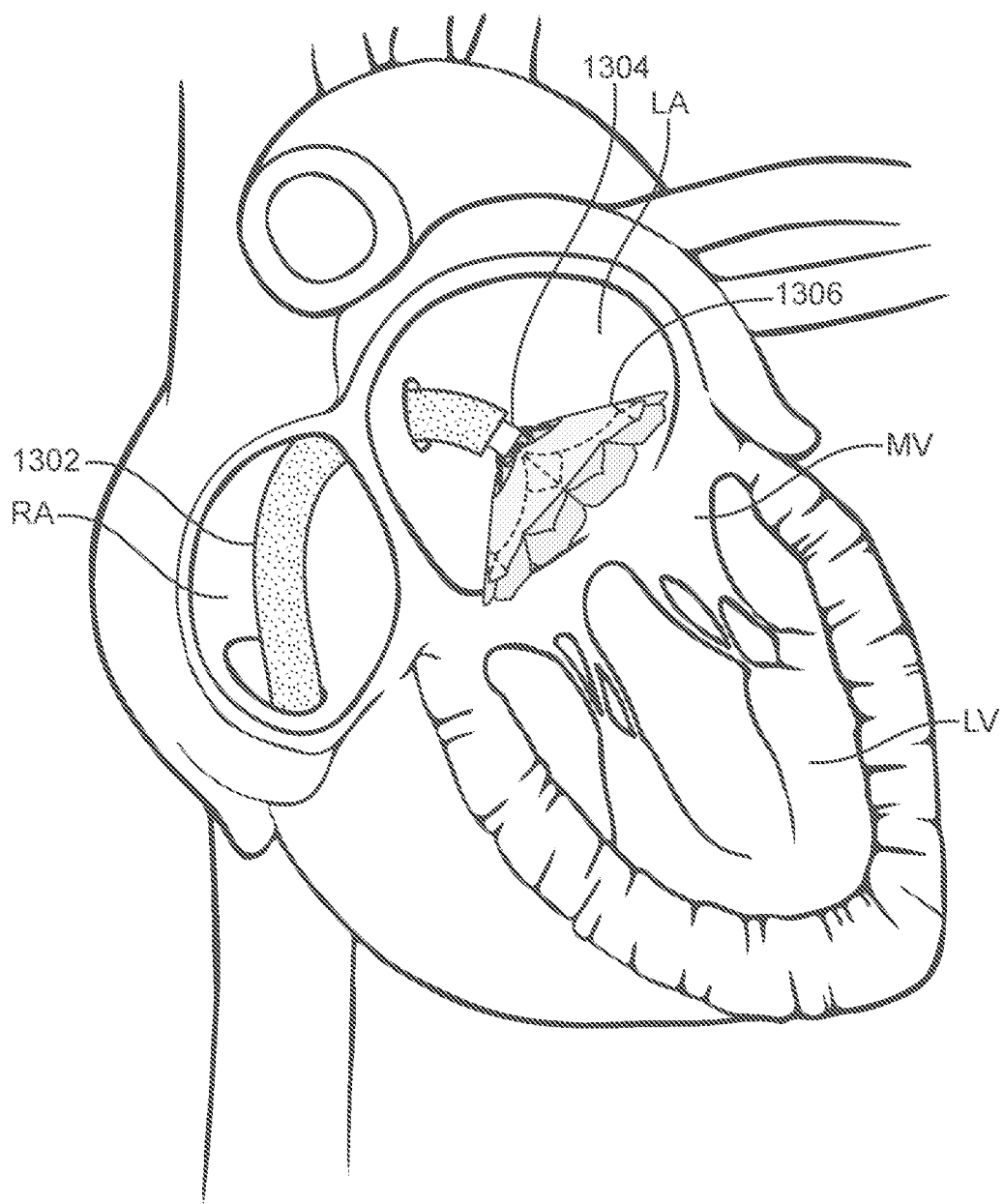

FIG. 13B the sheath is removed from the prosthetic valve 1306 thereby removing a constraint and allowing the prosthetic valve 1306 to expand into an intermediate configuration. The intermediate configuration is a cone shape or paraboloid with the concave surface facing downward toward the ventricle. The small diameter portion of the cone is facing the left atrium and the larger diameter portion of the cone faces the ventricle. The prosthetic valve is still coupled to the delivery catheter and disposed in the left atrium LA above the mitral valve MV.

Figure 13C:
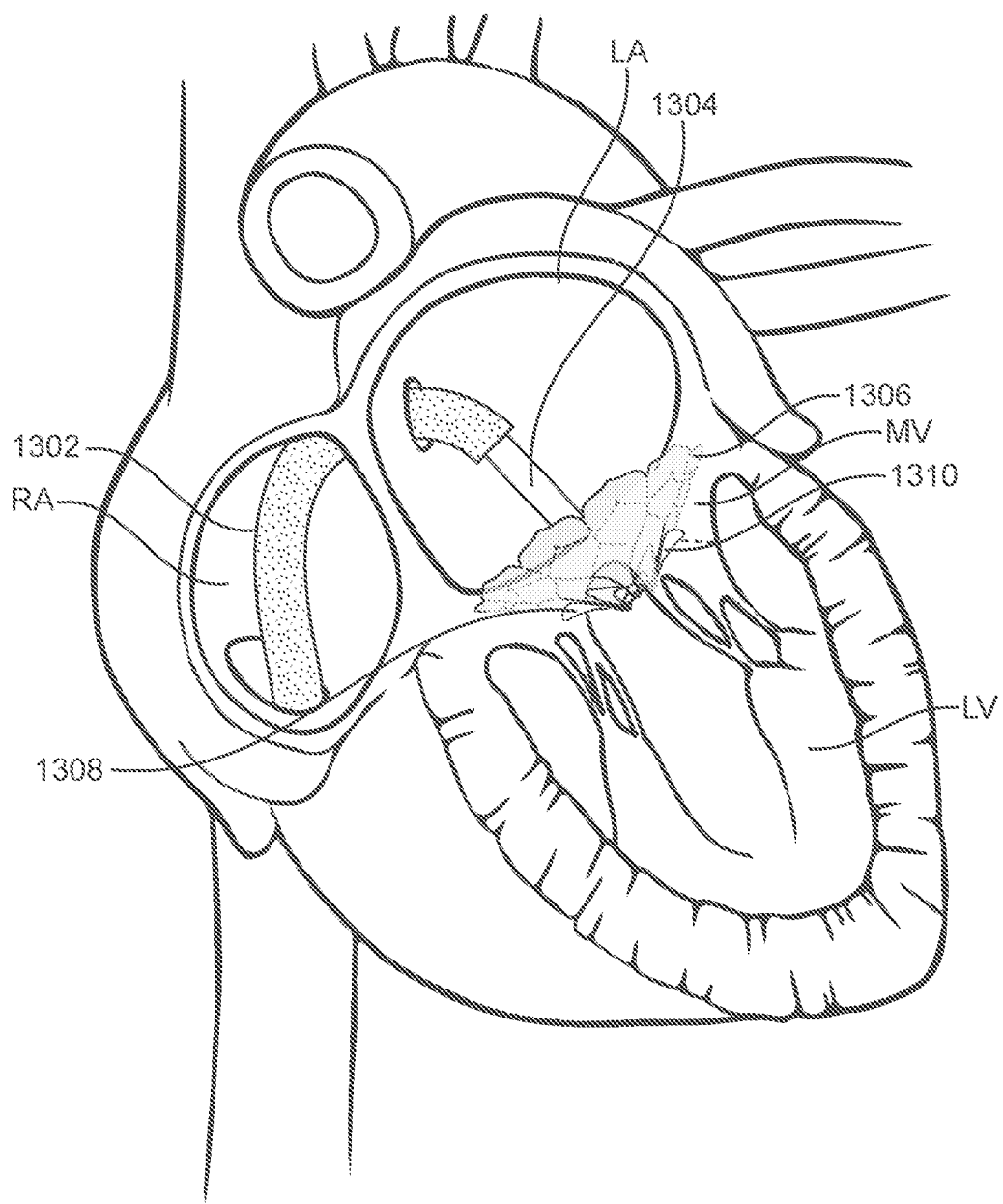

In FIG. 13C further expansion of the prosthetic valve 1306 and optionally with distal pressure applied to the prosthesis against the mitral valve MV, the prosthesis 1306 inverts so that the cone now has its large diameter portion facing the left atrium LA and the smaller diameter portion faces toward the left ventricle LV. The cone may be a paraboloid shape with the concave portion facing toward the left atrium LA and the convex portion facing toward the left ventricle. The ventricular anchor tabs also expand radially outward to engage a ventricular portion of the native valve. For example, the prosthetic valve may have two anterior ventricular anchors 1308 that engage the fibrous trigones on the anterior portion of the native mitral valve and a posterior ventricular anchor 1310 that engages a posterior portion of the native valve on the ventricular side. If the posterior portion has an annular posterior shelf region, the posterior ventricular anchor may land there.

Figure 13D:
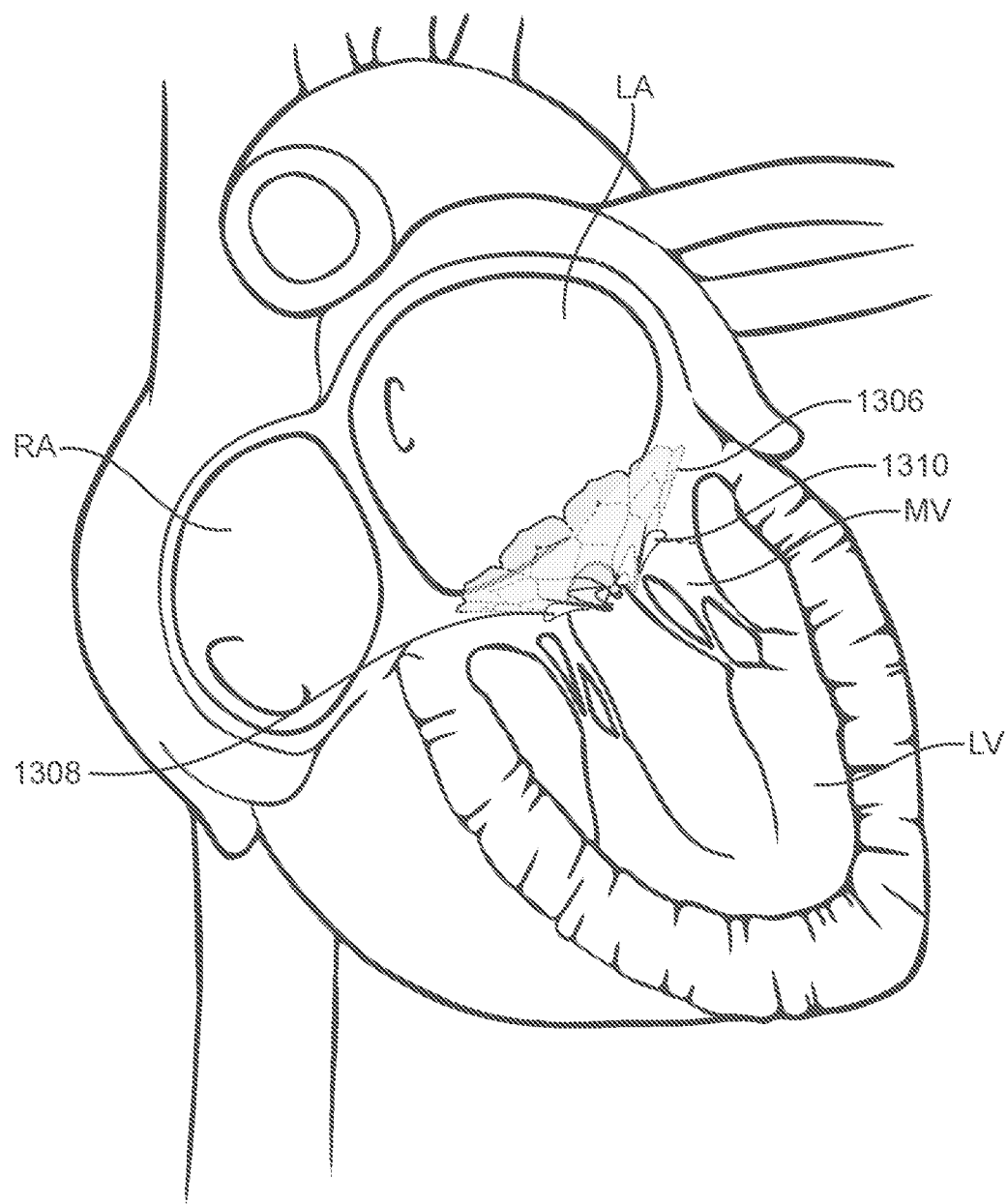

In FIG. 13D the prosthetic valve 1306 is fully deployed and anchored into the native valve and the delivery catheter and sheath have been removed from the patient.

Figure 14:
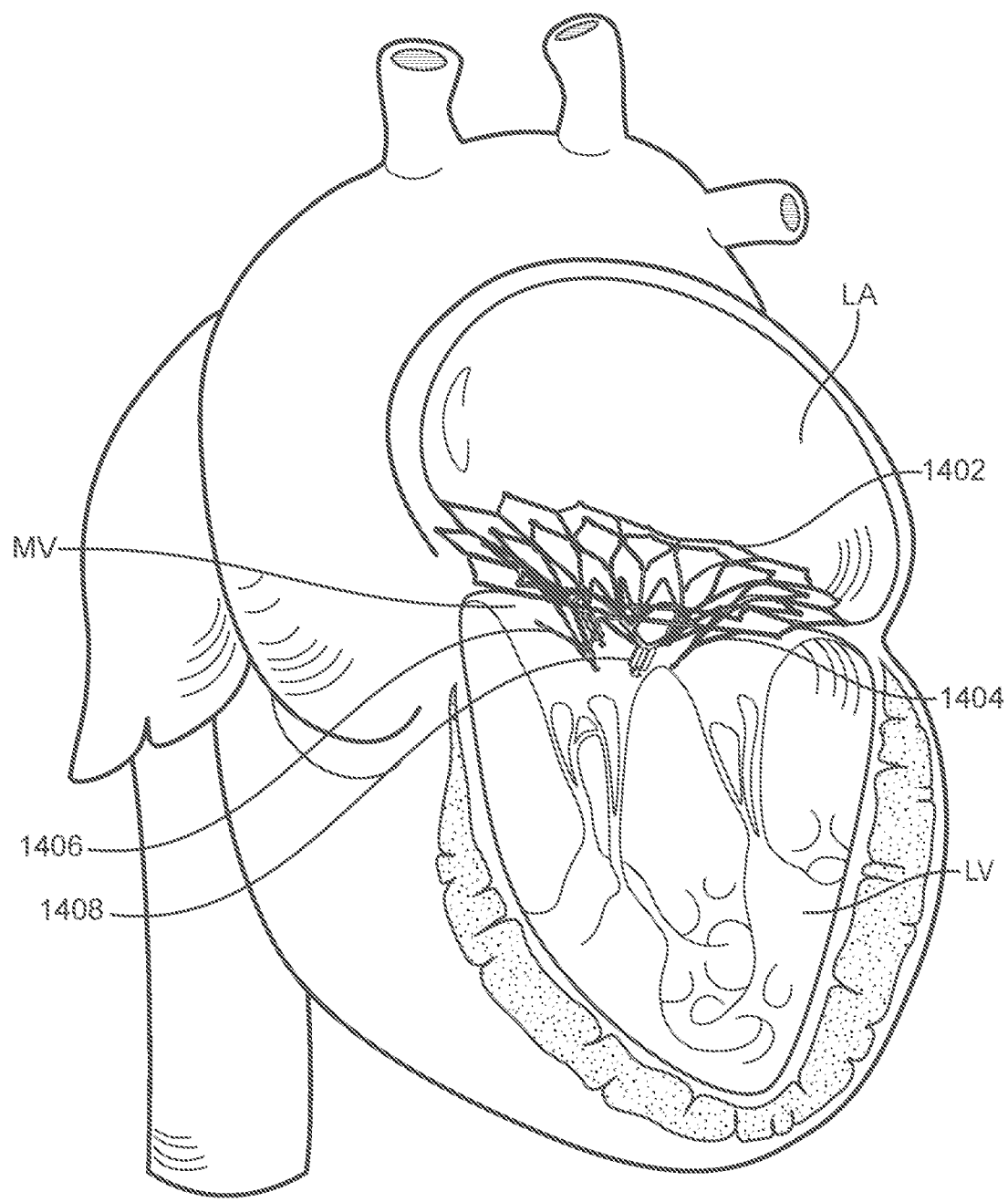
FIG. 14 shows an example of a prosthetic valve in a native valve.

FIG. 14 shows a prosthetic valve 1402 disposed in a native mitral valve MV. When fully deployed the larger diameter portion of the cone rests in the left atrium LA and prevents the prosthesis from migrating into the left ventricle. Ventricular anchor tabs may include two anterior anchor tabs 1406 for anchoring on the fibrous trigones on an anterior portion of the native valve and a posterior anchor tab 1404 which anchors on a posterior portion such as a posterior shelf of the native valve. FIG. 14 is shown without a cover and without the prosthetic leaflets in order to show the struts of the ventricular anchor tabs 1404, 1406 and the commissure tabs 1408. In this example all three ventricular anchors and all three commissure tabs include anchor tabs for releasable coupling with a delivery catheter such as those previously described.

FIGS. 15A-15D illustrate another example of deployment of a prosthetic valve such as the example in FIGS. 8A-8C.

Figure 15A:
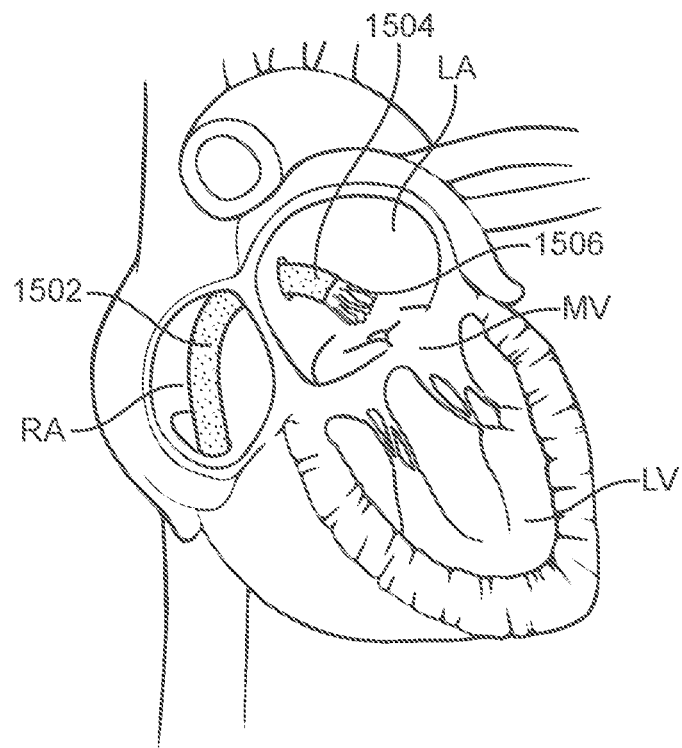
FIGS. 15A-15D show another example of a method for deploying a prosthetic valve in a native valve.

In FIG. 15A, a sheath 1502 is introduced into the patient's heart using techniques known in the art such as percutaneously through a vein in the groin or via a cutdown, and over a guidewire. The sheath 1502 is advanced transseptally across the septal wall from the right atrium RA to the left atrium LA. A delivery catheter 1504 carrying a prosthetic valve 1506 such as the valve in FIGS. 8A-8C is advanced through the sheath 1502 into the left atrium. The distal tip of the delivery catheter is positioned or steered so that it is adjacent the native mitral valve MV. The sheath may be proximally retracted, or the delivery catheter advanced distally past the sheath to partially expose the prosthetic valve 1506.

Figure 15B:
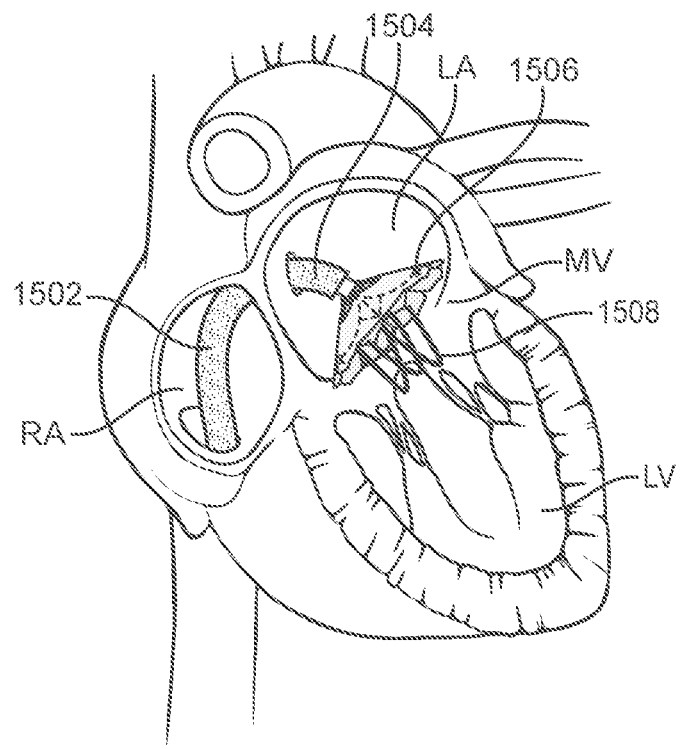

FIG. 15B the sheath is removed from the prosthetic valve 1506 thereby removing a constraint and allowing the prosthetic valve 1506 to expand into an intermediate configuration. The intermediate configuration is a cone shape or paraboloid with the concave surface facing downward toward the ventricle. The small diameter portion of the cone is facing the left atrium and the larger diameter portion of the cone faces the ventricle. The prosthetic valve is still coupled to the delivery catheter and disposed in the left atrium LA above the mitral valve MV. Wings or petals 1508 extend axially downward from prosthetic valve 1506 and may be substantially parallel with the longitudinal axis of the prosthetic valve. The wings or petals pass through the orifice of the native valve.

Figure 15C:
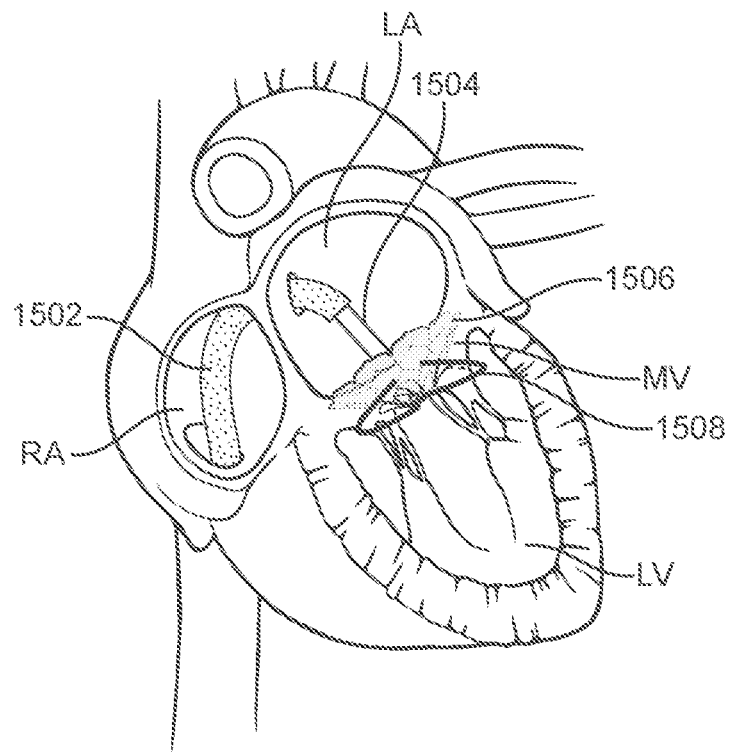

In FIG. 15C further expansion of the prosthetic valve 1506 and optionally with distal pressure applied to the prosthesis against the mitral valve MV, the prosthesis 1506 inverts so that the cone now has its large diameter portion facing the left atrium LA and the smaller diameter portion faces toward the left ventricle LV. The cone may be a paraboloid shape with the concave portion facing toward the left atrium LA and the convex portion facing toward the left ventricle. The ventricular anchor tabs if present, also expand radially outward to engage a ventricular portion of the native valve. For example, the prosthetic valve may have two anterior ventricular anchors that engage the fibrous trigones on the anterior portion of the native mitral valve and a posterior ventricular anchor that engages a posterior portion of the native valve on the ventricular side. If the posterior portion has an annular posterior shelf region, the posterior ventricular anchor may land there. The wings or petals 1508 expand radially outward so they are perpendicular or otherwise transverse to the longitudinal axis of the prosthesis to form a lower flange that can engage the bottom of the mitral valve on the ventricular surface to further anchor the device and also to help capture the native leaflets.

Figure 15D:
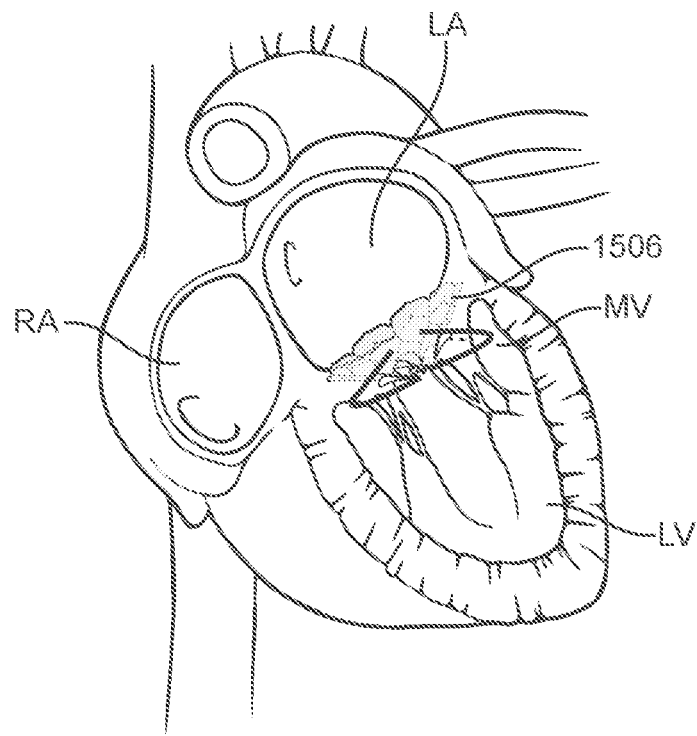

In FIG. 15D the prosthetic valve 1506 is fully deployed and anchored into the native valve and the delivery catheter and sheath have been removed from the patient.

Covering

Many of the figures illustrate only the expandable prosthetic valve frame without the prosthetic valve leaflets attached and also without a cover attached to the frame. However, as discussed above, a cover such as tissue, a polymer or fabric may be applied to the ventricular anchors to help form a foot that can engage tissue in the native valve without piercing or causing trauma to the tissue.

Additionally, in any of the examples disclosed herein, a cover may be applied to all of the frame or portions of the frame. The cover may be a fabric such as Dacron, or tissue such as pericardial tissue, or any other biocompatible material. The cover may be applied to the frame to prevent perivalvar leakage around the frame, as well as promoting tissue ingrowth to help further anchor and secure the prosthesis to the native anatomy. For example, the cover may be applied to the conical flange that rests against the atrial floor, or it may be applied to the ventricular flange that rests against the ventricular portion of the annulus, or the cover may be applied to both. The entire frame maybe covered, or only portions covered.

Also, as discussed, the examples generally do not illustrate the prosthetic valve leaflets attached to the prosthetic valve frame for convenience. However, prosthetic valve leaflets are known in the art and commonly two or three prosthetic leaflets may be applied to the frame to form either a bicuspid or tricuspid prosthetic valve. Of course, any number of leaflets may be used such as a single prosthetic leaflet, or four leaflets or more than four leaflets. The prosthetic valve leaflets may be tissue such as pericardial tissue, or they me fabric, a polymer, or other materials known in the art.

NOTES AND EXAMPLES

The following, non-limiting examples, detail certain aspects of the present subject matter to solve the challenges and provide the benefits discussed herein, among others.

In Example 1 a low-profile prosthetic valve for treating a native valve in a patient comprises: a radially expandable frame having an expanded configuration, a collapsed configuration, an atrial end and a ventricular end, wherein in the collapsed configuration the expandable frame is sized and shaped for minimally invasive delivery to the native valve, wherein in the expanded configuration the expandable frame is configured to engage the native valve, wherein the atrial end forms a flared shape in the expanded configuration, and is configured to engage an atrial surface of the native valve, wherein the flared shape flares downward toward a ventricle of the native valve when initially expanded followed by inversion of the flared shape to form a tapered shape tapering toward the ventricle and flaring toward an atrium of the native valve when fully expanded; and a plurality of prosthetic valve leaflets having a free end and an opposite end coupled to an inner portion of the expandable frame, an open configuration and closed configuration, wherein the open configuration the free ends of the plurality of prosthetic valve leaflets are disposed away from one another relative thereby forming an aperture through which fluid flows in an antegrade direction, and wherein in the closed configuration the free ends are disposed closer together than in the open configuration thereby substantially closing the aperture and preventing the fluid from flowing therethrough in a retrograde direction.

Example 2 is the prosthetic valve of Example 1, further comprising a plurality of commissure posts each having a free end and an opposite end, the opposite end coupled to the expandable frame, the free end facing the ventricle when the expandable frame is in the expanded configuration, and wherein the plurality of prosthetic valve leaflets are coupled to the plurality of commissure posts.

Example 3 is the prosthetic valve of any of Examples 1-2, wherein the free end comprises a plurality of apertures extending therethrough, the plurality of apertures sized to receive a suture filament that secures the plurality of prosthetic valve leaflets to the plurality of commissure posts.

Example 4 is the prosthetic valve of any of Examples 1-3, wherein the plurality of commissure posts each have a locking tab coupled to the free end, the locking tab configured to releasably couple the prosthetic valve with a delivery catheter.

Example 5 is the prosthetic valve of any of Examples 1-4, further comprising a plurality of ventricular anchors coupled to the ventricular end of the expandable frame, the ventricular anchors extending radially outward from the expandable frame in the expanded configuration, and configured to engage a ventricular side of the native valve.

Example 6 is the prosthetic valve of any of Examples 1-5, wherein at least one of the plurality of ventricular anchors and at least one of the plurality of commissure posts are disposed in a common closed cell in the expandable frame that is bounded by a plurality of struts.

Example 7 is the prosthetic valve of any of Examples 1-6, wherein the plurality of ventricular anchors each comprise a locking tab coupled to an inferior portion of the ventricular anchor, the locking tab on the ventricular anchor configured to releasably couple the prosthetic valve with a delivery catheter.

Example 8 is the prosthetic valve of any of Examples 1-7, wherein the plurality of ventricular anchors comprise an anterior ventricular anchor configured to engage a fibrous trigone on an anterior portion of a native mitral valve in the native heart, and a posterior ventricular anchor configured to engage a posterior portion of an annulus of the mitral valve or a posterior ventricular portion of the native valve.

Example 9 is the prosthetic valve of any of Examples 1-8, wherein the plurality of ventricular anchors comprise a cover element disposed over at least two struts coupled to the expandable frame.

Example 10 is the prosthetic valve of any of Examples 1-9, wherein the plurality of ventricular anchors comprise a V-shaped strut coupled to the expandable frame, wherein an apex of the V-shaped strut is configured to engage tissue, the prosthetic valve further comprising a cover element disposed over the V-shaped strut.

Example 11 is the prosthetic valve of any of Examples 1-10, wherein the expandable frame comprises a plurality of annular rings coupled together to form a paraboloidal shape.

Example 12 is the prosthetic valve of any of Examples 1-11, wherein the plurality of annular rings comprises a plurality of concentric rings having decreasing diameter coupled together.

Example 13 is the prosthetic valve of any of Examples 1-12, wherein adjacent annular rings are coupled together to form a plurality of closed cells extending circumferentially around the expandable frame.

Example 14 is the prosthetic valve of any of Examples 1-13, further comprising a plurality of ventricular wings on the ventricular end, wherein the plurality of ventricular wings has an expanded configuration and a collapsed configuration, wherein in the collapsed configuration the plurality of ventricular wings are substantially parallel with a longitudinal axis of the prosthetic valve, and wherein the expanded configuration the plurality of ventricular wings extend radially outward from the longitudinal axis to form a flange configured to engage a ventricular surface of the native valve.

Example 15 is a low-profile prosthetic valve system for treating a native valve in a patient, said system comprising: the prosthetic valve of any of Examples 1-14; and a delivery catheter releasably coupled to the prosthetic valve, the delivery catheter configured to deliver the prosthetic valve to the native valve.

Example 16 is the system of Example 15, wherein the delivery catheter comprises a locking element for releasably engaging the prosthetic valve.

Example 17 is a method for delivering a prosthetic valve to a native valve in a heart of a patient, said method comprising: providing a delivery catheter carrying the prosthetic valve; positioning the prosthetic valve adjacent the native valve; partially deploying the prosthetic valve so the prosthetic valve forms a flared shape disposed above the native valve and flaring toward a ventricle of the heart; inverting the flared shape so the initial flared shape becomes a tapered shape disposed above the native valve and tapering toward the ventricle; radially expanding a plurality of ventricular anchors or ventricular wings on a ventricular end of the prosthetic valve to engage a ventricular surface of the native valve; and releasing the prosthetic valve from the delivery catheter.

Example 18 is the method of Example 17, wherein radially expanding the plurality of ventricular anchors or ventricular wings comprises anchoring at least some of the plurality of ventricular anchors on a fibrous trigone of the native valve or a posterior ventricular portion of the native valve.

Example 19 is the method of any of Examples 17-18, wherein radially expanding the plurality of ventricular anchors or ventricular wings comprises radially expanding a plurality of ventricular wings from a position substantially parallel with a longitudinal axis of the prosthetic valve to a position extending radially outward from the longitudinal axis, and engaging the plurality of ventricular wings with a ventricular surface of the native valve.

Example 20 is the method of any of Examples 17-19, further comprising reducing or eliminating regurgitation across the prosthetic valve.

Example 21 is the method of any of Examples 17-20, wherein the native valve is a mitral valve.

Example 22 is the method of any of Examples 17-21, wherein releasing the prosthetic valve from the delivery catheter comprises disengaging a plurality of commissure posts on the prosthetic valve from the delivery catheter.

Example 23 is the method of any of Examples 17-22, wherein releasing the prosthetic valve from the delivery catheter comprises disengaging a plurality of locking tabs on the plurality of ventricular anchors from the delivery catheter.

In Example 24, the apparatuses or methods of any one or any combination of Examples 1-23 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A low-profile prosthetic valve for treating a native valve in a patient, said valve comprising:
    a radially expandable frame having an expanded configuration, a collapsed configuration, an atrial end and a ventricular end,
    wherein in the collapsed configuration the expandable frame is sized and shaped for minimally invasive delivery to the native valve,
    wherein in the expanded configuration the expandable frame is configured to engage the native valve,
    wherein the atrial end forms a flared shape in the expanded configuration, and configured to engage an atrial surface of the native valve,
    wherein the flared shape flares downward toward a ventricle of the native valve when initially expanded followed by inversion of the flared shape to form a tapered shape tapering toward the ventricle and flaring toward an atrium of the native valve when fully expanded;
    a plurality of prosthetic valve leaflets having a free end and an opposite end coupled to an inner portion of the expandable frame, an open configuration and closed configuration; and
    a plurality of ventricular wings on the ventricular end,
    wherein in the open configuration the free ends of the plurality of prosthetic valve leaflets are disposed away from one another relative thereby forming an aperture through which fluid flows in an antegrade direction,
    wherein in the closed configuration the free ends are disposed closer together than in the open configuration thereby substantially closing the aperture and preventing the fluid from flowing therethrough in a retrograde direction,
    wherein in the plurality of ventricular wings has an expanded configuration and a collapsed configuration,
    wherein in the collapsed configuration the plurality of ventricular wings is substantially parallel with a longitudinal axis of the prosthetic valve, and
    wherein the expanded configuration the plurality of ventricular wings extends radially outward from the longitudinal axis to form a flange configured to engage a ventricular surface of the native valve.

2. The prosthetic valve of claim 1, further comprising a plurality of commissure posts each having a free end and an opposite end, the opposite end coupled to the expandable frame, the free end facing the ventricle when the expandable frame is in the expanded configuration, and wherein the plurality of prosthetic valve leaflets are coupled to the plurality of commissure posts.

3. The prosthetic valve of claim 2, wherein the free end comprises a plurality of apertures extending therethrough, the plurality of apertures sized to receive a suture filament that secures the plurality of prosthetic valve leaflets to the plurality of commissure posts.

4. The prosthetic valve of claim 2, wherein the plurality of commissure posts each have a locking tab coupled to the free end, the locking tab configured to releasably couple the prosthetic valve with a delivery catheter.

5. The prosthetic valve of claim 1, further comprising a plurality of ventricular anchors coupled to the ventricular end of the expandable frame, the ventricular anchors extending radially outward from the expandable frame in the expanded configuration, and configured to engage a ventricular side of the native valve.

6. The prosthetic valve of claim 5, wherein at least one of the plurality of ventricular anchors and at least one of a plurality of commissure posts are disposed in a common closed cell in the expandable frame that is bounded by a plurality of struts.

7. The prosthetic valve of claim 5, wherein the plurality of ventricular anchors each comprise a locking tab coupled to an inferior portion of the ventricular anchor, the locking tab on the ventricular anchor configured to releasably couple the prosthetic valve with a delivery catheter.

8. The prosthetic valve of claim 5, wherein the plurality of ventricular anchors comprise an anterior ventricular anchor configured to engage a fibrous trigone on an anterior portion of a native mitral valve in the native heart, and a posterior ventricular anchor configured to engage a posterior portion of an annulus of the mitral valve or a posterior ventricular portion of the native valve.

9. The prosthetic valve of claim 5, wherein the plurality of ventricular anchors comprise a cover element disposed over at least two struts coupled to the expandable frame.

10. The prosthetic valve of claim 5, wherein the plurality of ventricular anchors comprise a V-shaped strut coupled to the expandable frame, wherein an apex of the V-shaped strut is configured to engage tissue, the prosthetic valve further comprising a cover element disposed over the V-shaped strut.

11. The prosthetic valve of claim 1, wherein the expandable frame comprises a plurality of annular rings coupled together to form a paraboloidal shape.

12. The prosthetic valve of claim 11, wherein the plurality of annular rings comprises a plurality of concentric rings having decreasing diameter coupled together.

13. The prosthetic valve of claim 11, wherein adjacent annular rings are coupled together to form a plurality of closed cells extending circumferentially around the expandable frame.

14. A low-profile prosthetic valve system for treating a native valve in a patient, said system comprising:
the prosthetic valve of claim 1; and
a delivery catheter releasably coupled to the prosthetic valve, the delivery catheter configured to deliver the prosthetic valve to the native valve.

15. The system of claim 14, wherein the delivery catheter comprises a locking element for releasably engaging the prosthetic valve.

16. A low-profile prosthetic valve for treating a native valve in a patient, said valve comprising:
a radially expandable frame having an expanded configuration, a collapsed configuration, an atrial end and a ventricular end,
wherein in the collapsed configuration the expandable frame is sized and shaped for minimally invasive delivery to the native valve,
wherein in the expanded configuration the expandable frame is configured to engage the native valve,
wherein the atrial end forms a flared shape in the expanded configuration, and configured to engage an atrial surface of the native valve,
wherein the flared shape flares downward toward a ventricle of the native valve when initially expanded followed by inversion of the flared shape to form a tapered shape tapering toward the ventricle and flaring toward an atrium of the native valve when fully expanded,
a plurality of prosthetic valve leaflets having a free end and an opposite end coupled to an inner portion of the expandable frame, an open configuration and closed configuration, and
a plurality of ventricular anchors coupled to the ventricular end of the expandable frame, the ventricular anchors extending radially outward from the expandable frame in the expanded configuration, and configured to engage a ventricular side of the native valve;
wherein in the open configuration the free ends of the plurality of prosthetic valve leaflets are disposed away from one another relative thereby forming an aperture through which fluid flows in an antegrade direction, and
wherein in the closed configuration the free ends are disposed closer together than in the open configuration thereby substantially closing the aperture and preventing the fluid from flowing therethrough in a retrograde direction.

17. The prosthetic valve of claim 16, wherein the plurality of ventricular anchors each comprise a locking tab coupled to an inferior portion of the ventricular anchor, the locking tab on the ventricular anchor configured to releasably couple the prosthetic valve with a delivery catheter.

18. The prosthetic valve of claim 16, wherein the plurality of ventricular anchors comprise a V-shaped strut coupled to the expandable frame, wherein an apex of the V-shaped strut is configured to engage tissue, the prosthetic valve further comprising a cover element disposed over the V-shaped strut.

19. The prosthetic valve of claim 16, wherein the expandable frame comprises a plurality of annular rings coupled together to form a paraboloidal shape.

20. The prosthetic valve of claim 16, further comprising:
a plurality of ventricular wings on the ventricular end,
wherein the plurality of ventricular wings has an expanded configuration and a collapsed configuration,
wherein in the collapsed configuration the plurality of ventricular wings is substantially parallel with a longitudinal axis of the prosthetic valve, and
wherein in the expanded configuration the plurality of ventricular wings extends radially outward from the longitudinal axis to form a flange configured to engage a ventricular surface of the native valve.

* * * * *